US011851476B2

(12) United States Patent
Kuramochi et al.

(10) Patent No.: US 11,851,476 B2
(45) Date of Patent: Dec. 26, 2023

(54) ANTIGEN-BINDING MOLECULE HAVING REGULATED CONJUGATION BETWEEN HEAVY-CHAIN AND LIGHT-CHAIN

(71) Applicant: Chugai Seiyaku Kabushiki Kaisha, Tokyo (JP)

(72) Inventors: Taichi Kuramochi, Shizuoka (JP); Meiri Kawazoe, Shizuoka (JP); Naoka Hironiwa, Shizuoka (JP); Tomoyuki Igawa, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/351,654

(22) PCT Filed: Oct. 31, 2012

(86) PCT No.: PCT/JP2012/078103
§ 371 (c)(1),
(2) Date: Apr. 14, 2014

(87) PCT Pub. No.: WO2013/065708
PCT Pub. Date: May 10, 2013

(65) Prior Publication Data
US 2014/0370020 A1    Dec. 18, 2014

(30) Foreign Application Priority Data
Oct. 31, 2011    (JP) .................. 2011-238873

(51) Int. Cl.
*C07K 16/00* (2006.01)
*C07K 16/28* (2006.01)
*C07K 16/30* (2006.01)
*C07K 16/46* (2006.01)

(52) U.S. Cl.
CPC .......... *C07K 16/00* (2013.01); *C07K 16/2866* (2013.01); *C07K 16/303* (2013.01); *C07K 16/468* (2013.01); C07K 2317/31 (2013.01); C07K 2317/522 (2013.01)

(58) Field of Classification Search
CPC .. C07K 16/00; C07K 16/468; C07K 2317/31; C07K 2317/522
USPC .................. 424/136.1; 435/69.6; 530/387.3; 536/23.53
See application file for complete search history.

(56) References Cited

U.S. PATENT DOCUMENTS

| 5,474,771 A | 12/1995 | Lederman et al. |
| 5,585,097 A | 12/1996 | Bolt et al. |
| 5,624,821 A | 4/1997 | Winter et al. |
| 5,648,260 A | 7/1997 | Winter et al. |
| 6,025,165 A | 2/2000 | Whitlow et al. |
| 6,126,980 A | 10/2000 | Smith et al. |
| 6,485,943 B2 | 11/2002 | Stevens et al. |
| 6,737,056 B1 | 5/2004 | Presta |
| 8,592,562 B2 | 11/2013 | Kannan et al. |
| 8,735,545 B2 | 5/2014 | Lazar et al. |
| 10,011,858 B2 | 7/2018 | Igawa et al. |
| 10,759,870 B2* | 9/2020 | Teranishi ............... C07K 16/36 |
| 11,066,483 B2* | 7/2021 | Nezu ....................... A61P 35/00 |
| 11,124,576 B2 | 9/2021 | Igawa et al. |
| 11,130,808 B2 | 9/2021 | Yan et al. |
| 11,142,587 B2 | 10/2021 | Igawa et al. |
| 11,168,344 B2 | 11/2021 | Igawa et al. |
| 2002/0137897 A1 | 9/2002 | Stevens et al. |
| 2003/0078385 A1 | 4/2003 | Arathoon et al. |
| 2003/0187225 A1 | 10/2003 | Penichet et al. |
| 2003/0224397 A1 | 12/2003 | Lowman et al. |
| 2004/0002587 A1 | 1/2004 | Watkins et al. |
| 2005/0118174 A1 | 6/2005 | Presta |
| 2005/0130224 A1 | 6/2005 | Saito et al. |
| 2006/0074225 A1 | 4/2006 | Chamberlain |
| 2006/0204493 A1 | 9/2006 | Huang |
| 2006/0235208 A1 | 10/2006 | Lazar et al. |
| 2006/0275282 A1 | 12/2006 | Moore et al. |
| 2007/0041978 A1 | 2/2007 | Hattori et al. |
| 2007/0178092 A1 | 8/2007 | Bolt et al. |
| 2007/0224188 A1 | 9/2007 | Allan et al. |
| 2007/0231329 A1 | 10/2007 | Lazar et al. |
| 2007/0254831 A1 | 11/2007 | Mezo et al. |
| 2007/0287170 A1 | 12/2007 | Davis et al. |
| 2008/0317758 A9 | 12/2008 | Presta |
| 2009/0324589 A1 | 12/2009 | Igawa et al. |
| 2010/0003254 A1 | 1/2010 | Hattori et al. |
| 2010/0015133 A1 | 1/2010 | Igawa et al. |
| 2010/0105874 A1 | 4/2010 | Schuurman et al. |

(Continued)

FOREIGN PATENT DOCUMENTS

| CN | 1842540 | 10/2006 |
| CN | 101198698 | 6/2008 |

(Continued)

OTHER PUBLICATIONS

Ibragimova and Eade (Biophysical Journal, Oct. 1999, vol. 77, pp. 2191-2198).*
Burgess et al, Journal of Cell Biology vol. 111 Nov. 1990 2129-2138.*
Lazar et al Molecular and Cellular Biology Mar. 1988 vol. 8 No. 3 1247-1252.*
Schwartz et al, Proc Natl Acad Sci USA vol. 84:6408-6411 (1987)).*
Lin et al Biochemistry USA vol. 14:1559-1563 (1975)).*

(Continued)

*Primary Examiner* — Lynn A Bristol
(74) *Attorney, Agent, or Firm* — Fish & Richardson P.C.

(57) ABSTRACT

It was found that association between CH1 and CL can be suppressed by substituting amino acids that exist on the interface between CH1 and CL with electrically-charged amino acids, and that formation of heterogeneous molecules is enabled more efficiently than by introducing knobs into holes mutations into CH3 domain.

27 Claims, 13 Drawing Sheets
Specification includes a Sequence Listing.

(56) References Cited

U.S. PATENT DOCUMENTS

| | | |
|---|---|---|
| 2010/0178298 A1 | 7/2010 | Lindhofer |
| 2010/0221252 A1 | 9/2010 | Bigler et al. |
| 2010/0286374 A1 | 11/2010 | Kannan et al. |
| 2010/0291072 A1 | 11/2010 | Lowman et al. |
| 2010/0298542 A1 | 11/2010 | Igawa et al. |
| 2010/0331527 A1 | 12/2010 | Davis et al. |
| 2011/0021755 A1 | 1/2011 | Lazar et al. |
| 2011/0123532 A1 | 5/2011 | Gurney et al. |
| 2011/0236374 A1 | 9/2011 | Shitara et al. |
| 2011/0287009 A1 | 11/2011 | Scheer et al. |
| 2012/0009188 A1 | 1/2012 | Behrens |
| 2012/0010387 A1 | 1/2012 | Niwa et al. |
| 2012/0065379 A1 | 3/2012 | Igawa et al. |
| 2012/0149876 A1 | 6/2012 | Von Kreudenstein |
| 2013/0018174 A1 | 1/2013 | Igawa et al. |
| 2013/0039913 A1 | 2/2013 | Labrijn et al. |
| 2013/0101581 A1 | 4/2013 | Kuramochi et al. |
| 2013/0115208 A1 | 5/2013 | Ho et al. |
| 2013/0195849 A1 | 8/2013 | Spreter Von Kreudenstein et al. |
| 2013/0330345 A1 | 12/2013 | Igawa et al. |
| 2014/0093496 A1 | 4/2014 | Mimoto et al. |
| 2014/0112914 A1* | 4/2014 | Nezu .............. C07K 16/30 424/133.1 |
| 2014/0303356 A1 | 10/2014 | Gramer et al. |
| 2014/0370020 A1 | 12/2014 | Kuramochi et al. |
| 2015/0337053 A1 | 11/2015 | McCarthy et al. |
| 2016/0168259 A1* | 6/2016 | Igawa .............. A61K 9/0019 424/135.1 |
| 2016/0229915 A1 | 8/2016 | Igawa et al. |
| 2017/0267783 A1 | 9/2017 | Nezu et al. |
| 2018/0244805 A1 | 8/2018 | Nezu et al. |
| 2018/0346605 A1 | 12/2018 | Chiu et al. |
| 2019/0352421 A1 | 11/2019 | Adams et al. |
| 2020/0087380 A1* | 3/2020 | Kuramochi ........ C07K 16/2866 |
| 2020/0123256 A1 | 4/2020 | Hoshino et al. |
| 2020/0223940 A1* | 7/2020 | Teranishi ............ A61P 7/04 |
| 2020/0354473 A1* | 11/2020 | Teranishi ............ A61P 7/04 |
| 2022/0010030 A1 | 1/2022 | Igawa et al. |
| 2022/0041756 A1* | 2/2022 | Nezu ................. A61P 11/00 |
| 2022/0267822 A1 | 8/2022 | Igawa et al. |
| 2023/0075499 A1 | 3/2023 | Kim et al. |
| 2023/0152280 A1 | 5/2023 | Sato et al. |

FOREIGN PATENT DOCUMENTS

| | | |
|---|---|---|
| CN | 102471378 | 5/2012 |
| CN | 102782131 | 11/2012 |
| CN | 102946906 | 2/2013 |
| EP | 0 811 691 | 12/1997 |
| EP | 1 378 520 | 1/2004 |
| EP | 1 674 111 | 6/2006 |
| EP | 1 449 238 B | 11/2006 |
| EP | 1 870 458 | 12/2007 |
| EP | 1 870 459 | 12/2007 |
| EP | 1 900 814 | 3/2008 |
| EP | 2 009 101 | 12/2008 |
| EP | 2 194 006 | 6/2010 |
| EP | 2 194 066 | 6/2010 |
| EP | 2 431 393 A | 3/2012 |
| EP | 2 445 936 | 5/2012 |
| EP | 2 543 727 | 1/2013 |
| EP | 2 543 730 A | 1/2013 |
| EP | 2 576 621 | 4/2013 |
| EP | 2 647 707 | 10/2013 |
| EP | 2 698 431 A | 2/2014 |
| EP | 2 905 290 | 8/2015 |
| EP | 2 914 634 | 9/2015 |
| EP | 3 434 767 | 1/2019 |
| EP | 3 690 050 A | 8/2020 |
| JP | H08-500979 | 2/1996 |
| JP | H11-500915 | 1/1999 |
| JP | H11-500916 | 1/1999 |
| JP | 2004-86862 | 3/2004 |
| JP | 2007-503206 | 2/2007 |
| JP | 2009-527499 | 7/2009 |
| JP | 2010-522701 | 7/2010 |
| JP | 2010-532369 | 10/2010 |
| JP | 2011-508604 | 3/2011 |
| JP | 2012-552527 | 9/2012 |
| JP | 2012-531439 | 12/2012 |
| JP | 2013-529084 | 7/2013 |
| JP | 2013-529190 | 7/2013 |
| JP | 6534615 | 6/2019 |
| KR | 2008/0013875 | 2/2008 |
| KR | 2014/0014167 | 2/2014 |
| KR | 2014/0084249 | 7/2014 |
| KR | 10-1960109 | 3/2019 |
| MX | 349057 | 7/2017 |
| RU | 2323737 | 5/2008 |
| RU | 2355705 | 5/2009 |
| TW | 2007/22517 | 6/2007 |
| WO | WO 94/05690 | 3/1994 |
| WO | WO 96/27011 | 9/1996 |
| WO | WO 97/10354 | 3/1997 |
| WO | WO 98/50431 | 11/1998 |
| WO | WO 99/58572 | 11/1999 |
| WO | WO 00/18806 | 4/2000 |
| WO | WO 00/42072 | 7/2000 |
| WO | WO 01/90192 | 11/2001 |
| WO | WO 03/012069 | 2/2003 |
| WO | WO 03/035835 | 5/2003 |
| WO | WO 03/074679 | 9/2003 |
| WO | WO 2004/003019 | 1/2004 |
| WO | WO 2004/010951 | 2/2004 |
| WO | WO 2004/035607 | 4/2004 |
| WO | WO 2004/099249 | 11/2004 |
| WO | WO 2005/018572 | 3/2005 |
| WO | WO 2005/062916 | 7/2005 |
| WO | WO 2005/063815 | 7/2005 |
| WO | WO 2005/118635 | 12/2005 |
| WO | WO 2006/020114 | 2/2006 |
| WO | WO 2006/105338 | 10/2006 |
| WO | WO 2006/106903 | 10/2006 |
| WO | WO 2006/106905 | 10/2006 |
| WO | WO 2006/109592 | 10/2006 |
| WO | WO 2007/041635 | 4/2007 |
| WO | WO 2007/053659 | 5/2007 |
| WO | WO 2007/110205 | 10/2007 |
| WO | WO 2007/114325 | 10/2007 |
| WO | WO 2007/141280 | 12/2007 |
| WO | WO 2007/145941 | 12/2007 |
| WO | WO 2007/147901 | 12/2007 |
| WO | WO 2008/090960 | 7/2008 |
| WO | WO 2008/119353 | 10/2008 |
| WO | WO 2008/119567 | 10/2008 |
| WO | WO 2008/145142 | 12/2008 |
| WO | WO 2009/011941 | 1/2009 |
| WO | WO 2009/041613 | 4/2009 |
| WO | WO 2009/053368 | 4/2009 |
| WO | WO 2009/080252 | 7/2009 |
| WO | WO 2009/080253 | 7/2009 |
| WO | WO 2009/089004 | 7/2009 |
| WO | WO 2009/120922 | 10/2009 |
| WO | WO 2009/125825 | 10/2009 |
| WO | WO 2009/134776 | 11/2009 |
| WO | WO 2010/034441 | 4/2010 |
| WO | WO 2010/085682 | 7/2010 |
| WO | WO 2010/102251 | 9/2010 |
| WO | WO 2010/106180 | 9/2010 |
| WO | WO 2010/107109 | 9/2010 |
| WO | WO 2010/115589 | 10/2010 |
| WO | WO 2010/120561 | 10/2010 |
| WO | WO 2010/129304 | 11/2010 |
| WO | WO 2010/131733 | 11/2010 |
| WO | WO 2010/151792 | 12/2010 |
| WO | WO 2011/108502 | 9/2011 |
| WO | WO 2011/108714 | 9/2011 |
| WO | WO 2011/131746 | 10/2011 |
| WO | WO 2011/133886 | 10/2011 |
| WO | WO 2011/143545 | 11/2011 |
| WO | WO 2011/147986 | 12/2011 |
| WO | WO 2012/020096 | 2/2012 |
| WO | WO 2012/067176 | 5/2012 |

(56) References Cited

FOREIGN PATENT DOCUMENTS

| | | |
|---|---|---|
| WO | WO 2012/073985 | 6/2012 |
| WO | WO 2012/131555 | 10/2012 |
| WO | WO 2013/060867 | 5/2013 |
| WO | WO 2013/065708 | 5/2013 |
| WO | WO 2013/124450 | 8/2013 |
| WO | WO 2013/157954 | 10/2013 |
| WO | WO 2014/054804 | 4/2014 |
| WO | WO 2014/067011 | 5/2014 |
| WO | WO 2015/046467 | 4/2015 |
| WO | WO 2016/159213 | 10/2016 |
| WO | WO 2019/131988 | 7/2019 |
| WO | WO 2021/201202 | 10/2021 |

OTHER PUBLICATIONS

Karshtedt et al.(Hastings Sci. & Tech. L J, 3(1): 109-155 (2011)).*
Amann et al., "Therapeutic window of an EpCAM/CD3-specific BiTE antibody in mice is determined by a subpopulation of EpCAM-expressing lymphocytes that is absent in humans," *Cancer Immunol Immunother,* Jan. 2009; 58(1):95-109. Epub Jul. 2, 2008.
Armour et al., "Recombinant human IgG molecules lacking Fcgamma receptor I binding and monocyte triggering activities," *Eur J Immunol.,* 29(8):2613-24 (1999).
Bargou et al., "Tumor regression in cancer patients by very low doses of a T cell-engaging antibody," *Science,* 321(5891):974-7 (2008).
Bokemeyer, "Catumaxomab—trifunctional anti-EpCAM antibody used to treat malignant ascites," *Expert Opin Biol Ther.,* 10(8):1259-69 (2010).
Campoli et al., "Immunotherapy of malignant disease with tumor antigen-specific monoclonal antibodies," *Clin Cancer Res.,* Jan. 1, 2010;16(1):11-20. Epub Dec. 22, 2009.
Kufer et al., "A revival of bispecific antibodies," *Trends Biotechnol.,* 22(5):238-44 (2004).
Kumagai et al., "Humanized bispecific antibodies that recognize lymphocytes and cancer cells," *Drug Delivery System,* 23(5):518-25 (2008) (English translation).
Mack et al., "A small bispecific antibody construct expressed as a functional single-chain molecule with high tumor cell cytotoxicity," *Proc Natl Acad Sci U S A,* 92(15):7021-5 (1995).
McEarchern et al., "Engineered anti-CD70 antibody with multiple effector functions exhibits in vitro and in vivo antitumor activities," *Blood,* Feb. 1, 2007;109(3):1185-92. Epub Oct. 12, 2006.
Merchant et al., "An efficient route to human bispecific IgG," *Nat Biotechnol.,* 16(7):677-81 (1998).
Mezzanzanica et al., "Human ovarian carcinoma lysis by cytotoxic T cells targeted by bispecific monoclonal antibodies: analysis of the antibody components," *Int J Cancer,* 41(4):609-15 (1988).
Molhoj et al., "CD19-/CD3-bispecific antibody of the BiTE class is far superior to tandem diabody with respect to redirected tumor cell lysis," *Mol Immunol.,* 44(8):1935-43 (2007).
Nakano et al., "Anti-glypican 3 antibodies cause ADCC against human hepatocellular carcinoma cells," *Biochem Biophys Res Commun.,* Jan. 9, 2009;378(2):279-84. doi: 10.1016/j.bbrc.2008.11.033. Epub Nov. 18, 2008.
Natsume et al., "Improving effector functions of antibodies for cancer treatment: Enhancing ADCC and CDC," *Drug Des Devel Ther.,* 3:7-16 (2009).
Padlan et al., "Antibody Fab assembly: the interface residues between CH1 and CL," *Mol Immunol.,* 23(9):951-60 (1986).
Presta, "Molecular engineering and design of therapeutic antibodies," *Curr Opin Immunol.,* Aug. 2008;20(4):460-70. doi: 10.1016/j.coi.2008.06.012.
Ridgway et al., "Knobs-into-holes' engineering of antibody CH3 domains for heavy chain heterodimerization," *Protein Eng.,* 9(7):617-21 (1996).
Rothlisberger et al., "Domain interactions in the Fab fragment: a comparative evaluation of the single-chain Fv and Fab format engineered with variable domains of different stability," *J Mol Biol.,* 347(4):773-89 (2005).
Schlereth et al., "T-cell activation and B-cell depletion in chimpanzees treated with a bispecific anti-CD19/anti-CD3 single-chain antibody construct," *Cancer Immunol Immunother.,* May 2006;55(5):503-14. Epub Jul. 20, 2005.
Sebastian et al., "Treatment of non-small cell lung cancer patients with the trifunctional monoclonal antibody catumaxomab (anti-EpCAM x anti-CD3): a phase I study," *Cancer Immunol Immunother.,* 56(10):1637-44 (2007).
Segal et al., "Bispecific antibodies in cancer therapy," *Curr Opin Immunol.,* 11(5):558-62 (1999).
Seimetz et al., "Development and approval of the trifunctional antibody catumaxomab (anti-EpCAM x anti-CD3) as a targeted cancer immunotherapy," *Cancer Treat Rev.,* 36(6):458-67 (2010).
Staerz et al., "Hybrid antibodies can target sites for attack by T cells," *Nature,* 314(6012):628-31 (1985).
Staerz et al., "Hybrid hybridoma producing a bispecific monoclonal antibody that can focus effector T-cell activity," *Proc Natl Acad Sci U.S.A.,* 83:1453-7 (1986).
Stroehlein et al., "Induction of anti-tumor immunity by trifunctional antibodies in patients with peritoneal carcinomatosis," *J Exp Clin Cancer Res.,* Feb. 14, 2009;28:18. doi: 10.1186/1756-9966-28-18.
Suzuki, "Research and Development of Antibody Pharmaceuticals," *NIBS LETTER,* 56(4):45-51 (2010) (English translation).
Teerinen et al., "Structure-based stability engineering of the mouse IgG1 Fab fragment by modifying constant domains," *J Mol Biol.,* 361(4):687-97 (2006).
Thakur et al., "Cancer therapy with bispecific antibodies: Clinical experience," *Curr Opin Mol Ther.,* 12(3):340-9 (2010).
Wolf et al., "BiTEs: bispecific antibody constructs with unique anti-tumor activity," *Drug Discov Today,* 10(18):1237-44 (2005).
International Search Report for App. Ser. No. PCT/JP2012/078103, mailed Jan. 22, 2013, 6 pages.
International Preliminary Report on Patentability for App. Ser. No. PCT/JP2012/078103, dated May 6, 2014, 6 pages.
International Preliminary Report on Patentability for App. Ser. No. PCT/JP2011/077603, dated Jun. 4, 2013, 10 pages.
International Search Report for App. Ser. No. PCT/JP2011/077603, mailed Mar. 13, 2012, 8 pages.
Klein et al., "Progress in overcoming the chain association issue in bispecific heterodimeric IgG antibodies," *mAbs* 4(6):653-63, 2012. doi: 10.4161/mabs.21379. Epub Aug. 27, 2012.
Griffin et al., "Analysis of heavy and light chain sequences of conventional camelid antibodies from Camelus dromedarius and Camelus bactrianus species," *J Immunol Methods,* Mar. 2014;405:35-46. doi: 10.1016/j. jim.2014.01.003. Epub Jan. 18, 2014.
Hamers-Casterman et al., "Naturally occurring antibodies devoid of light chains," *Nature,* Jun. 3, 1993;363(6428):446-8.
Igawa et al., "VH/VL interface engineering to promote selective expression and inhibit conformational isomerization of thrombopoietin receptor agonist single-chain diabody," *Protein Eng Des Sel.,* Aug. 2010;23(8):667-77. doi: 10.1093/protein/gzq034. Epub Jun. 24, 2010.
Marvin et al., "Recombinant approaches to IgG-like bispecific antibodies," *Acta. Pharmacol. Sin.,* Jun. 2005;26:649-58.
O'Shea et al., "Peptide 'Velcro': design of a heterodimeric coiled coil," *Curr Biol.,* Oct. 1, 1993;3(10):658-67.
Raffen et al., "Reengineering immunoglobulin domain interactions by introduction of charged residues," *Protein Eng.* Apr. 1998;11:303-9.
Ruf et al., "Induction of a long-lasting antitumor immunity by a trifunctional bispecific antibody," *Blood,* Oct. 15, 2001;98(8):2526-34.
Wang et al., "Conserved amino acid networks involved in antibody variable domain interactions," *Proteins,* Jul. 2009;76(1):99-114. doi: 10.1002/prot.22319.
Edelman et al., "The covalent structure of an entire gammaG immunoglobulin molecule," *Proc Natl Acad Sci U S A.,* May 1969;63(1):78-85.
Johnson et al., "Kabat database and its applications: 30 years after the first variability plot," *Nucleic Acids Res.,* Jan. 1, 2000;28(1):214-8.
Kabat et al., Sequence of Proteins of Immunological Interest, 5$^{th}$ Edition 1991, p. 690 and p. 693.

(56) References Cited

OTHER PUBLICATIONS

Zhu et al., "Remodeling domain interfaces to enhance heterodimer formation," *Protein Sci.*, Apr. 1997;6(4):781-8.
Gramer et al., "Production of stable bispecific IgG1 by controlled Fab-arm exchange: scalability from bench to large-scale manufacturing by application of standard approaches," *MAbs.*, Nov.-Dec. 2013;5(6):962-73. doi: 10.4161/mabs.26233. Epub Aug. 22, 2013.
Labrijn et al., "Species-specific determinants in the IgG CH3 domain enable Fab-arm exchange by affecting the noncovalent CH3-CH3 interaction strength," *J Immunol.*, Sep. 15, 2011;187(6):3238-46. doi: 10.4049/jimmunol.1003336. Epub Aug. 12, 2011.
Labrijn et al., "Efficient generation of stable bispecific IgG1 by controlled Fab-arm exchange," *Pro Natl Acad Sci U S A.*, Mar. 26, 2013;110(13):5145-50. doi: 10.1073/pnas.1220145110. Epub Mar. 11, 2013.
McPhee et al., "Engineering human immunodeficiency virus 1 protease heterodimers as macromolecular inhibitors of viral maturation," *Proc Natl Acad Sci U S A.*, Oct. 15, 1996;93(21):11477-81.
Pavlou et al., "The therapeutic antibodies market to 2008," *Eur. J. Pharm. Biopharm.*, Apr. 2005;59:389-396.
Reichert et al., "Monoclonal antibody successes in the clinic," *Nat. Biotechnol.*, Sep. 2005;23:1073-7.
Rispens et al., "Dynamics of inter-heavy chain interactions in human immunoglobulin G (IgG) subclasses studied by kinetic Fab arm exchange," *J Biol Chem.*, Feb. 28, 2014;289(9):6098-109. doi: 10.1074/jbc.M113.541813. Epub Jan. 14, 2014.
Schaefer et al., "Immunoglobulin domain crossover as a generic approach for the production of bispecific IgG antibodies," *Proc Natl Acad Sci U S A.*, Jul. 5, 2011;108(27):11187-92. doi: 10.1073/pnas.1019002108. Epub Jun. 20, 2011.
Schuurman et al., "Normal human immunoglobulin G4 is bispecific: it has two different antigen-combining sites," *Immunology*, Aug. 1999;97(4):693-8.
Schuurman et al., "The inter-heavy chain disulfide bonds of IgG4 are in equilibrium with intra-chain disulfide bonds," *Mol Immunol.*, Jan. 2001;38(1):1-8.
Van Der Neut Kolfschoten et al., "Anti-inflammatory activity of human IgG4 antibodies by dynamic Fab arm exchange," *Science*, Sep. 14, 2007;317(5844):1554-7.
Ward et al., "Effects of engineering complementary charged residues into the hydrophobic subunit interface of tyrosyl-tRNA synthetase. Appendix: Kinetic analysis of dimeric enzymes that reversibly dissociate into inactive subunits," *Biochemistry*, Jun. 30, 1987;26(13):4131-8.
Arndt et al., "Factors influencing the dimer to monomer transition of an antibody single-chain Fv fragment" *Biochemistry*, Sep. 15, 1998;37(37):12918-26.
Asano et al., "Highly effective recombinant format of a humanized IgG-like bispecific antibody for cancer immunotherapy with retargeting of lymphocytes to tumor cells," *J Biol Chem.*, Sep. 21, 2007;282(38):27659-65. Epub Jul. 19, 2007.
Aslan et al., "Engineering a novel, stable dimeric streptavidin with lower isoelectric point," *J Biotechnol.*, Feb. 1, 2007;128(2):213-25. Epub Sep. 26, 2006.
Atwell et al., "Stable heterodimers from remodeling the domain interface of a homodimer using a phage display library," *J Mol Biol.*, Jul. 4, 1997;270(1):26-35.
Baerga-Ortiz et al., "Two different proteins that compete for binding to thrombin have opposite kinetic and thermodynamic profiles," *Protein Sci.*, Jan. 2004;13(1):166-76.
Carter, "Bispecific human IgG by design," *J Immunol Methods*, Feb. 1, 2001;248(1-2):7-15.
Chatellier et al., "Functional mapping of conserved residues located at the VL and VH domain interface of a Fab," *J Mol Biol.*, Nov. 22, 1996;264(1):1-6.
Choi et al., "Engineering of Immunoglobulin Fc Heterodimers Using Yeast Surface-Displayed Combinatorial Fc Library Screening," *PLoS One*, Dec. 16, 2015;10(12):e0145349. doi: 10.1371/journal.pone.0145349. eCollection 2015.

Dall'Acqua et al., "Modulation of the effector functions of a human IgG1 through engineering of its hinge region," *J Immunol.*, Jul. 15, 2006;177(2):1129-38.
Davies et al., "Antibody VH domains as small recognition units," *Biotechnology (N Y)*, May 1995;13(5):475-9.
Gunasekaran et al., "Enhancing antibody Fc heterodimer formation through electrostatic steering effects: applications to bispecific molecules and monovalent IgG," *J Biol Chem.*, Jun. 18, 2010;285(25):19637-46. doi: 10.1074/jbc.M110.117382. Epub Apr. 16, 2010.
Jung et al., "The importance of framework residues H6, H7 and H10 in antibody heavy chains: experimental evidence for a new structural subclassification of antibody V(H) domains," *J Mol Biol.*, Jun. 8, 2001;309(3):701-16.
Kipriyanov et al., "Effect of domain order on the activity of bacterially produced bispecific single-chain Fv antibodies," *J Mol Biol.*, Jun. 27, 2003;330(1):99-111.
Kipriyanov et al., "Bispecific tandem diabody for tumor therapy with improved antigen binding and pharmacokinetics," *J Mol Biol.*, Oct. 15, 1999;293(1):41-56.
Khalifa et al., "Bispecific tandem diabody for tumor therapy with improved antigen binding and pharmacokinetics," *J Mol. Recognit.*, May-Jun. 2000;13(3):127-39.
Kontermann, "Recombinant bispecific antibodies for cancer therapy," *Acta Pharmacol Sin.*, Jan. 2005;26(1):1-9.
Korn et al., "Recombinant bispecific antibodies for the targeting of adenoviruses to CEA-expressing tumour cells: a comparative analysis of bacterially expressed single-chain diabody and tandem scFv," *J Gene Med.*, Jun. 2004;6(6):642-51.
Kumar et al., "The second PDZ domain of INAD is a type I domain involved in binding to eye protein kinase C. Mutational analysis and naturally occurring variants," *J Biol Chem.*, Jul. 6, 2001;276(27):24971-7. Epub May 7, 2001.
Kumar et al., "Molecular cloning and expression of the Fabs of human autoantibodies in *Escherichia coli*. Determination of the heavy or light chain contribution to the anti-DNA/-cardiolipin activity of the Fab," *J Biol Chem.*, Nov. 10, 2000;275(45):35129-36.
Kurfis et al., "Role of Arg182 in the second extracellular loop of angiotensin II receptor AT2 in ligand binding," *Biochem Biophys Res Commun.*, Oct. 5, 1999;263(3):816-9.
Le Gall et al., "Effect of linker sequences between the antibody variable domains on the formation, stability and biological activity of a bispecific tandem diabody," *Protein Eng Des Sel.*, Apr. 2004;17(4):357-66. Epub May 4, 2004.
Liu et al., "Functional interactions between arginine-133 and aspartate-88 in the human reduced folate carrier: evidence for a charge-pair association," *Biochem J.*, Sep. 1, 2001;358(Pt 2):511-6.
Maity et al., "Equilibrium unfolding of dimeric and engineered monomeric forms of lambda Cro (F58W) repressor and the effect of added salts: evidence for the formation of folded monomer induced by sodium perchlorate," *Arch Biochem Biophys.*, Feb. 1, 2005;434(1):93-107.
Marti et al., "Inverse electrostatic effect: electrostatic repulsion in the unfolded state stabilizes a leucine zipper," *Biochemistry*, Oct. 5, 2004;43(39):12436-47.
Marvin et al., "Redesigning an antibody fragment for faster association with its antigen," *Biochemistry*, Jun. 17, 2003;42(23):7077-83.
Narhi et al., "Asn to Lys mutations at three sites which are N-glycosylated in the mammalian protein decrease the aggregation of *Escherichia coli*-derived erythropoietin," *Protein Eng.*, Feb. 2001;14(2):135-40.
Nieba et al., "Disrupting the hydrophobic patches at the antibody variable/constant domain interface: improved in vivo folding and physical characterization of an engineered scFv fragment," *Protein Eng.*, Apr. 1997;10(4):435-44.
Nohaile et al., "Altering dimerization specificity by changes in surface electrostatics," *Proc Natl Acad Sci U S A.*, Mar. 13, 2001;98(6):3109-14. Epub Feb. 27, 2001.
Pokkuluri et al., "A domain flip as a result of a single amino-acid substitution," *Structure*, Aug. 15, 1998;6(8):1067-73.
Queen et al., "A humanized antibody that binds to the interleukin 2 receptor," *Proc Natl Acad Sci U S A.*, Dec. 1989;86(24):10029-33.

(56) References Cited

OTHER PUBLICATIONS

Sal-Man et al., "Arginine mutations within a transmembrane domain of Tar, an *Escherichia coli* aspartate receptor, can drive homodimer dissociation and heterodimer association in vivo," Biochem J., Jan. 1, 2005;385(Pt 1):29-36.
Salfeld, "Isotype selection in antibody engineering," Nat Biotechnol., Dec. 2007;25(12):1369-72.
Sinha et al., "Electrostatics in protein binding and function," Curr Protein Pept Sci., Dec. 2002;3(6):601-14.
Smith-Gill et al., "Contributions of immunoglobulin heavy and light chains to antibody specificity for lysozyme and two haptens," J Immunol., Dec. 15, 1987;139(12):4135-44.
Song et al., "Light chain of natural antibody plays a dominant role in protein antigen binding," Biochem Biophys Res Commun., Feb. 16, 2000;268(2):390-4.
Tan et al., "Contributions of a highly conserved VH/VL hydrogen bonding interaction to scFv folding stability and refolding efficiency," Biophys J., Sep. 1998;75(3):1473-82.
Vargas-Madrazo et al., "An improved model of association for VH-VL immunoglobulin domains: asymmetries between VH and VL in the packing of some interface residues," J Mol Recognit., May-Jun. 2003;16(3):113-20.
Ward et al., "Binding activities of a repertoire of single immunoglobulin variable domains secreted from *Escherichia coli*," Nature, Oct. 12, 1989;341(6242):544-6.
Worn et al., "Stability engineering of antibody single-chain Fv fragments," J Mol Biol., Feb. 2, 2001;305(5):989-1010.
Wu et al., "Multimerization of a chimeric anti-CD20 single-chain Fv-Fc fusion protein is mediated through variable domain exchange," Protein Eng., Dec. 2001;14(12):1025-33.
Paul et al., "Immunologiya", M.:Mir, 1987-1988, vol. 1, p. 231 (with English translation).
Pritsch et al., "Can Immunoglobulin CH1 Constant Region Domain Modulate Antigen Binding Affinity of Antibodies?," J Clin Invest. Nov. 15, 1996;98(10):2235-43.
Diaz et al., "Effects of engineering charged amino acids in the CH3 domains on antibody heavy chain dimerization," Philippine Science Letters. 2011;4(1):48-55.
Spiess et al., "Bispecific antibodies with natural architecture produced by co-culture of bacteria expressing two distinct half-antibodies," Nat Biotechnol. Aug. 1, 2013;31(8):753-8. doi: 10.1038/nbt.2621. Epub Jul, 7. 2013.
U.S. Appl. No. 15/782,256, Igawa et al., filed Sep. Oct. 12, 2017.
Bowie et al., "Deciphering the Message in Protein Sequences: Tolerance to Amino Acid Substitutions," Science, 247 (4948): 1306-1310, Mar. 16, 1990.
Golay et al., "Mechanism of action of therapeutic monoclonal antibodies: Promises and pitfalls of in vitro and in vivo assays" Archives of Biochemistry and Biophysics 526: 146-153, Feb. 25, 2012.
Hattori, Introduction of ART-Ig and application to hemophilia A treatment, Chugai Seiyaku ni Okeru Dokuji no Kakushinteki Kotai Gijutsu. Dec. 2012; 18: 42-57 (with English translation).
Labrijn et al., "Controlled Fab-arm exchange for the generation of stable bispecific IgG1," Nat Protoc. Oct. 2014; 9(10): 2450-63. doi: 10.1038/nprot.2014.169. Epub Sep. 25, 2014.
Peters et al., "Engineering an improved IgG4 molecule with reduced disulfide bond heterogeneity and increased Fab domain thermal stability," J Biol Chem. Jul. 13, 2012; 287(29): 24525-33. doi: 10.1074/jbc.M112.369744. Epub May 18, 2012.
Shields et al., "High resolution mapping of the binding site on human IgG1 for Fc gamma RI, Fc gamma RII, Fc gamma RIII, and FcRn and design of IgG1 variants with improved binding to the Fc gamma R," J. Biol. Chem., 276:6591-6604 (Mar. 2, 2001) (Epub Nov. 28, 2000).
Stancovski et al., "Mechanistic Aspects of the Opposing Effects of Monoclonal Antibodies to the ERBB2 Receptor on Tumor Growth," Proc Nat Acad Sci USA 88:8691-8695, Oct. 1991.
Wines et al., "The IgG Fc contains distinct Fc receptor (FcR) binding sites: the leukocyte receptors Fc gamma RI and Fc gamma RIIa bind to a region in the Fc distinct from that recognized by neonatal FcR and protein A," J Immunol. May 15, 2000; 164(10):5313-8.
Zeidler et al., "Simultaneous Activation of T Cells and Accessory Cells by a New Class of Intact Bispecific Antibody Results in Efficient Tumor Cell Killing," J Immunol. Aug. 1, 1999; 163(3): 1246-52.
USPTO Restriction Requirement in U.S. Appl. No. 13/990,088, dated Nov. 27, 2015, 9 pages.
USPTO Office Action in U.S. Appl. No. 13/990,088, dated Apr. 29, 2016, 33 pages.
USPTO Final Office Action in U.S. Appl. No. 13/990,088, dated Nov. 25, 2016, 30 pages.
USPTO Non-Final Office Action in U.S. Appl. No. 13/990,088, dated Aug. 21, 2017, 16 pages.
U.S. Pat. No. 10,011,858, Igawa et al., issued Jul. 3, 2018, 2008.
U.S. Appl. No. 15/024,063, Igawa et al., filed Mar. 23, 2016.
U.S. Appl. No. 13/990,088, Nezu et al., filed Dec. 19, 2013.
Jaeger, "Clinical Immunology and Allergology," 2nd edition, M.: Medicina, 1990, 2:484-5, 7 pages (with English translation).
Sampei et al., "Non-antigen-contacting region of an asymmetric bispecific antibody to factors IXa/X significantly affects factor VIII-mimetic activity," mAbs, Jan./Feb. 2015, 7(1):120-8. doi: 10.4161/19420862.2015.989028.
Yarilin, "Immunology Basics," M.: Medicina, 1999, 169-74, 14 pages (with English translation).
USPTO Final Office Action in U.S. Appl. No. 13/990,088, dated Mar. 21, 2018, 19 pages.
USPTO Applicant-Initiated Interview Summary in U.S. Appl. No. 13/990,088, dated Aug. 10, 2018, 6 pages.
USPTO Non-Final Office Action in U.S. Appl. No. 13/990,088, dated Oct. 1, 2018, 26 pages.
Moiseenko, "Monoclonal Antibodies in the Treatment of Malignant Tumors," Practical Oncology, 2003, 4(3):148-56 (with English translation).
Choi et al., "Crystal structures of immunoglobulin Fc heterodimers reveal the molecular basis for heterodimer formation," Mol Immunol, Jun. 2015, 65(2):377-83. doi: 10.1016/j.molimm. 2015.02.017. Epub Mar. 2, 2015.
De Gast et al., "CD8 T cell activation after intravenous administration of CD3 x CD19 bispecific antibody in patients with non-Hodgkin lymphoma," Cancer Immunol Immunother, Jun. 1995, 40(6):390-6.
Dillon et al., "Structural and Functional Characterization of Disulfide Isoforms of the Human IgG2 Subclass," J Biol Chem, Jun. 6, 2008, 283(23):16206-15. Epub Mar. 12, 2008.
Feige et al., "How antibodies fold," Trends Biochem Sci, Apr. 2010, 35(4):189-98. doi: 10.1016/j.tibs.2009.11.005. Epub Dec. 21, 2009.
Feige et al., "An Unfolded $C^H1$ Domain Controls the Assembly and Secretion of IgG Antibodies," Mol Cell, Jun. 12, 2009, 34(5):569-79. doi: 10.1016/J.molcel.2009.04.028.
Goulet et al., "Kinetic mechanism of controlled Fab-arm exchange for the formation of bispecific immunoglobulin G1 antibodies," J Biol Chem, Jan. 12, 2018, 293(2):651-661. doi: 10.1074/jbc.RA117.000303. Epub Nov. 17, 2017.
Horne et al., "Noncovalent association of heavy and light chains of human immunoglobulins. III. Specific interactions between VH and VL," J Immunol, Aug. 1982, 129(2):660-4.
Kabat et al., "Sequences of proteins of immunological interest," Diane Publishing, 1991, pp. 647-652 and 661-669.
Lazar et al., "Engineered antibody Fc variants with enhanced effector function," Proc Natl Acad Sci USA, Mar. 14, 2006, 103(11):4005-10. Epub Mar. 6, 2006.
Muller et al., "The first constant domain ($C_H1$ and $C_L$) of an antibody used as heterodimerization domain for bispecific miniantibodies," FEBS Lett, Jan. 30, 1998, 422(2):259-64.
Rispens et al., "Mechanism of Immunoglobulin G4 Fab-arm Exchange," J Am Chem Soc, Jul. 6, 2011, 133(26):10302-11. doi: 10.1021/ja203638y. Epub Jun. 15, 2011.
Wang et al., "A New Recombinant Single Chain Trispecific Antibody Recruits T Lymphocytes to Kill CEA (Carcinoma Embryonic Antigen) Positive Tumor Cells In Vitro Efficiently," J Biochem, Apr. 2004, 135(4):555-65.

(56) References Cited

OTHER PUBLICATIONS

Zeidler et al., "The Fc-region of a new class of intact bispecific antibody mediates activation of accessory cells and NK cells and induces direct phagocytosis of tumour cells," Br J Cancer, Jul. 2000, 83(2):261-6.
Chandramohan et al., "Antibody, T-cell and dendritic cell immunotherapy for malignant brain tumors," Future Oncol, Jul. 2013, 9(7):977-90. doi: 10.2217/fon.13.47.
Fischer et al., "Bispecific Antibodies: Molecules That Enable Novel Therapeutic Strategies," Pathobiology, 2007, 74(1):3-14.
Li et al., "Construction and characterization of a humanized anti-human CD3 monoclonal antibody 12F6 with effective immunoregulation functions," Immunology, Dec. 2005, 116(4):487-98.
Wing et al., "Mechanism of First-Dose Cytokine-Release Syndrome by CAMPATH 1-H: Involvement of CD16 (FcγRIII) and CD11a/CD18 (LFA-1) on NK Cells," J Clin Invest, Dec. 15, 1996, 98(12):2819-26.
USPTO Final Office Action in U.S. Appl. No. 13/990,088, dated Jun. 5, 2019, 15 pages.
Bodelon et al., "Immunoglobulin domains in *Escherichia coli* and other enterobacteria: from pathogenesis to applications in antibody technologies," FEMS Microbiol Rev, Mar. 2013, 37(2):204-50. doi: 10.1111/j.1574-6976.2012.00347.x., Epub Jul. 23, 2012.
InvivoGen, "Review: Immunoglobulin G," 2011, 1 page (downloaded on Jul. 1, 2019 from www.invivogen.com/sites/default/files/invivogen/old/docs/reviews/review-ImmunoglobulinG-invivogen.pdf).
Alignment of Fc domain sequences of catumaxomab and SEQ ID Nos.: 23, 24, 25 and 26 (cited in oppositions filed against European No. 2 647 707 on May 31, 2019 and Jun. 12, 2019), 2 pages.
An et al., "IgG2m4, an engineered antibody isotype with reduced Fc function," mAbs, Nov.-Dec. 2009, 1(6):572-9.
Aschermann et al., "The other side of immunoglobulin G: suppressor of inflammation," Clin Exp Immunol, May 2010, 160(2):161-7. doi: 10.1111/j.1365-2249.2009.04081.x. Epub Dec. 16, 2009.
Brennan et al., "Safety and immunotoxicity assessment of immunomodulatory monoclonal antibodies," mAbs, May-Jun. 2010, 2(3):233-55. Epub May 23, 2010.
Chelius et al., "Structural and functional characterization of the trifunctional antibody catumaxomab," mAbs, May-Jun. 2010, 2(3):309-19. Epub May 16, 2010.
Copy of Annex 1, submitted by the patentee during examination proceedings on Sep. 18, 2015 (cited in oppositions filed against European Patent No. 2 647 707 on May 31, 2019 and Jun. 12, 2019), 5 pages.
Das et al., "Producing Bispecific and Bifunctional Antibodies," Methods Mol Med, 2005, 109:329-46.
Demanet et al., "Treatment of murine B cell lymphoma with bispecific monoclonal antibodies (anti-idiotype x anti-CD3)," J Immunol, Aug. 1, 1991, 147(3):1091-7.
English translation of EP 11845786 as filed (cited in oppositions filed against European Patent No. 2 647 707 on May 31, 2019 and Jun. 12, 2019), 123 pages.
Graca, The Immune Synapse as a Novel Target for Therapy, 2008, pp. 59-61.
Haagen et al., "Evaluation of Fcγ receptor mediated T-cell activation by two purified CD3 x CD19 bispecific monoclonal antibodies with hybrid Fc domains," Ther Immunol, Oct. 1994, 1(5):279-87.
Haagen et al., "Interaction of human monocyte Fc gamma receptors with rat IgG2b. A new indicator for the FC gamma RIIa (R-H131) polymorphism," J Immunol, Feb. 15, 1995, 154(4):1852-60.
Hezareh et al., "Effector Function Activities of a Panel of Mutants of a Broadly Neutralizing Antibody against Human Immunodeficiency Virus Type 1," J Virol, Dec. 2001, 75(24):12161-8.
Hinton et al., "An Engineered Human IgG1 Antibody with Longer Serum Half-Life," J Immunol, Jan. 1, 2006, 176(1):346-56.
Hoseini et al., "Immunotherapy of hepatocellular carcinoma using chimeric antigen receptors and bispecific antibodies," Cancer Lett, Jul. 28, 2017, 399:44-52. doi: 10.1016/j.canlet.2017.04.013. Epub Apr. 17, 2017.
Ishiguro et al., "An anti-glypican 3/CD3 bispecific T cell-redirecting antibody for treatment of solid tumors," Sci Transl Med, Oct. 4, 2017, 9(410). pii: eaa14291. doi:10.1126/scitranslmed.aa14291.
Kasthuri et al., "Role of Tissue Factor in Cancer," J Clin Oncol, Oct. 10, 2009, 27(29):4834-8. doi: 10.1200/JCO.2009.22.6324. Epub Sep. 8, 2009.
King, Applications and Engineering of Monoclonal Antibodies, 2005, pp. 146-147.
Kontermann, "The Role of the Fc Region," Bispecific Antibodies, 2011, 296-8.
Link et al., "Anti-CD-3-Based Bispecific Antibody Designed for Therapy of Human B-Cell Malignancy Can Induce T-Cell Activation by Antigen-Dependent and Antigen-Independent Mechanisms," Int J Cancer, Jul. 17, 1998, 77(2):251-6.
Little, Recombinant Antibodies for Immunotherapy, 2009, pp. 133-134.
Matzku et al., Antibodies in Diagnosis and Therapy; Technologies, Mechanisms and Clinical Data, 1999, p. 7.
Milstein et al., "Hybrid hybridomas and their use in immunohistochemistry," Nature, Oct. 6-12, 1983, 305(5934):537-40.
Nelson et al., "5.2 Complementary Interactions between Proteins and Ligands: The Immune System and Immunoglobulins," Lehninger, Principles of Biochemistry, 5th Ed., 2008, p. 171.
Nimmerjahn et al., "Fcγ receptors as regulators of immune responses," Nat Rev Immunol, Jan. 2008, 8(1):34-47.
Nitta et al., "Bispecific F(ab')$_2$ monomer prepared with anti-CD3 and anti-tumor monoclonal antibodies is most potent in induction of cytolysis of human T cells," Eur J Immunol, Aug. 1989, 19(8):1437-41.
Oganesyan et al., "Structural characterization of a human Fc fragment engineered for lack of effector functions," Acta Crystallogr D Biol Crystallogr, Jun. 2008, 64(Pt 6):700-4. doi: 10.1107/S0907444908007877. Epub May 14, 2008.
Parren et al., "Induction of T-cell proliferation by recombinant mouse and chimeric mouse/human anti-CD3 monoclonal antibodies," Res Immunol, Nov.-Dec. 1991, 142(9):749-63.
Ravetch et al., "Fc Receptors," Annu Rev Immunol, Apr. 1991, 9:457-92.
Routledge et al., "A humanized monovalent CD3 antibody which can activate homologous complement," Eur J Immunol, Nov. 1991, 21 (11):2717-25.
Salnikov et al., "Targeting of cancer stem cell marker EpCAM by bispecific antibody EpCAMxCD3 inhibits pancreatic carcinoma," J Cell Mol Med, Sep. 2009, 13(9B):4023-33. doi: 10.1111/j.1582-4934.2009.00723.x.
Segal et al., "Production of Bispecific Antibodies," Current Protocols in Immunology, 1995, Unit 2.13.1- 2.13.16.
Sequence Alignments (cited in oppositions filed against European Patent No. 2 647 707 on May 31, 2019 and Jun. 12, 2019), 6 pages.
Strauss et al., "Without Prior Stimulation, Tumor-associated Lymphocytes from Malignant Effusions Lyse Autologous Tumor Cells in the Presence of Bispecific Antibody HEA125xOKT3," Clin Cancer Res, Jan. 1999, 5(1):171-80.
Strohl, "Optimization of Fc-mediated effector functions of monoclonal antibodies," Curr Opin Biotechnol, Dec. 2009, 20(6):685-91. doi:10.1016/j.copbio.2009.10.011. Epub Nov. 4, 2009.
Van Loghem et al., "Staphylococcal Protein A and Human IgG Subclasses and Allotypes," Scand J Immunol, Mar. 1982, 15(3):275-8.
Xu et al., "In Vitro Characterization of Five Humanized OKT3 Effector Function Variant Antibodies," Cell Immunol, Feb. 25, 2000, 200(1):16-26.
Labrijn et al., "Therapeutic IgG4 antibodies engage in Fab-arm exchange with endogenous human IgG4 in vivo," Nat Biotechnol, Aug. 2009, 27(8):767-771.
Lund et al., "Multiple Interactions of IgG with Its Core Oligosaccharide Can Modulate Recognition by Complement and Human Fcγ Receptor I and Influence the Synthesis of Its Oligosaccharide Chains," The Journal of Immunology, Dec. 1996, 157(11):4963-4969.

(56) References Cited

OTHER PUBLICATIONS

Wu et al., "Humanization of a Murine Monoclonal Antibody by Simultaneous Optimization of Framework and CDR Residues," J Mol Biol, Nov. 19, 1999, 294(1):151-162.
USPTO Advisory Action in U.S. Appl. No. 13/990,088, dated Oct. 23, 2019, 3 pages.
USPTO AFCP 2.0 Decision in U.S. Appl. No. 13/990,088, dated Oct. 23, 2019, 2 pages.
U.S. Appl. No. 61/467,727, Blein et al., filed Mar. 25, 2011.
Annex 1—Analysis of the Examples of EP 2 787 078 (document cited in opposition of EP 2 787 078 on Feb. 28, 2020).
Arguments filed on Oct. 12, 2016 in U.S. App. U.S. Appl. No. 14/351,654 (document cited in opposition of EP 2 787 078 on Feb. 28, 2020).
Claims filed on Sep. 5, 2018 in U.S. App. U.S. Appl. No. 14/351,654 (document cited in opposition of EP 2 787 078 on Feb. 28, 2020).
Examiner Lynn Anne Bristol, USPTO Final Office Action in U.S. Appl. No. 14/351,654, dated Apr. 14, 2016, 12 pages (document cited in opposition of EP 2 787 078 on Feb. 28, 2020).
Examiner Lynn Anne Bristol, USPTO Notice of Allowance and Examiner-Initiated Interview Summary in U.S. Appl. No. 13/990,088, dated Jan. 13, 2020, 11 pages.
Adlersberg et al., "The Immunoglobulin Hinge (Interdomain) Region," Ric Clin Lab, Jul.-Sep. 1976, 6(3):191-205.
Bi et al., "Treatment of hepatocellular carcinoma with a GPC3-targeted bispecific T cell engager," Oncotarget, May 16, 2017, 8(32):52866-52876. doi: 10.18632/oncotarget.17905. eCollection Aug. 8, 2017).
Carpenter et al., "Non-Fc Receptor-Binding Humanized Anti-CD3 Antibodies Induce Apoptosis of Activated Human T Cells," J Immunol, Dec. 1, 2000, 165(11):6205-6213. doi:10.4049/jimmunol.165.11.6205.
Chernajovsky et al., "Historical Development of Monoclonal Antibody Therapeutics," Therapeutic Antibodies, 2008, pp. 3-7.
Dall'Acqua et al., "Increasing the Affinity of a Human IgGI for the Neonatal Fc Receptor: Biological Consequences," J Immunol, Nov. 1, 2002, 169(9):5171-5180.
English translation of JP 2010-266760 (submitted by Opponent 3 on Mar. 26, 2020 in opposition of EP 2 647 707), 279 pages.
EPO opposition preliminary decision in opposition of EP 2 647 707, dated May 13, 2020, 23 pages.
Examination Report for EP 18192844.1, dated May 12, 2019 (submitted by Opponent 3 on Mar. 26, 2020 in opposition of EP 2 647 707), 6 pages.
Harada et al., "In vitro toxicological support to establish specification limit for anti-CD3 monospecific impurity in a bispecific T cell engager drug, ERY974," Toxicol In Vitro, Aug. 2020, 66:104841, 7 pages. doi: 10.1016/j.tiv.2020.104841. Epub Apr. 1, 2020).
Iwata et al., "Daily ascending dosing in cynomolgus monkeys to mitigate cytokine release syndrome induced by ERY22, surrogate for T-cell redirecting bispecific antibody ERY974 for cancer immunotherapy," Toxicol Appl Pharmacol, Sep. 15, 2019, 379:114657, 9 pages. doi: 10.1016/j.taap.2019.114657. Epub Jul. 19, 2019.
Lejeune et al., "Bispecific, T-Cell-Recruiting Antibodies in B-Cell Malignancies," Frontiers in Immunology, May 7, 2020, 11:762, 20 pages.
Mueller et al., "Humanized Porcine VCAM-Specific Monoclonal Antibodies with Chimeric IgG2/G4 Constant Regions Block Human Leukocyte Binding to Porcine Endothelial Cells," Mol Immunol, Apr. 1997, 34(6):441-452.
Runcie et al., "Bi-specific and tri-specific antibodies—the next big thing in solid tumor therapeutics," Molecular Medicine, Sep. 24, 2018, 24:50, 15 pages.
Shiraiwa et al., "Engineering a bispecific antibody with a common light chain: Identification and optimization of an anti-CD3 epsilon and anti-GPC3 bispecific antibody, ERY974," Methods, Feb. 1, 2019, 154:10-20. doi: 10.1016/j.ynneth.2018.10.005. Epub Oct. 13, 2018.
Szoor et al., "T Cell-Activating Mesenchymal Stem Cells as a Biotherapeutic for HCC," Mol Ther Oncolytics, Jul. 28, 2017, 6:69-79. doi: 10.1016/j.onnto.2017.07.002. eCollection Sep. 15, 2017.
Waaijer et al., "Preclinical PET imaging of bispecific antibody ERY974 targeting CD3 and glypican 3 reveals that tumor uptake correlates to T cell infiltrate," J Immunother Cancer, Mar. 2020, 8(1):e000548, 10 pages. doi: 10.1136/jitc-2020-000548.
Wenig et al., "Structure of the streptococcal endopeptidase IdeS, a cysteine proteinase with strict specificity of IgG," Proc Natl Acad Sci, USA 2004, 101:17371-17376.
Yu et al., "T cell-redirecting bispecific antibodies in cancer immunotherapy: recent advances," Jour Cancer Research and Clinical Oncology, Feb. 23, 2019, 145:941-956.
Yu et al., "A novel targeted GPC3/CD3 bispecific antibody for the treatment hepatocellular carcinoma," Can Biol Ther, Jul. 2, 2020, 21(7):597-603. doi: 10.1080/15384047.2020.1743158. Epub Apr. 2, 2020, abstract.
Examiner Lynn Anne Bristol, USPTO Non-Final Office Action in U.S. Appl. No. 13/990,088, dated Jun. 9, 2020, 10 pages.
Examiner Lynn Anne Bristol, USPTO Applicant-Initiated Interview Summary in U.S. Appl. No. 13/990,088, dated Jul. 31, 2020, 5 pages.
Examiner Lynn Anne Bristol, USPTO Examiner-Initiated Interview Summary in U.S. Appl. No. 13/990,088, dated Aug. 17, 2020, 5 pages.
Document from file history of EP 2787078, submitted on Sep. 16, 2021, by opposer in opposition proceedings for EP 2787078 (3 pages).
U.S. Appl. No. 15/782,256, Igawa et al., filed Oct. 12, 2017.
U.S. Appl. No. 15/562,186, Igawa et al., filed Sep. 27, 2017.
Baeuerle et al., "BiTE: Teaching antibodies to engage T-cells for cancer therapy," Curr Opin Mol They, Feb. 2009, 11(1):22-30.
Bolt et al., "The generation of a humanized, non-mitogenic CD3 monoclonal antibody which retains in vitro immunosuppressive properties," Eur J Immunol, Feb. 1993, 23(2):403-411.
Brezski et al., "The origins, specificity, and potential biological relevance of human anti-IgG hinge autoantibodies," Scientific World Journal, May 2, 20116, 11:1153-1167.
Brischwein et al., "MT110: A novel bispecific single-chain antibody construct with high efficacy in eradicating established tumors," Mol Immunol, Mar. 2006, 43(8):1129-1143. doi: 10.1016/j.molimm.2005.07.034. Epub Sep. 1, 2005.
Bugelski et al., "Monoclonal antibody-induced cytokine-release syndrome," Expert Rev Clin Immunol, Sep. 2009, 5(5):499-521.
Carter et al., "Potent antibody therapeutics by design," Nat Rev Immunol, May 2006, 6(5):343-357.
Dall'Acqua et al., "Contribution of Domain Interface Residues to the Stability of Antibody CH3 Domain Homodimers," Biochemistry, Jun. 30, 1998, 37(26):9266-9273. doi: 10.1021/bi980270i. PMID: 9649307.
Declaration of Christian Beil, signed Jun. 18, 2020, 6 pages (submitted by the opponent in the opposition proceedings of EP 3 050 963).
Declaration and Curriculum Vitae of Dr. K. Philipp Holliger, signed Feb. 19, 2021, 27 pages (submitted by the opponent in the opposition proceedings of EP 2 787 078 on Mar. 4, 2021).
Golay et al., "Design and Validation of a Novel Generic Platform for the Production of Tetravalent IgG1-like Bispecific Antibodies," J Immunol, Apr. 1, 2016, 196 (7):3199-3211.
Hammond et al., "Selective Targeting and Potent Control of Tumor Growth Using an EphA2/CD3- Bispecific Single-Chain Antibody Construct," Cancer Res, Apr. 1, 20075, 67(8):3927-3935. doi: 10.1158/0008-5472.CAN-06-2760.
Helguera et al., "Antibody-Cytokine Fusion Proteins for the Therapy of Cancer," Methods Mol Med, 2005, 109:347-374. doi: 10.1385/1-59259-862-5:347. PMID: 15585931.
Hessell et al., "Fc receptor but not complement binding is important in antibody protection against HIV," Nature, Sep. 6, 2007, 449(7158): 101-104.
Hugo et al., "Functional aspects of co-variant surface charges in an antibody fragment," Protein Sci, Nov. 2002, 11(11):2697-2705. doi: 10.1110/ps.0209302. PMID: 12381851; Pmcid: PMC2373727.

(56) References Cited

OTHER PUBLICATIONS

Kontermann, "Strategies to Extend Plasma Half-Lives of Recombinant Antibodies," BioDrugs, 2009, 23(2):93-109. doi: 10.2165/00063030-200923020-00003.
Kraft et al., "FcεRI-Mediated Activation of Transcription Factors in Antigen-Presenting Cells," Int Arch Allergy Immunol, May 2001, 125(1):9-15.
Lutterbuese et al., "Potent tumor killing and inhibition of tumor growth by CEA/CD3-bispecific single chain antibodies that are resistant to inhibition by soluble CEA," Proc Am Assoc Cancer Res front 98th AACR Annual Meeting, May 2007, vol. 67, Issue 9, Abstract 4106.
Lutterbuese et al., "Conversion of Cetuximab and Trastuzumab into T cell-engaging BiTE antibodies creates novel drug candidates with superior anti-tumor activity," Proc Am Assoc Cancer Res from 99th AACR Annual Meeting, May 2008, vol. 68, Issue 9, Abstract 2402.
Marme et al., "Intraperitoneal Bispecific Antibody (HEA125XOKT3) Therapy Inhibits Malignant Ascites Production in Advanced Ovarian Carcinoma," Int J Cancer, Sep. 10, 2002, 101(2):183-189.
Mazor et al., "Improving target cell specificity using a novel monovalent bispecific IgG design," mAbs, Mar./Apr. 2015, 7(2):377-389.
Otomo et al., "Structure of the heterodimeric complex between CAD domains of CAD and ICAD," Nat Struct Biol, Aug. 2000, 7(8):658-662. doi: 10.1038/77957. PMID: 10932250.
Raghavan et al., "Fc Receptors and Their Interactions with Immunoglobulins," Annu Rev Cell Dev Biol, Nov. 1996, 12:181-220.
Reference table: IMGT exon, EU and Kabat numbering of residues within the human IgGI sequence; retrieved from http://www.imgt.org/IMGTScientificChart/Numbering/Hu_IGHGnber.html on Jun. 1, 2020, 4 pages (cited by the opponents in the opposition proceedings of EP 3 050 963, which was notified to the patentee on Jul. 3, 2020).
Representative abstracts allegedly showing long-term administration of a variety of anti-cancer antibodies in the prior art, 5 pages (document submitted by the opponents in the opposition proceedings of EP 2 647 707 and reported in the EPO Communication issued Jan. 2, 20210; the document cites publication dates of the abstracts ranging from May 2006 to Feb. 2010).
Rother et al., "Discovery and development of the complement inhibitor eculizumab for the treatment of paroxysmal nocturnal hemoglobinuria," Nat Biotechnol, Nov. 2007, 25(11):1256-1264.
Santos et al., "Development of more efficacious antibodies for medical therapy and diagnosis," Prog Nucleic Acid Res Mol Biol, 1998, 60:169-194.
Saunders et al., "Conceptual Approaches to Modulating Antibody Effector Functions and Circulation Half-Life," Front Immunol, Jun. 7, 2019, 10(1296):1-20.
Schneider et al., "In vitro and in vivo properties of a dimeric bispecific single-chain antibody IgG-fusion protein for depletion of CCR2+ target cells in mice," Eur J Immunol, Mar. 2005, 35(3):987-995.
Sequence Alignments, 1 page (comparison of heavy chain constant region) (submitted by the Patentee (Chugai Seiyaku Kabushiki Kaisha) in the opposition proceedings of EP 2 647 707 on Dec. 23, 2020).
Thomas et al., "A Cell-Based Artificial Antigen-Presenting Cell Coated with Anti-CD3 and CD28 Antibodies Enables Rapid Expansion and Long-Term Growth of CD4 T Lymphocytes," Clin Immunol, Dec. 2002, 105(3):259-272.
Weiner et al., "The Role of T Cell Activation in Anti-CD3 x Antitumor Bispecific Antibody Therapy," J Immunol, Mar. 1, 1994, 152(5):2385-2392.
Zhao et al., "Targeting CD37-positive lymphoid malignancies with a novel engineered small modular immunopharmaceutical," Blood, Oct. 1, 2007, 110(7):2569-2577.
Examiner Lynn Anne Bristol, USPTO Final Office Action in U.S. Appl. No. 13/990,088, dated Dec. 1, 2020, 16 pages.
Examiner Stephen L. Rawlings, USPTO Non-Final Office Action in U.S. Appl. No. 11/910,128, dated Nov. 28, 2016, 17 pages.

U.S. Appl. No. 16/692,676, Kuramochi et al., filed Nov. 22, 2019.
U.S. Pat. No. 10,011,858, Igawa et al., dated Jul. 3, 2018.
U.S. Pat. No. 11,168,344, Igawa et al., dated Nov. 9, 2021.
U.S. Appl. No. 17/520,368, Igawa et al., filed Nov. 5, 2021.
U.S. Pat. No. 11,124,576, Igawa et al., dated Sep. 21, 2021.
U.S. Pat. No. 11,142,587, Igawa et al., dated Oct. 12, 2021.
U.S. Appl. No. 17/483,898, Igawa et al., filed Sep. 24, 2021.
U.S. Pat. No. 11,066,483, Nezu et al., dated Jul. 20, 2021.
U.S. Appl. No. 17/367,909, Nezu et al., filed Jul. 6, 2021.
Chothia et al., "Domain Association in Immunoglobulin Molecules—The Packing of Variable Domains," J Mol Biol, Dec. 5, 1985, 186(3):651-663. doi: 10.1016/0022-2836(85)90137-8.
Wikipedia entry for "Fc receptor" obtained from Wayback machine entry on May 29, 2010, 8 pages (submitted by Opponent 4 in the EPO opposition proceedings of EP 2 647 707 dated Dec. 31, 2021).
Examiner Lynn Anne Bristol, USPTO Non-Final Office Action in U.S. Appl. No. 16/692,676, dated Mar. 1, 2022, 23 pages.
U.S. Appl. No. 17/915,834, Sato et al., filed Sep. 29, 2022.
Amigorena et al., "Cytoplasmic Domain Heterogeneity and Functions of IgG Fc Receptors in B Lymphocytes," Science, Jun. 26, 1992, 256(5065):1808-1812.
Amigorena et al., "FcγRII expression in resting and activated B lymphocytes," Eur J Immunol, Aug. 1989, 19(8):1379-1385.
Baeuerle et al., "Bispecific T-Cell Engaging Antibodies for Cancer Therapy," Cancer Res, Jun. 15, 2009, 69(12):4941-4944. doi: 10.1158/0008-5472.CAN-09-0547. Epub Jun. 9, 2009.
Davis et al., "Abatacept binds to the Fc receptor CD64 but does not mediate complement-dependent cytotoxicity or antibody-dependent cellular cytotoxicity," J Rheumatol, Nov. 2007, 34(11):2204-2210.
Dreier et al., "Extremely potent, rapid and costimulation-independent cytotoxic t-cell response against lymphoma cells catalyzed by a single-chain bispecific antibody," Int J Cancer, Aug. 20, 2002, 100(6):690-697.
Gillies et al., "Antigen binding and biological activities of engineered mutant chimeric antibodies with human tumor specificities," Hum Antibodies Hybridomas, 1990, 1(1):47-54.
Goel et al., "Genetically Engineered Tetravalent Single-Chain Fv of the Pancarcinoma Monoclonal Antibody CC49: Improved Biodistribution and Potential for Therapeutic Application," Cancer Res, Dec. 15, 2000, 60(24):6964-6971.
Heyman, "Feedback regulation by IgG antibodies," Immunol Lett, Aug. 5, 2003, 88(2):157-161.
Kroesen et al., "Bispecific antibodies for treatment of cancer in experimental animal models and man," Adv Drug Deliv Rev, Apr. 6, 1998, 31(1-2): 105-129.
Muller et al., "Bispecific antibodies for cancer immunotherapy: Current perspectives," BioDrugs, Apr. 1, 2010, 24(2):89-98.
Muta et al., "A 13-amino-acid motif in the cytoplasmic domain of FcγRIIB modulates B-cell receptor signalling," Nature, Mar. 3, 1994, 368(6466):70-73.
Nicholas et al., "Regulation of the Immune Response. I. Reduction in Ability of Specific Antibody to Inhibit Long-Lasting IgG Immunological Priming After Removal of the Fc Fragment," J Exp Med, Jun. 1, 1969, 129(6):1183-1201.
O'Brien et al., "Biophysical characterization and molecular simulation of electrostatically driven self-association of a single-chain antibody," Protein Science, Jul. 2018, 27(7):1275-1285. doi: 10.1002/pro.3415. Epub May 3, 2018.
Ravetch et al., "Immune Inhibitory Receptors," Science, Oct. 6, 2000, 290(5489):84-89.
Smith et al., "FcγRIIB in autoimmunity and infection: evolutionary and therapeutic implications," Nat Rev Immunol, May 2010, 10(5):328-343.
Examiner Lynn Anne Bristol, USPTO Final Office Action in U.S. Appl. No. 16/692,676, dated Nov. 2, 2022, 23 pages.
Examiner Michael Edward Szperka, USPTO Restriction Requirement in U.S. Appl. No. 16/936,575, dated Oct. 6, 2022, 9 pages.
"FDA Grants Roche Breakthrough Therapy Designation on Hemophilia Drug," BioPharm International, UBM, Apr. 1, 20189, 1 page, printed from the Internet, http://www.biopharminternational.com/fda-grants-roche-breakthrough-therapy-designation-hemophilia-drug.

(56) References Cited

OTHER PUBLICATIONS

Schaefer et al., "Heavy and light chain pairing of bivalent quadroma and knobs-into-holes antibodies analyzed by UHR-ESI-QTOF mass spectrometry," mAbs, Jan. 2016, 8(1):49-55.
Sondermann et al., "The 3.2-Å crystal structure of the human IgG1 Fc fragment-FcγRIII complex," Nature, Jul. 20, 2000, 406(6793): 267-273.
Examiner Lynn Anne Bristol, USPTO Non-Final Office Action in U.S. Appl. No. 16/692,676, dated May 24, 2023, 12 pages.
Examiner Michael Edward Szperka, USPTO Non-Final Office Action in U.S. Appl. No. 16/936,575, dated Feb. 7, 2023, 12 pages.

* cited by examiner

```
IgA1  ASPTSPKVFPLSLCS---TQPDGNVVIACLVQGFFPQEPLSVTW--SESGQGVTARNFPP
IgA2  ASPTSPKVFPLSLDS---TPQDGNVVVACLVQGFFPQEPLSVTW--SESGQNVTARNFPP
IgD   AETKAPDVFPIISGCR-HPKDNSPVVLACLITGYHL-TSVTVTW--YMGTQSQPQRTFPE
IgE   ASTQSPSVFPLTRCCKNIPSNATSVTLGCLATGYFP-EPVMVTC--DTGSLNGTTMTFPA
IgG1  ASTKGPSVFPLAPSSK---STSGGTAALGCLVKDYFP-EPVTVSW--NSGALTSGVHTFPA
IgG2  ASTKGPSVFPLAPCSR---STSESTAALGCLVKDYFP-EPVTVSW--NSGALTSGVHTFPA
IgG3  ASTKGPSVFPLAPCSR---STSGGTAALGCLVKDYFP-EPVTVSW--NSGALTSGVHTFPA
IgG4  ASTKGPSVFPLAPCSR---STSESTAALGCLVKDYFP-EPVTVSW--NSGALTSGVHTFPA
IgM   GSASAPTLFPLVSCEN-SPSDTSSVAVGCLAQDFLP-DSITLSWKYKNNSDISSTRGFP-

IgA1  SQDASGDLYTTSSQLTLPATQCLAGKSVTCHVKHYTNPSQDVTVPCP- (SEQ ID NO: 63)
IgA2  SQDASGDLYTTSSQLTLPATQCPDGKSVTCHVKHYTNPSQDVTVPCP- (SEQ ID NO: 64)
IgD   -IQRDSYMTESQLSTDLQQ-WRQGEMCVCNIASKSKKDLTFRWP-    (SEQ ID NO: 65)
IgE   TTLLSGHYATISLLTV-SGA-WAKQMFTCRVAHTPSSTDWVDNKTFS  (SEQ ID NO: 66)
IgG1  -VHTFPAVLQSSGLYSLSSVVTVPSSS-LGTQTYICNVNHKPSNTKVDKKV--- (SEQ ID NO: 67)
IgG2  -VHTFPAVLQSSGLYSLSSVVTVPSSN-FGTQTYTCNVDHKPSNTKVDKTV--- (SEQ ID NO: 68)
IgG3  -VHTFPAVLQSSGLYSLSSVVTVPSSS-LGTQTYTCNVNHKPSNTKVDKRV--- (SEQ ID NO: 69)
IgG4  -VHTFPAVLQSSGLYSLSSVVTVPSSS-LGTKTYTCNVDHKPSNTKVDKRV--- (SEQ ID NO: 70)
IgM   -SVTRGSTVAATSQVLLPSKDVMQGTDEHVVCKVQHPNGNKEKNVPLP (SEQ ID NO: 71)

IgK   -RTVAAPSVFIFPPSDEQLKSGTASVVCLLNNFYPREAKVQWKVDNALQSGNSQESVTEQDSKDSTYSLS
IgL1  GQPKANPTVTLFPPSSEELQANKATLVCLISDFYPGAVTVAWKADGSPVKAGVETTKPSKQS-NNKYAAS
IgL2  GQPKAAPSVTLFPPSSEELQANKATLVCLISDFYPGAVTVAWKADSSPVKAGVETTTPSKQS-NNKYAAS
IgL3  GQPKAAPSVTLFPPSSEELQANKATLVCLISDFYPGAVTVAWKADSSPVKAGVETTKPSKQS-NNKYAAS
IgL6  GQPKAAPSVTLFPPSSEELQANKATLVCLISDFYPGAVTVAWKADSSPVKAGVETTKPSKQS-NNKYAAS
IgL7  GQPKAAPSVTLFPPSSEELQANKATLVCLISDFYPGAVTVAWKADSSPVKGVETTKPSKQS-NNKYAAS

IgK   SLTLSKADYEKHKVYACEVTHQGLSSPVTKSFNRGEC-  (SEQ ID NO: 72)
IgL1  SYLSLTPEQWKSHRSYSCQVTHEG--STVEKTVAPTECS (SEQ ID NO: 73)
IgL2  SYLSLTPEQWKSHRSYSCQVTHEG--STVEKTVAPTECS (SEQ ID NO: 74)
IgL3  SYLSLTPEQWKSHRSYSCQVTHEG--STVEKTVAPTECS (SEQ ID NO: 75)
IgL6  SYLSLTPEQWKSHRSYSCQVTHEG--STVEKTVAPTECS (SEQ ID NO: 76)
IgL7  SYLSLTPEQWKSHRSYSCNVTHEG--STVEKTVAPTECS (SEQ ID NO: 77)
```

FIG. 12

SEQUENCE LISTING

```
<160> NUMBER OF SEQ ID NOS: 79

<210> SEQ ID NO 1
<211> LENGTH: 328
<212> TYPE: PRT
<213> ORGANISM: Homo sapiens

<400> SEQUENCE: 1

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220
```

```
Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 2
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 2

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Glu Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255
```

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 3
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 3

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Lys Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro
            325

<210> SEQ ID NO 4
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 4

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Glu Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
            325

<210> SEQ ID NO 5
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 5

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Glu
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
            325

<210> SEQ ID NO 6

<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 6

```
Ala Ser Thr Lys Gly Pro Ser Val Phe Pro Leu Ala Pro Ser Ser Glu
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro
                325
```

<210> SEQ ID NO 7
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 7

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val Asp Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 8
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 8

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

```
                20                  25                  30

Phe Pro Glu Pro Val Thr Val Ser Trp Asn Ser Gly Ala Leu Thr Ser
                     35                  40                  45

Gly Val His Thr Lys Pro Ala Val Leu Gln Ser Ser Gly Leu Tyr Ser
                 50                  55                  60

Leu Ser Ser Val Val Thr Val Pro Ser Ser Ser Leu Gly Thr Gln Thr
         65                  70                  75                  80

Tyr Ile Cys Asn Val Asn His Lys Pro Ser Asn Thr Lys Val Asp Lys
                             85                  90                  95

Lys Val Glu Pro Lys Ser Cys Asp Lys Thr His Thr Cys Pro Pro Cys
                        100                 105                 110

Pro Ala Pro Glu Leu Leu Gly Gly Pro Ser Val Phe Leu Phe Pro Pro
                    115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
        145                 150                 155                 160

Tyr Val Asp Gly Val Glu Val His Asn Ala Lys Thr Lys Pro Arg Glu
                            165                 170                 175

Glu Gln Tyr Asn Ser Thr Tyr Arg Val Val Ser Val Leu Thr Val Leu
                        180                 185                 190

His Gln Asp Trp Leu Asn Gly Lys Glu Tyr Lys Cys Lys Val Ser Asn
                    195                 200                 205

Lys Ala Leu Pro Ala Pro Ile Glu Lys Thr Ile Ser Lys Ala Lys Gly
                210                 215                 220

Gln Pro Arg Glu Pro Gln Val Tyr Thr Leu Pro Pro Ser Arg Asp Glu
        225                 230                 235                 240

Leu Thr Lys Asn Gln Val Ser Leu Thr Cys Leu Val Lys Gly Phe Tyr
                            245                 250                 255

Pro Ser Asp Ile Ala Val Glu Trp Glu Ser Asn Gly Gln Pro Glu Asn
                        260                 265                 270

Asn Tyr Lys Thr Thr Pro Pro Val Leu Asp Ser Asp Gly Ser Phe Phe
                    275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
        305                 310                 315                 320

Gln Lys Ser Leu Ser Leu Ser Pro
                        325

<210> SEQ ID NO 9
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 9

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                    20                  25                  30

Phe Pro Glu Pro Val Thr Val Ser Trp Asn Ser Gly Ala Leu Thr Ser
                35                  40                  45

Gly Val His Thr Glu Pro Ala Val Leu Gln Ser Ser Gly Leu Tyr Ser
```

```
                50                  55                  60
Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 10
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 10

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Glu Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Glu Ser Ser Gly Leu Tyr Ser
        50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
```

```
            85                  90                  95
Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro
            325

<210> SEQ ID NO 11
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 11

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Glu Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Glu
            85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
```

```
            115                 120                 125
Lys Pro Lys Asp Thr Leu Met Ile Ser Arg Thr Pro Glu Val Thr Cys
    130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro
                325

<210> SEQ ID NO 12
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 12

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Glu Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Glu Ser Ser Gly Leu Tyr Ser
        50                  55                  60
Leu Ser Ser Val Val Thr Val Pro Ser Ser Leu Gly Thr Gln Thr
65                  70                  75                  80
Tyr Ile Cys Asn Val Asn His Lys Pro Ser Asn Thr Lys Val Asp Glu
                85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
    130                 135                 140
Val Val Val Asp Val Ser His Glu Asp Pro Glu Val Lys Phe Asn Trp
```

```
                145                 150                 155                 160
Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
                210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 13
<211> LENGTH: 107
<212> TYPE: PRT
<213> ORGANISM: Homo sapiens

<400> SEQUENCE: 13

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
                35                  40                  45

Ser Gly Asn Ser Gln Glu Ser Val Thr Glu Gln Asp Ser Lys Asp Ser
            50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
                100                 105

<210> SEQ ID NO 14
<211> LENGTH: 107
<212> TYPE: PRT
<213> ORGANISM: Artificial Sequence
<220> FEATURE:
<223> OTHER INFORMATION: an artificially synthesized sequence

<400> SEQUENCE: 14

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30
```

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Glu Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 15
<211> LENGTH: 107
<212> TYPE: PRT
<213> ORGANISM: Artificial Sequence
<220> FEATURE:
<223> OTHER INFORMATION: an artificially synthesized sequence

<400> SEQUENCE: 15

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Lys Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 16
<211> LENGTH: 107
<212> TYPE: PRT
<213> ORGANISM: Artificial Sequence
<220> FEATURE:
<223> OTHER INFORMATION: an artificially synthesized sequence

<400> SEQUENCE: 16

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
            35                  40                  45

Ser Gly Asn Ser Glu Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

-continued

<210> SEQ ID NO 17
<211> LENGTH: 107
<212> TYPE: PRT
<213> ORGANISM: Artificial Sequence
<220> FEATURE:
<223> OTHER INFORMATION: an artificially synthesized sequence

<400> SEQUENCE: 17

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Lys Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 18
<211> LENGTH: 107
<212> TYPE: PRT
<213> ORGANISM: Artificial Sequence
<220> FEATURE:
<223> OTHER INFORMATION: an artificially synthesized sequence

<400> SEQUENCE: 18

```
Arg Thr Val Ala Ala Pro Ser Val Phe Ile Phe Pro Pro Ser Asp Lys
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 19
<211> LENGTH: 107
<212> TYPE: PRT
<213> ORGANISM: Artificial Sequence
<220> FEATURE:
<223> OTHER INFORMATION: an artificially synthesized sequence

<400> SEQUENCE: 19

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Lys Asn Phe
            20                  25                  30

Tyr Pro Arg Glu Ala Lys Val Gln Trp Lys Val Asp Asn Ala Leu Gln
        35                  40                  45
```

```
Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 20
<211> LENGTH: 107
<212> TYPE: PRT
<213> ORGANISM: Artificial Sequence
<220> FEATURE:
<223> OTHER INFORMATION: an artificially synthesized sequence

<400> SEQUENCE: 20

Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Glu Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 21
<211> LENGTH: 107
<212> TYPE: PRT
<213> ORGANISM: Artificial Sequence
<220> FEATURE:
<223> OTHER INFORMATION: an artificially synthesized sequence

<400> SEQUENCE: 21

Arg Thr Val Ala Ala Pro Ser Val Phe Ile Phe Pro Pro Ser Asp Glu
 1               5                  10                  15

Gln Leu Lys Ser Gly Thr Ala Lys Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 22
<211> LENGTH: 107
<212> TYPE: PRT
```

<213> ORGANISM: Artificial Sequence
<220> FEATURE:
<223> OTHER INFORMATION: an artificially synthesized sequence

<400> SEQUENCE: 22

```
Arg Thr Val Ala Ala Pro Ser Val Phe Ile Phe Pro Pro Ser Asp Glu
1               5                   10                  15

Gln Leu Lys Ser Gly Thr Ala Glu Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 23
<211> LENGTH: 107
<212> TYPE: PRT
<213> ORGANISM: Artificial Sequence
<220> FEATURE:
<223> OTHER INFORMATION: an artificially synthesized sequence

<400> SEQUENCE: 23

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Asp Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 24
<211> LENGTH: 107
<212> TYPE: PRT
<213> ORGANISM: Artificial Sequence
<220> FEATURE:
<223> OTHER INFORMATION: an artificially synthesized sequence

<400> SEQUENCE: 24

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val His Glu Gln Asp Ser Lys Asp Ser
    50                  55                  60
```

```
Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105
```

<210> SEQ ID NO 25
<211> LENGTH: 107
<212> TYPE: PRT
<213> ORGANISM: Artificial Sequence
<220> FEATURE:
<223> OTHER INFORMATION: an artificially synthesized sequence

<400> SEQUENCE: 25

```
Arg Thr Val Ala Ala Pro Ser Val Phe Ile Phe Pro Pro Ser Asp Glu
  1               5                  10                  15

Gln Leu Lys Ser Gly Thr Ala Ser Val Val Cys Lys Leu Asn Asn Phe
             20                  25                  30

Tyr Pro Arg Glu Ala Lys Val Gln Trp Lys Val Asp Asn Ala Leu Gln
         35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105
```

<210> SEQ ID NO 26
<211> LENGTH: 107
<212> TYPE: PRT
<213> ORGANISM: Artificial Sequence
<220> FEATURE:
<223> OTHER INFORMATION: an artificially synthesized sequence

<400> SEQUENCE: 26

```
Arg Thr Val Ala Ala Pro Ser Val Phe Ile Phe Pro Pro Ser Asp Glu
  1               5                  10                  15

Gln Leu Lys Ser Gly Thr Ala Ser Val Val Cys Glu Leu Asn Asn Phe
             20                  25                  30

Tyr Pro Arg Glu Ala Lys Val Gln Trp Lys Val Asp Asn Ala Leu Gln
         35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105
```

<210> SEQ ID NO 27
<211> LENGTH: 107
<212> TYPE: PRT
<213> ORGANISM: Artificial Sequence
<220> FEATURE:
<223> OTHER INFORMATION: an artificially synthesized sequence

<400> SEQUENCE: 27

Arg Thr Val Ala Ala Pro Ser Val Phe Ile Phe Pro Pro Ser Asp Glu
1               5                   10                  15

Gln Leu Lys Ser Gly Thr Ala Lys Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Lys Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 28
<211> LENGTH: 107
<212> TYPE: PRT
<213> ORGANISM: Artificial Sequence
<220> FEATURE:
<223> OTHER INFORMATION: an artificially synthesized sequence

<400> SEQUENCE: 28

Arg Thr Val Ala Ala Pro Ser Val Phe Ile Phe Pro Pro Ser Asp Glu
1               5                   10                  15

Gln Leu Lys Ser Gly Thr Ala Glu Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Glu Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 29
<211> LENGTH: 107
<212> TYPE: PRT
<213> ORGANISM: Artificial Sequence
<220> FEATURE:
<223> OTHER INFORMATION: an artificially synthesized sequence

<400> SEQUENCE: 29

Arg Thr Val Ala Ala Pro Ser Val Phe Ile Phe Pro Pro Ser Asp Glu
1               5                   10                  15

Gln Leu Lys Ser Gly Thr Ala Lys Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Lys Glu Ser Val Thr Glu Gln Asp Ser Lys Asp Ser
    50                  55                  60

Thr Tyr Ser Leu Ser Ser Thr Leu Lys Leu Ser Lys Ala Asp Tyr Glu
65                  70                  75                  80

Lys His Lys Val Tyr Ala Cys Glu Val Thr His Gln Gly Leu Ser Ser
            85                  90                  95

Pro Val Thr Lys Ser Phe Asn Arg Gly Glu Cys
            100                 105

<210> SEQ ID NO 30
<211> LENGTH: 107
<212> TYPE: PRT
<213> ORGANISM: Artificial Sequence
<220> FEATURE:
<223> OTHER INFORMATION: an artificially synthesized sequence

<400> SEQUENCE: 30

Arg Thr Val Ala Ala Pro Ser Val Phe Ile Phe Pro Pro Ser Asp Glu
1               5                   10                  15

Gln Leu Lys Ser Gly Thr Ala Glu Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Glu Glu Ser Val Thr Glu Gln Asp Ser Lys Asp Ser
    50                  55                  60

Thr Tyr Ser Leu Ser Ser Thr Leu Glu Leu Ser Lys Ala Asp Tyr Glu
65                  70                  75                  80

Lys His Lys Val Tyr Ala Cys Glu Val Thr His Gln Gly Leu Ser Ser
            85                  90                  95

Pro Val Thr Lys Ser Phe Asn Arg Gly Glu Cys
            100                 105

<210> SEQ ID NO 31
<211> LENGTH: 107
<212> TYPE: PRT
<213> ORGANISM: Artificial Sequence
<220> FEATURE:
<223> OTHER INFORMATION: an artificially synthesized sequence

<400> SEQUENCE: 31

Arg Thr Val Ala Ala Pro Ser Val Phe Ile Phe Pro Pro Ser Asp Lys
1               5                   10                  15

Gln Leu Lys Ser Gly Thr Ala Lys Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Lys Leu Ser Lys Ala Asp Tyr Glu
65                  70                  75                  80

Lys His Lys Val Tyr Ala Cys Glu Val Thr His Gln Gly Leu Ser Ser
            85                  90                  95

Pro Val Thr Lys Ser Phe Asn Arg Gly Glu Cys
            100                 105

<210> SEQ ID NO 32
<211> LENGTH: 107
<212> TYPE: PRT
<213> ORGANISM: Artificial Sequence
<220> FEATURE:
<223> OTHER INFORMATION: an artificially synthesized sequence

<400> SEQUENCE: 32

Arg Thr Val Ala Ala Pro Ser Val Phe Ile Phe Pro Pro Ser Asp Lys
1               5                   10                  15

Gln Leu Lys Ser Gly Thr Ala Lys Val Val Cys Leu Leu Asn Asn Phe
            20                  25                  30

Tyr Pro Arg Glu Ala Lys Val Gln Trp Lys Val Asp Asn Ala Leu Gln
            35                  40                  45

Ser Gly Asn Ser Lys Glu Ser Val Thr Glu Gln Asp Ser Lys Asp Ser
50                  55                  60

Thr Tyr Ser Leu Ser Ser Thr Leu Lys Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 33
<211> LENGTH: 107
<212> TYPE: PRT
<213> ORGANISM: Artificial Sequence
<220> FEATURE:
<223> OTHER INFORMATION: an artificially synthesized sequence

<400> SEQUENCE: 33

Arg Thr Val Ala Ala Pro Ser Val Phe Ile Phe Pro Pro Ser Asp Glu
1               5                   10                  15

Gln Leu Lys Ser Gly Thr Ala Glu Val Val Cys Leu Leu Asn Asn Phe
            20                  25                  30

Tyr Pro Arg Glu Ala Lys Val Gln Trp Lys Val Asp Asn Ala Leu Gln
            35                  40                  45

Ser Gly Asn Ser Glu Glu Ser Val Thr Glu Gln Asp Ser Lys Asp Ser
50                  55                  60

Thr Tyr Ser Leu Ser Ser Thr Leu Glu Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 34
<211> LENGTH: 115
<212> TYPE: PRT
<213> ORGANISM: Homo sapiens

<400> SEQUENCE: 34

Gln Val Gln Leu Val Gln Ser Gly Ala Glu Val Lys Lys Pro Gly Ala
1               5                   10                  15

Ser Val Thr Val Ser Cys Lys Ala Ser Gly Tyr Thr Phe Thr Asp Tyr
            20                  25                  30

Glu Met His Trp Ile Arg Gln Pro Pro Gly Gln Gly Leu Glu Trp Ile
            35                  40                  45

Gly Ala Ile Asp Pro Lys Thr Gly Asp Thr Ala Tyr Ser Glu Ser Phe
50                  55                  60

Gln Asp Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr

Val Ser Ser
        115

<210> SEQ ID NO 35
<211> LENGTH: 112
<212> TYPE: PRT
<213> ORGANISM: Homo sapiens

<400> SEQUENCE: 35

Asp Ile Val Met Thr Gln Ser Pro Leu Ser Leu Pro Val Thr Pro Gly
1               5                   10                  15

Glu Pro Ala Ser Ile Ser Cys Gln Ala Ser Gln Ser Leu Val His Ser
            20                  25                  30

Asn Arg Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Val Glu Ile Glu
            100                 105                 110

<210> SEQ ID NO 36
<211> LENGTH: 119
<212> TYPE: PRT
<213> ORGANISM: Homo sapiens

<400> SEQUENCE: 36

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser
        115

<210> SEQ ID NO 37
<211> LENGTH: 107
<212> TYPE: PRT
<213> ORGANISM: Homo sapiens

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

```
Leu Asn Trp Tyr Gln Gln Lys Pro Gly Lys Ala Pro Lys Leu Leu Ile
            35                  40                  45

Tyr Tyr Thr Ser Arg Leu His Ser Gly Val Pro Ser Arg Phe Ser Gly
        50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys
                100                 105

<210> SEQ ID NO 38
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 38

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Cys Thr Leu Pro Pro Ser Arg Asp Glu
225                 230                 235                 240

Leu Thr Lys Asn Gln Val Ser Leu Trp Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro
            325

<210> SEQ ID NO 39
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 39

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Lys Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Cys Thr Leu Pro Pro Ser Arg Asp Glu
225                 230                 235                 240

Leu Thr Lys Asn Gln Val Ser Leu Trp Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
            325

<210> SEQ ID NO 40
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 40

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Glu Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Glu Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Cys Thr Leu Pro Pro Ser Arg Asp Glu
225                 230                 235                 240

Leu Thr Lys Asn Gln Val Ser Leu Trp Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
            325

<210> SEQ ID NO 41

```
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 41

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Glu Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Glu Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Glu
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Cys Thr Leu Pro Pro Ser Arg Asp Glu
225                 230                 235                 240

Leu Thr Lys Asn Gln Val Ser Leu Trp Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 42
<211> LENGTH: 328
<212> TYPE: PRT
<213> ORGANISM: Artificial Sequence
<220> FEATURE:
<223> OTHER INFORMATION: an artificially synthesized sequence
```

<400> SEQUENCE: 42

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Cys Glu
225                 230                 235                 240

Leu Thr Lys Asn Gln Val Ser Leu Ser Cys Ala Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Val Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 43
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 43

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr

-continued

```
                20                  25                  30
        Phe Pro Glu Pro Val Thr Val Ser Trp Asn Ser Gly Ala Leu Thr Ser
                    35                  40                  45

Gly Val His Thr Phe Pro Ala Val Leu Lys Ser Ser Gly Leu Tyr Ser
                50                  55                  60

Leu Ser Ser Val Val Thr Val Pro Ser Ser Ser Leu Gly Thr Gln Thr
        65                  70                  75                  80

Tyr Ile Cys Asn Val Asn His Lys Pro Ser Asn Thr Lys Val Asp Lys
                        85                  90                  95

Lys Val Glu Pro Lys Ser Cys Asp Lys Thr His Thr Cys Pro Pro Cys
                    100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
                    130                 135                 140

Val Val Val Asp Val Ser His Glu Asp Pro Glu Val Lys Phe Asn Trp
        145                 150                 155                 160

Tyr Val Asp Gly Val Glu Val His Asn Ala Lys Thr Lys Pro Arg Glu
                        165                 170                 175

Glu Gln Tyr Asn Ser Thr Tyr Arg Val Val Ser Val Leu Thr Val Leu
                    180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
                    210                 215                 220

Gln Pro Arg Glu Pro Gln Val Tyr Thr Leu Pro Pro Ser Arg Cys Glu
        225                 230                 235                 240

Leu Thr Lys Asn Gln Val Ser Leu Ser Cys Ala Val Lys Gly Phe Tyr
                        245                 250                 255

Pro Ser Asp Ile Ala Val Glu Trp Glu Ser Asn Gly Gln Pro Glu Asn
                    260                 265                 270

Asn Tyr Lys Thr Thr Pro Pro Val Leu Asp Ser Asp Gly Ser Phe Phe
                275                 280                 285

Leu Val Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
        305                 310                 315                 320

Gln Lys Ser Leu Ser Leu Ser Pro
                        325

<210> SEQ ID NO 44
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 44

Ala Ser Thr Lys Gly Pro Ser Val Phe Pro Leu Ala Pro Ser Ser Lys
        1               5                   10                  15

Ser Thr Ser Gly Gly Thr Ala Ala Leu Gly Cys Leu Val Glu Asp Tyr
                        20                  25                  30

Phe Pro Glu Pro Val Thr Val Ser Trp Asn Ser Gly Ala Leu Thr Ser
                    35                  40                  45

Gly Val His Thr Phe Pro Ala Val Leu Glu Ser Ser Gly Leu Tyr Ser
```

```
                50                  55                  60
Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                    85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Cys Glu
225                 230                 235                 240

Leu Thr Lys Asn Gln Val Ser Leu Ser Cys Ala Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Val Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 45
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 45

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Glu Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Glu Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Glu
```

```
                85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
            115                 120                 125
Lys Pro Lys Asp Thr Leu Met Ile Ser Arg Thr Pro Glu Val Thr Cys
            130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
            195                 200                 205
Lys Ala Leu Pro Ala Pro Ile Glu Lys Thr Ile Ser Lys Ala Lys Gly
            210                 215                 220
Gln Pro Arg Glu Pro Gln Val Tyr Thr Leu Pro Pro Ser Arg Cys Glu
225                 230                 235                 240
Leu Thr Lys Asn Gln Val Ser Leu Ser Cys Ala Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
            275                 280                 285
Leu Val Ser Lys Leu Thr Val Asp Lys Ser Arg Trp Gln Gln Gly Asn
            290                 295                 300
Val Phe Ser Cys Ser Val Met His Glu Ala Leu His Asn His Tyr Thr
305                 310                 315                 320
Gln Lys Ser Leu Ser Leu Ser Pro
                325

<210> SEQ ID NO 46
<211> LENGTH: 119
<212> TYPE: PRT
<213> ORGANISM: Artificial Sequence
<220> FEATURE:
<223> OTHER INFORMATION: an artificially synthesized sequence

<400> SEQUENCE: 46

Gln Val Gln Leu Gln Glu Ser Gly Pro Gly Leu Val Arg Pro Ser Gln
1               5                   10                  15
Thr Leu Ser Leu Thr Cys Thr Val Ser Gly Tyr Ser Ile Thr Ser Asp
            20                  25                  30
His Ala Trp Ser Trp Val Arg Lys Pro Pro Gly Arg Gly Leu Glu Trp
            35                  40                  45
Ile Gly Tyr Ile Ser Tyr Ser Gly Ile Thr Thr Tyr Asn Pro Ser Leu
            50                  55                  60
Lys Ser Arg Val Thr Met Leu Arg Asp Thr Ser Lys Asn Gln Phe Ser
65                  70                  75                  80
Leu Arg Leu Ser Ser Val Thr Ala Ala Asp Thr Ala Val Tyr Tyr Cys
                85                  90                  95
Ala Arg Ser Leu Ala Arg Thr Thr Ala Met Asp Tyr Trp Gly Gln Gly
            100                 105                 110
Ser Leu Val Thr Val Ser Ser
```

-continued

```
<210> SEQ ID NO 47
<211> LENGTH: 119
<212> TYPE: PRT
<213> ORGANISM: Artificial Sequence
<220> FEATURE:
<223> OTHER INFORMATION: an artificially synthesized sequence

<400> SEQUENCE: 47

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Glu Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser
        115

<210> SEQ ID NO 48
<211> LENGTH: 115
<212> TYPE: PRT
<213> ORGANISM: Artificial Sequence
<220> FEATURE:
<223> OTHER INFORMATION: an artificially synthesized sequence

<400> SEQUENCE: 48

Gln Val Gln Leu Val Gln Ser Gly Ala Glu Val Lys Lys Pro Gly Ala
1               5                   10                  15

Ser Val Thr Val Ser Cys Lys Ala Ser Gly Tyr Thr Phe Thr Asp Tyr
            20                  25                  30

Glu Met His Trp Ile Arg Lys Pro Pro Gly Glu Gly Leu Glu Trp Ile
        35                  40                  45

Gly Ala Ile Asp Pro Lys Thr Gly Asp Thr Ala Tyr Ser Glu Ser Phe
    50                  55                  60

Gln Asp Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser
        115

<210> SEQ ID NO 49
<211> LENGTH: 115
<212> TYPE: PRT
<213> ORGANISM: Artificial Sequence
<220> FEATURE:
<223> OTHER INFORMATION: an artificially synthesized sequence

<400> SEQUENCE: 49
```

Gln Val Gln Leu Val Gln Ser Gly Ala Glu Val Lys Pro Gly Ala
1               5                   10                  15

Ser Val Thr Val Ser Cys Lys Ala Ser Gly Tyr Thr Phe Thr Asp Tyr
            20                  25                  30

Glu Met His Trp Ile Arg Glu Pro Gly Glu Gly Leu Glu Trp Ile
        35                  40                  45

Gly Ala Ile Asp Pro Lys Thr Gly Asp Thr Ala Tyr Ser Glu Ser Phe
50                  55                  60

Gln Asp Arg Val Thr Leu Thr Ala Asp Lys Ser Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
                100                 105                 110

Val Ser Ser
        115

<210> SEQ ID NO 50
<211> LENGTH: 107
<212> TYPE: PRT
<213> ORGANISM: Artificial Sequence
<220> FEATURE:
<223> OTHER INFORMATION: an artificially synthesized sequence

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Glu Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys
                100                 105

<210> SEQ ID NO 51
<211> LENGTH: 107
<212> TYPE: PRT
<213> ORGANISM: Artificial Sequence
<220> FEATURE:
<223> OTHER INFORMATION: an artificially synthesized sequence

<400> SEQUENCE: 51

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Lys Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro

```
              65                  70                  75                  80
Glu Asp Ile Ala Thr Tyr Tyr Cys Gln Gln Gly Asn Thr Leu Pro Tyr
                    85                  90                  95

Thr Phe Gly Gln Gly Thr Lys Val Glu Ile Lys
            100                 105
```

<210> SEQ ID NO 52
<211> LENGTH: 112
<212> TYPE: PRT
<213> ORGANISM: Artificial Sequence
<220> FEATURE:
<223> OTHER INFORMATION: an artificially synthesized sequence

<400> SEQUENCE: 52

```
Asp Ile Val Met Thr Gln Ser Pro Leu Ser Leu Pro Val Thr Pro Gly
1               5                   10                  15

Glu Pro Ala Ser Ile Ser Cys Gln Ala Ser Glu Ser Leu Val His Ser
                20                  25                  30

Asn Arg Asn Thr Tyr Leu His Trp Tyr Leu Glu Lys Pro Gly Gln Ser
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Val Glu Ile Glu
            100                 105                 110
```

<210> SEQ ID NO 53
<211> LENGTH: 112
<212> TYPE: PRT
<213> ORGANISM: Artificial Sequence
<220> FEATURE:
<223> OTHER INFORMATION: an artificially synthesized sequence

<400> SEQUENCE: 53

```
Asp Ile Val Met Thr Gln Ser Pro Leu Ser Leu Pro Val Thr Pro Gly
1               5                   10                  15

Glu Pro Ala Ser Ile Ser Cys Gln Ala Ser Glu Ser Leu Val His Ser
                20                  25                  30

Asn Arg Asn Thr Tyr Leu His Trp Tyr Leu Lys Lys Pro Gly Gln Ser
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Val Glu Ile Glu
            100                 105                 110
```

<210> SEQ ID NO 54
<211> LENGTH: 125
<212> TYPE: PRT
<213> ORGANISM: Homo sapiens

<400> SEQUENCE: 54

```
Glu Val Lys Leu Leu Glu Ser Gly Gly Gly Leu Val Gln Pro Lys Gly
```

```
                1               5                  10                 15
    Ser Leu Lys Leu Ser Cys Ala Ala Ser Gly Phe Thr Phe Asn Thr Tyr
                    20                 25                 30

Ala Met Asn Trp Val Arg Gln Ala Pro Gly Lys Gly Leu Glu Trp Val
                    35                 40                 45

Ala Arg Ile Arg Ser Lys Tyr Asn Asn Tyr Ala Thr Tyr Tyr Ala Asp
                    50                 55                 60

Ser Val Lys Asp Arg Phe Thr Ile Ser Arg Asp Asp Ser Gln Ser Ile
    65                  70                 75                  80

Leu Tyr Leu Gln Met Asn Asn Leu Lys Thr Glu Asp Thr Ala Met Tyr
                    85                 90                 95

Tyr Cys Val Arg His Gly Asn Phe Gly Asn Ser Tyr Val Ser Trp Phe
                    100                105                110

Ala Tyr Trp Gly Gln Gly Thr Leu Val Thr Val Ser Ala
                    115                120                125

<210> SEQ ID NO 55
<211> LENGTH: 115
<212> TYPE: PRT
<213> ORGANISM: Homo sapiens

<400> SEQUENCE: 55

Gln Val Gln Leu Val Gln Ser Gly Ala Glu Val Lys Lys Pro Gly Ala
    1               5                   10                 15

Ser Val Lys Val Ser Cys Lys Ala Ser Gly Tyr Thr Phe Thr Asp Tyr
                    20                 25                 30

Glu Met His Trp Ile Arg Gln Pro Pro Gly Gln Gly Leu Glu Trp Ile
                    35                 40                 45

Gly Ala Ile Asp Pro Lys Thr Gly Asp Thr Ala Tyr Ser Gln Lys Phe
                    50                 55                 60

Lys Gly Arg Val Thr Leu Thr Ala Asp Lys Ser Thr Ser Thr Ala Tyr
    65                  70                 75                  80

Met Glu Leu Ser Ser Leu Thr Ser Glu Asp Thr Ala Val Tyr Tyr Cys
                    85                 90                 95

Thr Arg Phe Tyr Ser Tyr Thr Tyr Trp Gly Gln Gly Thr Leu Val Thr
                    100                105                110

Val Ser Ser
            115

<210> SEQ ID NO 56
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 56

Ala Ser Thr Lys Gly Pro Ser Val Phe Pro Leu Ala Pro Ser Ser Lys
    1               5                   10                 15

Ser Thr Ser Gly Gly Thr Ala Ala Leu Gly Cys Leu Val Lys Asp Tyr
                    20                 25                 30

Phe Pro Glu Pro Val Thr Val Ser Trp Asn Ser Gly Ala Leu Thr Ser
                    35                 40                 45

Gly Val His Thr Phe Pro Ala Val Leu Gln Ser Ser Gly Leu Tyr Ser
                    50                 55                 60

Leu Ser Ser Val Val Thr Val Pro Ser Ser Ser Leu Gly Thr Gln Thr
    65                  70                 75                  80
```

```
Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 57
<211> LENGTH: 109
<212> TYPE: PRT
<213> ORGANISM: Homo sapiens

<400> SEQUENCE: 57

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

Leu Trp Val Phe Gly Gly Gly Thr Lys Leu Thr Val Leu
            100                 105
```

```
<210> SEQ ID NO 58
<211> LENGTH: 112
<212> TYPE: PRT
<213> ORGANISM: Homo sapiens

<400> SEQUENCE: 58

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Arg Asn Thr Tyr Leu His Trp Tyr Gln Gln Lys Pro Gly Gln Ala
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

<210> SEQ ID NO 59
<211> LENGTH: 447
<212> TYPE: PRT
<213> ORGANISM: Homo sapiens

<400> SEQUENCE: 59

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
```

```
                225                 230                 235                 240
        Ser Val Phe Leu Phe Pro Pro Lys Pro Lys Asp Thr Leu Met Ile Ser
                        245                 250                 255

Arg Thr Pro Glu Val Thr Cys Val Val Val Asp Val Ser His Glu Asp
                        260                 265                 270

Pro Glu Val Lys Phe Asn Trp Tyr Val Asp Gly Val Glu Val His Asn
                        275                 280                 285

Ala Lys Thr Lys Pro Arg Glu Glu Gln Tyr Asn Ser Thr Tyr Arg Val
                290                 295                 300

Val Ser Val Leu Thr Val Leu His Gln Asp Trp Leu Asn Gly Lys Glu
        305                 310                 315                 320

Tyr Lys Cys Lys Val Ser Asn Lys Ala Leu Pro Ala Pro Ile Glu Lys
                        325                 330                 335

Thr Ile Ser Lys Ala Lys Gly Gln Pro Arg Glu Pro Gln Val Tyr Thr
                        340                 345                 350

Leu Pro Pro Ser Arg Asp Glu Leu Thr Lys Asn Gln Val Ser Leu Thr
                        355                 360                 365

Cys Leu Val Lys Gly Phe Tyr Pro Ser Asp Ile Ala Val Glu Trp Glu
                370                 375                 380

Ser Asn Gly Gln Pro Glu Asn Asn Tyr Lys Thr Thr Pro Pro Val Leu
        385                 390                 395                 400

Asp Ser Asp Gly Ser Phe Phe Leu Tyr Ser Lys Leu Thr Val Asp Lys
                        405                 410                 415

Ser Arg Trp Gln Gln Gly Asn Val Phe Ser Cys Ser Val Met His Glu
                        420                 425                 430

Ala Leu His Asn His Tyr Thr Gln Lys Ser Leu Ser Leu Ser Pro
                        435                 440                 445

<210> SEQ ID NO 60
<211> LENGTH: 214
<212> TYPE: PRT
<213> ORGANISM: Homo sapiens

<400> SEQUENCE: 60

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 61
<211> LENGTH: 443
<212> TYPE: PRT
<213> ORGANISM: Homo sapiens

<400> SEQUENCE: 61

Gln Val Gln Leu Val Gln Ser Gly Ala Glu Val Lys Lys Pro Gly Ala
1               5                   10                  15

Ser Val Thr Val Ser Cys Lys Ala Ser Gly Tyr Thr Phe Thr Asp Tyr
            20                  25                  30

Glu Met His Trp Ile Arg Gln Pro Pro Gly Glu Gly Leu Glu Trp Ile
        35                  40                  45

Gly Ala Ile Asp Pro Lys Thr Gly Asp Thr Ala Tyr Ser Glu Ser Phe
    50                  55                  60

Gln Asp Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320
```

```
Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
        340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro
            435                 440
```

<210> SEQ ID NO 62
<211> LENGTH: 219
<212> TYPE: PRT
<213> ORGANISM: Homo sapiens

<400> SEQUENCE: 62

```
Asp Ile Val Met Thr Gln Ser Pro Leu Ser Leu Pro Val Thr Pro Gly
1               5                   10                  15

Glu Pro Ala Ser Ile Ser Cys Gln Ala Ser Glu Ser Leu Val His Ser
            20                  25                  30

Asn Arg Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Val Glu Ile Glu
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 63
<211> LENGTH: 102
<212> TYPE: PRT

<213> ORGANISM: Homo sapiens

<400> SEQUENCE: 63

Ala Ser Pro Thr Ser Pro Lys Val Phe Pro Leu Ser Leu Cys Ser Thr
1               5                   10                  15

Gln Pro Asp Gly Asn Val Val Ile Ala Cys Leu Val Gln Gly Phe Phe
            20                  25                  30

Pro Gln Glu Pro Leu Ser Val Thr Trp Ser Glu Ser Gly Gln Gly Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Leu Ala Gly
65                  70                  75                  80

Lys Ser Val Thr Cys His Val Lys His Tyr Thr Asn Pro Ser Gln Asp
                85                  90                  95

Val Thr Val Pro Cys Pro
            100

<210> SEQ ID NO 64
<211> LENGTH: 102
<212> TYPE: PRT
<213> ORGANISM: Homo sapiens

<400> SEQUENCE: 64

Ala Ser Pro Thr Ser Pro Lys Val Phe Pro Leu Ser Leu Asp Ser Thr
1               5                   10                  15

Pro Gln Asp Gly Asn Val Val Val Ala Cys Leu Val Gln Gly Phe Phe
            20                  25                  30

Pro Gln Glu Pro Leu Ser Val Thr Trp Ser Glu Ser Gly Gln Asn Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Pro Asp Gly
65                  70                  75                  80

Lys Ser Val Thr Cys His Val Lys His Tyr Thr Asn Pro Ser Gln Asp
                85                  90                  95

Val Thr Val Pro Cys Pro
            100

<210> SEQ ID NO 65
<211> LENGTH: 101
<212> TYPE: PRT
<213> ORGANISM: Homo sapiens

<400> SEQUENCE: 65

Ala Pro Thr Lys Ala Pro Asp Val Phe Pro Ile Ile Ser Gly Cys Arg
1               5                   10                  15

His Pro Lys Asp Asn Ser Pro Val Val Leu Ala Cys Leu Ile Thr Gly
            20                  25                  30

Tyr His Pro Thr Ser Val Thr Val Thr Trp Tyr Met Gly Thr Gln Ser
        35                  40                  45

Gln Pro Gln Arg Thr Phe Pro Glu Ile Gln Arg Arg Asp Ser Tyr Tyr
    50                  55                  60

Met Thr Ser Ser Gln Leu Ser Thr Pro Leu Gln Gln Trp Arg Gln Gly
65                  70                  75                  80

Glu Tyr Lys Cys Val Val Gln His Thr Ala Ser Lys Ser Lys Lys Glu
                85                  90                  95

Ile Phe Arg Trp Pro
            100

<210> SEQ ID NO 66
<211> LENGTH: 103
<212> TYPE: PRT
<213> ORGANISM: Homo sapiens

<400> SEQUENCE: 66

Ala Ser Thr Gln Ser Pro Ser Val Phe Pro Leu Thr Arg Cys Cys Lys
1               5                   10                  15

Asn Ile Pro Ser Asn Ala Thr Ser Val Thr Leu Gly Cys Leu Ala Thr
            20                  25                  30

Gly Tyr Phe Pro Glu Pro Val Met Val Thr Cys Asp Thr Gly Ser Leu
        35                  40                  45

Asn Gly Thr Thr Met Thr Leu Pro Ala Thr Leu Thr Leu Ser Gly
    50                  55                  60

His Tyr Ala Thr Ile Ser Leu Leu Thr Val Ser Gly Ala Trp Ala Lys
65                  70                  75                  80

Gln Met Phe Thr Cys Arg Val Ala His Thr Pro Ser Ser Thr Asp Trp
                85                  90                  95

Val Asp Asn Lys Thr Phe Ser
            100

<210> SEQ ID NO 67
<211> LENGTH: 98
<212> TYPE: PRT
<213> ORGANISM: Homo sapiens

<400> SEQUENCE: 67

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 68
<211> LENGTH: 98
<212> TYPE: PRT
<213> ORGANISM: Homo sapiens

<400> SEQUENCE: 68

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser

```
                    50                  55                  60
Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                     85                  90                  95

Thr Val

<210> SEQ ID NO 69
<211> LENGTH: 98
<212> TYPE: PRT
<213> ORGANISM: Homo sapiens

<400> SEQUENCE: 69

Ala Ser Thr Lys Gly Pro Ser Val Phe Pro Leu Ala Pro Cys Ser Arg
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
 65                  70                  75                  80

Tyr Thr Cys Asn Val Asn His Lys Pro Ser Asn Thr Lys Val Asp Lys
                     85                  90                  95

Arg Val

<210> SEQ ID NO 70
<211> LENGTH: 98
<212> TYPE: PRT
<213> ORGANISM: Homo sapiens

<400> SEQUENCE: 70

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                     85                  90                  95

Arg Val

<210> SEQ ID NO 71
<211> LENGTH: 104
<212> TYPE: PRT
<213> ORGANISM: Homo sapiens

<400> SEQUENCE: 71

Gly Ser Ala Ser Ala Pro Thr Leu Phe Pro Leu Val Ser Cys Glu Asn
 1               5                  10                  15

Ser Pro Ser Asp Thr Ser Ser Val Ala Val Gly Cys Leu Ala Gln Asp
                20                  25                  30
```

```
Phe Leu Pro Asp Ser Ile Thr Leu Ser Trp Lys Tyr Lys Asn Asn Ser
            35                  40                  45

Asp Ile Ser Ser Thr Arg Gly Phe Pro Ser Val Leu Arg Gly Gly Lys
        50                  55                  60

Tyr Ala Ala Thr Ser Gln Val Leu Leu Pro Ser Lys Asp Val Met Gln
 65                 70                  75                  80

Gly Thr Asp Glu His Val Val Cys Lys Val Gln His Pro Asn Gly Asn
                85                  90                  95

Lys Glu Lys Asn Val Pro Leu Pro
                100

<210> SEQ ID NO 72
<211> LENGTH: 107
<212> TYPE: PRT
<213> ORGANISM: Homo sapiens

<400> SEQUENCE: 72

Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
 50                 55                  60

Thr Tyr Ser Leu Ser Ser Thr Leu Thr Leu Ser Lys Ala Asp Tyr Glu
 65                 70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 73
<211> LENGTH: 106
<212> TYPE: PRT
<213> ORGANISM: Homo sapiens

<400> SEQUENCE: 73

Gly Gln Pro Lys Ala Asn Pro Thr Val Thr Leu Phe Pro Pro Ser Ser
 1               5                  10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
 50                 55                  60

Lys Tyr Ala Ala Ser Ser Tyr Leu Ser Leu Thr Pro Glu Gln Trp Lys
 65                 70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 74
<211> LENGTH: 106
<212> TYPE: PRT
<213> ORGANISM: Homo sapiens
```

-continued

<400> SEQUENCE: 74

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 75
<211> LENGTH: 106
<212> TYPE: PRT
<213> ORGANISM: Homo sapiens

<400> SEQUENCE: 75

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Lys Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 76
<211> LENGTH: 106
<212> TYPE: PRT
<213> ORGANISM: Homo sapiens

<400> SEQUENCE: 76

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Lys Val Ala Trp Lys Ala Asp Gly Ser Pro
        35                  40                  45

Val Asn Thr Gly Val Glu Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Ala Glu Cys Ser
            100                 105

<210> SEQ ID NO 77
<211> LENGTH: 106
<212> TYPE: PRT
<213> ORGANISM: Homo sapiens

<400> SEQUENCE: 77

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Val Ser Asp
            20                  25                  30

Phe Tyr Pro Gly Ala Val Thr Val Ala Trp Lys Ala Asp Gly Ser Pro
        35                  40                  45

Val Lys Val Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Arg Val Thr His Glu Gly Ser Thr Val
                85                  90                  95

Glu Lys Thr Val Ala Pro Ala Glu Cys Ser
            100                 105

<210> SEQ ID NO 78
<211> LENGTH: 1731
<212> TYPE: DNA
<213> ORGANISM: Homo sapiens

<400> SEQUENCE: 78

| | |
|---|---|
| aactgcagcg ccggggctgg gggaggggag cctactcact cccccaactc ccgggcggtg | 60 |
| actcatcaac gagcaccagc ggccagaggt gagcagtccc gggaaggggc cgagaggcgg | 120 |
| ggccgccagg tcgggcaggt gtgcgctccg ccccgccgcg cgcacagagc gctagtcctt | 180 |
| cggcgagcga gcaccttcga cgcggtccgg ggaccccctc gtcgctgtcc tcccgacgcg | 240 |
| gacccgcgtg ccccaggcct cgcgctgccc ggccggctcc tcgtgtccca ctcccggcgc | 300 |
| acgccctccc gcgagtcccg ggcccctccc gcgcccctct tctcggcgcg cgcgcagcat | 360 |
| ggcgccccg caggtcctcg cgttcgggct tctgcttgcc gcggcgacgg cgactttgc | 420 |
| cgcagctcag gaagaatgtg tctgtgaaaa ctacaagctg gccgtaaact gctttgtgaa | 480 |
| taataatcgt caatgccagt gtacttcagt tggtgcacaa atactgtca tttgctcaaa | 540 |
| gctggctgcc aaatgtttgg tgatgaaggc agaaatgaat ggctcaaaac ttgggagaag | 600 |
| agcaaaacct gaagggggccc tccagaacaa tgatgggctt tatgatcctg actgcgatga | 660 |
| gagcgggctc tttaaggcca agcagtgcaa cggcacctcc atgtgctggt gtgtgaacac | 720 |
| tgctggggtc agaagaacag acaaggacac tgaaataacc tgctctgagc gagtgagaac | 780 |
| ctactggatc atcattgaac taaaacacaa agcaagagaa aaaccttatg atagtaaaag | 840 |
| tttgcggact gcacttcaga aggagatcac aacgcgttat caactggatc aaaatttat | 900 |
| cacgagtatt ttgtatgaga ataatgttat cactattgat ctggttcaaa attcttctca | 960 |
| aaaaactcag aatgatgtgg acatagctga tgtggcttat tattttgaaa aagatgttaa | 1020 |
| aggtgaatcc ttgttttcatt ctaagaaaat ggacctgaca gtaaatgggg aacaactgga | 1080 |
| tctggatcct ggtcaaactt taatttatta tgttgatgaa aaagcacctg aattctcaat | 1140 |
| gcagggtcta aaagctggtg ttattgctgt tattgtggtt gtggtgatag cagttgttgc | 1200 |

-continued

```
tggaattgtt gtgctggtta tttccagaaa gaagagaatg gcaaagtatg agaaggctga    1260
gataaaggag atgggtgaga tgcataggga actcaatgca taactatata atttgaagat    1320
tatagaagaa gggaaatagc aaatggacac aaattacaaa tgtgtgtgcg tgggacgaag    1380
acatctttga aggtcatgag tttgttagtt taacatcata tatttgtaat agtgaaacct    1440
gtactcaaaa tataagcagc ttgaaactgg ctttaccaat cttgaaattt gaccacaagt    1500
gtcttatata tgcagatcta atgtaaaatc cagaacttgg actccatcgt taaaattatt    1560
tatgtgtaac attcaaatgt gtgcattaaa tatgcttcca cagtaaaatc tgaaaaactg    1620
atttgtgatt gaaagctgcc tttctattta cttgagtctt gtacatacat acttttttat    1680
gagctatgaa ataaaacatt ttaaactgaa tttcttaaaa aaaaaaaaa a              1731

<210> SEQ ID NO 79
<211> LENGTH: 314
<212> TYPE: PRT
<213> ORGANISM: Homo sapiens

<400> SEQUENCE: 79

Met Ala Pro Pro Gln Val Leu Ala Phe Gly Leu Leu Ala Ala Ala
1               5                   10                  15

Thr Ala Thr Phe Ala Ala Ala Gln Glu Glu Cys Val Cys Glu Asn Tyr
            20                  25                  30

Lys Leu Ala Val Asn Cys Phe Val Asn Asn Asn Arg Gln Cys Gln Cys
        35                  40                  45

Thr Ser Val Gly Ala Gln Asn Thr Val Ile Cys Ser Lys Leu Ala Ala
    50                  55                  60

Lys Cys Leu Val Met Lys Ala Glu Met Asn Gly Ser Lys Leu Gly Arg
65                  70                  75                  80

Arg Ala Lys Pro Glu Gly Ala Leu Gln Asn Asn Asp Gly Leu Tyr Asp
                85                  90                  95

Pro Asp Cys Asp Glu Ser Gly Leu Phe Lys Ala Lys Gln Cys Asn Gly
            100                 105                 110

Thr Ser Met Cys Trp Cys Val Asn Thr Ala Gly Val Arg Arg Thr Asp
        115                 120                 125

Lys Asp Thr Glu Ile Thr Cys Ser Glu Arg Val Arg Thr Tyr Trp Ile
    130                 135                 140

Ile Ile Glu Leu Lys His Lys Ala Arg Glu Lys Pro Tyr Asp Ser Lys
145                 150                 155                 160

Ser Leu Arg Thr Ala Leu Gln Lys Glu Ile Thr Thr Arg Tyr Gln Leu
                165                 170                 175

Asp Pro Lys Phe Ile Thr Ser Ile Leu Tyr Glu Asn Asn Val Ile Thr
            180                 185                 190

Ile Asp Leu Val Gln Asn Ser Ser Gln Lys Thr Gln Asn Asp Val Asp
        195                 200                 205

Ile Ala Asp Val Ala Tyr Tyr Phe Glu Lys Asp Val Lys Gly Glu Ser
    210                 215                 220

Leu Phe His Ser Lys Lys Met Asp Leu Thr Val Asn Gly Glu Gln Leu
225                 230                 235                 240

Asp Leu Asp Pro Gly Gln Thr Leu Ile Tyr Tyr Val Asp Glu Lys Ala
                245                 250                 255

Pro Glu Phe Ser Met Gln Gly Leu Lys Ala Gly Val Ile Ala Val Ile
            260                 265                 270

Val Val Val Val Ile Ala Val Val Ala Gly Ile Val Val Leu Val Ile
```

```
                275                 280                 285
Ser Arg Lys Lys Arg Met Ala Lys Tyr Glu Lys Ala Glu Ile Lys Glu
        290                 295                 300

Met Gly Glu Met His Arg Glu Leu Asn Ala
305                 310
```

ANTIGEN-BINDING MOLECULE HAVING REGULATED CONJUGATION BETWEEN HEAVY-CHAIN AND LIGHT-CHAIN

CROSS-REFERENCE TO RELATED APPLICATIONS

This application is the National Stage of International Application Serial No. PCT/JP2012/078103, filed on Oct. 31, 2012, which claims the benefit of Japanese Application Serial No. 2011-238873, filed on Oct. 31, 2011.

Sequence Listing

This application contains a Sequence Listing that has been submitted electronically as an ASCII text file named SequenceListing.txt. The ASCII text file, created on Apr. 11, 2014, is 128 kilobytes in size. The material in the ASCII text file is hereby incorporated by reference in its entirety.

BACKGROUND ART

The present invention relates to antibodies with regulated association of the heavy chain and light chain, methods for producing an antibody with regulated association of the heavy chain and light chain, methods for regulating association of the heavy chain and light chain of an antibody, pharmaceutical compositions comprising that antibody as an active ingredient, and the like.

TECHNICAL FIELD

Several methods have previously been reported as methods for preparing IgG-type bispecific antibodies having human constant regions (IgG-type antibodies having a human constant region that has binding specificity for an antigen A on one arm and binding specificity for an antigen B on the other arm). In general, IgG-type bispecific antibodies are composed of two types of H chains (namely, an H chain for antigen A and an H chain for antigen B) and two types of L chains (namely, an L chain for antigen A and an L chain for antigen B). When such IgG-type bispecific antibodies are expressed, 10 types of combinations are possible as combinations of H2L2 since two types of H chains and two types of L chains are expressed. Among these, there is one type of combination that has the desired binding specificity (IgG having binding specificity for antigen A on one arm and binding specificity for antigen B on the other arm). Consequently, in order to acquire the desired bispecific antibody, it is necessary to purify one type of antibody of interest from among ten types of antibodies, which is extremely low in efficiency and difficult.

Methods have been reported for solving this problem, which involve preferentially secreting IgG having a heterologous combination of an H chain for antigen A and an H chain for antigen B, by substituting amino acids in the CH3 region of the IgG H chain (Patent Documents 1, 2, 3 and 4, and Non-Patent Documents 1 and 2). Among these, there have been reported methods that use physical obstacles in the form of a "knob" and "hole", and those that use electric charge repulsion.

A method has also been reported for efficiently obtaining a desired molecule, which uses a common L chain in which an L chain for antigen A and an L chain for antigen B are present on a same amino acid sequence (Patent Documents 5 and 6). However, since the use of a common L chain has the potential of considerably lowering the antigen affinity, this is not necessarily the optimum method. Consequently, in order for a bispecific antibody to bind to two antigens with high affinity, it is preferable that only the L chain and H chain for antigen A associate, and only the L chain and H chain for antigen B associate. Moreover, a method has been reported to allow the H chains and L chains for each antigen to associate irrespectively of the variable regions, which comprises substituting amino acids in the CH1 and CL domains which are constant regions, instead of those in the variable regions (Patent Documents 2 and 7). However, this method is still insufficient for efficiently producing a bispecific antibody of interest.

PRIOR ART DOCUMENTS

Patent Documents

[Patent Document 1] WO 96/27011
[Patent Document 2] WO 2006/106905
[Patent Document 3] WO 2009/089004
[Patent Document 4] WO 2010/129304
[Patent Document 5] WO 98/050431
[Patent Document 6] WO 2006/109592
[Patent Document 7] WO 2007/147901

Non-Patent Documents

[Non-Patent Document 1] Ridgway J B et al., Protein Engineering, 1996, Vol. 9, p. 617-621
[Non-Patent Document 2] Merchant A M et al., Nature Biotechnology, 1998, Vol. 16, p. 677-681

SUMMARY OF THE INVENTION

Problems to be Solved by the Invention

The present invention has been achieved under such circumstances. An objective of the present invention is to provide antibodies in which association of the heavy chains and light chains is regulated, a method for producing antibodies in which the association of the heavy chains and light chains is regulated, and a method for regulating association of the heavy chains and light chains of an antibody. In addition, in one embodiment of the present invention, an objective of the present invention is to provide bispecific antibodies in which association at the interface of CH1 and CL is regulated, and a method for efficiently producing a bispecific antibody by regulating the association at the interface of CH1 and CL.

Means for Solving the Problems

The inventors of the present invention selected a constant region of the heavy chain, CH1, and a light chain constant region (CL) as heavy-chain and light-chain regions to be used for regulating association, and conducted dedicated studies on the regulation of CH1 and CL association. As a result, the present inventors found that association of CH1 and CL can be suppressed by substituting amino acid residues present at the interface of CH1 and CL with amino acid residues that mutually repel electrically or amino acid residues that do not repel, and that heterologous molecules are formed more efficiently than by using modifications which only introduce a knob and hole into CH3 as previously described.

Thus, according to findings made by the present inventors, it is possible to regulate the association of CH1 and CL.

In addition, the present invention can be applied not only to regulation of the association between CH1 and CL, but also to regulation of the association between arbitrary polypeptides.

Moreover, the present inventors also confirmed that a bispecific antibody of the present invention with regulated association of the heavy chain and light chain actually retains function.

As described above, the present inventors successfully developed antigen-binding molecules in which association of the heavy chain and light chain is regulated, and thereby completed the present invention.

The present invention relates to antigen-binding molecules in which the association of the heavy chains and light chains is regulated, methods for producing an antigen-binding molecule in which the association of the heavy chains and light chains is regulated, and methods for regulating the association of the heavy chains and light chains of an antigen-binding molecule. Specifically, the present invention relates to the following:

[1] an antigen-binding molecule in which association of the heavy chain and light chain is regulated, wherein
one set or two or more sets of amino acid residues selected from the group consisting of the sets of amino acid residues shown in (a) to (c) below in the heavy chain and light chain in the antigen-binding molecule are amino acid residues that mutually repel electrically:
(a) the amino acid residue comprised in the heavy chain constant region (CH1) at position 147 as indicated by EU numbering, and the amino acid residue comprised in the light chain constant region (CL) at position 180 as indicated by EU numbering;
(b) the amino acid residue comprised in CH1 at position 147 as indicated by EU numbering, and the amino acid residue comprised in CL at position 131 as indicated by EU numbering; and,
(c) the amino acid residue comprised in CH1 at position 175 as indicated by EU numbering, and the amino acid residue comprised in CL at position 160 as indicated by EU numbering;

[2] the antigen-binding molecule of [1], further wherein amino acid residues in the set of amino acid residues shown in (d) below are amino acid residues that mutually repel electrically:
(d) the amino acid residue comprised in CH1 at position 213 as indicated by EU numbering, and the amino acid residue comprised in CL at position 123 as indicated by EU numbering;

[3] the antigen-binding molecule of [1] or [2], wherein the amino acid residues that mutually repel electrically are selected from amino acid residues comprised in either set of (X) and (Y) below:
(X) glutamic acid (E) or aspartic acid (D); and
(Y) lysine (K), arginine (R) or histidine (H);

[4] the antigen-binding molecule of any one of [1] to [3], further wherein two or more amino acid residues forming an interface between the heavy chain variable region and light chain variable region are amino acid residues that mutually repel electrically;

[5] the antigen-binding molecule of [4], wherein the amino acid residues that mutually repel electrically are one set or two sets of amino acid residues selected from the group consisting of the sets of amino acid residues shown in (a) or (b):
(a) the amino acid residue comprised in the heavy chain variable region at position 39 as indicated by Kabat numbering and the amino acid residue comprised in the light chain variable region at position 38 as indicated by Kabat numbering; or
(b) the amino acid residue comprised in the heavy chain variable region at position 45 as indicated by Kabat numbering, and the amino acid residue comprised in the light chain variable region at position 44 as indicated by Kabat numbering;

[6] the antigen-binding molecule of [4] or [5], wherein the amino acid residues that mutually repel electrically are selected from the amino acid residues comprised in either set of (X) and (Y) below:
(X) glutamic acid (E) or aspartic acid (D); and
(Y) lysine (K), arginine (R), or histidine (H);

[7] an antigen-binding molecule in which association of the heavy chain and light chain is regulated, wherein
one set or two or more sets of amino acid residues selected from the group consisting of the sets of amino acid residues shown in (a) to (c) below in the associating heavy chain and light chain in the antigen-binding molecule are amino acid residues that do not mutually repel electrically:
(a) the amino acid residue comprised in the heavy chain constant region (CH1) at position 147 as indicated by EU numbering, and the amino acid residue comprised in the light chain constant region (CL) at position 180 as indicated by EU numbering;
(b) the amino acid residue comprised in CH1 at position 147 as indicated by EU numbering, and the amino acid residue comprised in CL at position 131 as indicated by EU numbering; and,
(c) the amino acid residue comprised in CH1 at position 175 as indicated by EU numbering, and the amino acid residue comprised in CL at position 160 as indicated by EU numbering;

[8] the antigen-binding molecule of [7], further wherein amino acid residues of the set of amino acid residues shown in (d) below are amino acid residues that do not mutually repel electrically:
(d) the amino acid residue comprised in CH1 at position 213 as indicated by EU numbering, and the amino acid residue comprised in CL at position 123 as indicated by EU numbering;

[9] the antigen-binding molecule of [7] or [8], wherein the amino acid residues that do not mutually repel electrically are amino acid residues selected from each of two sets selected from the group consisting of (X) to (Z) below, and wherein the two sets are selected from among the combinations of (X) and (Y), (X) and (Z), (Y) and (Z), and (Z) and (Z):
(X) glutamic acid (E) or aspartic acid (D);
(Y) lysine (K), arginine (R) or histidine (H); and
(Z) alanine (A), asparagine (N), cysteine (C), glutamine (Q), glycine (G), isoleucine (I), leucine (L), methionine (M), phenylalanine (F), proline (P), serine (S), threonine (T), tryptophan (W), tyrosine (Y), or valine (V);

[10] the antigen-binding molecule of any one of [7] to [9], wherein the amino acid residues that do not mutually repel electrically are the amino acid residue comprised in CH1 at position 175 as indicated by EU numbering which is lysine (K); and the amino acid residues comprised in CL at position 180, position 131, and position 160 as indicated by EU numbering which are all glutamic acid (E);

[11] the antigen-binding molecule of any one of [7] to [9], wherein the amino acid residues that do not mutually repel electrically are the amino acid residues comprised in CH1 at position 147 and position 175 as indicated by EU numbering which are glutamic acid (E); and the amino acid residues comprised in CL at position 180, position 131, and position 160 as indicated by EU numbering which are all lysine (K);

[12] the antigen-binding molecule of [11], further wherein the amino acid residue comprised in CH1 at position 213 as indicated by EU numbering is glutamic acid (E), and the amino acid residue comprised in CL at position 123 as indicated by EU numbering is lysine (K);

[13] the antigen-binding molecule of any one of [7] to [12], further wherein two or more amino acid residues forming the interface between the heavy chain variable region and light chain variable region are amino acid residues that do not mutually repel electrically;

[14] the antigen-binding molecule of [13], wherein the amino acid residues that do not mutually repel electrically are one set or two sets of amino acid residues selected from the group consisting of the sets of amino acid residues shown in (a) or (b) below:
(a) the amino acid residue comprised in the heavy chain variable region at position 39 as indicated by Kabat numbering, and the amino acid residue comprised in the light chain variable region at position 38 as indicated by Kabat numbering; or
(b) the amino acid residue comprised in the heavy chain variable region at position 45 as indicated by Kabat numbering, and the amino acid residue comprised in the light chain variable region at position 44 as indicated by Kabat numbering;

[15] the antigen-binding molecule of [13] or [14], wherein the amino acid residues that do not mutually repel electrically are amino acid residues selected from each of two sets selected from the group consisting of (X) to (Z) below, and wherein the two sets are selected from among the combinations of (X) and (Y), (X) and (Z), (Y) and (Z), and (Z) and (Z):
(X) glutamic acid (E) or aspartic acid (D);
(Y) lysine (K), arginine (R) or histidine (H); and
(Z) alanine (A), asparagine (N), cysteine (C), glutamine (Q), glycine (G), isoleucine (I), leucine (L), methionine (M), phenylalanine (F), proline (P), serine (S), threonine (T), tryptophan (W), tyrosine (Y), or valine (V);

[16] the antigen-binding molecule of any one of [1] to [15], wherein the antigen-binding molecule is a bispecific antibody;

[17] a method for producing an antigen-binding molecule in which association of the heavy chain and light chain is regulated, comprising steps of (1) to (3) below:
(1) modifying nucleic acids encoding the heavy chain constant region (CH1) and the light chain constant region (CL) so that one set or two or more sets of amino acid residues selected from the group consisting of the sets of amino acid residues shown in (a) to (c) below mutually repel electrically:
  (a) the amino acid residue comprised in CH1 at position 147 as indicated by EU numbering, and the amino acid residue comprised in CL at position 180 as indicated by EU numbering;
  (b) the amino acid residue comprised in CH1 at position 147 as indicated by EU numbering, and the amino acid residue comprised in CL at position 131 as indicated by EU numbering; and,
  (c) the amino acid residue comprised in CH1 at position 175 as indicated by EU numbering, and the amino acid residue comprised in CL at position 160 as indicated by EU numbering,
(2) introducing the modified nucleic acids into a host cell and culturing the host cell so that it expresses the nucleic acids, and
(3) collecting the antigen-binding molecule from a culture of the host cell;

[18] the method for producing an antigen-binding molecule of [17], further comprising in step (1), modifying nucleic acids so that the amino acid residues in the set of amino acid residues shown in (d) below mutually repel electrically:
(d) the amino acid residue comprised in CH1 at position 213 as indicated by EU numbering, and the amino acid residue comprised in CL at position 123 as indicated by EU numbering;

[19] the method for producing an antigen-binding molecule of [17] or [18], comprising in step (1), modifying nucleic acids so that the amino acid residues that mutually repel electrically are selected from among amino acid residues comprised in either group of (X) and (Y) below:
(X) glutamic acid (E) or aspartic acid (D); and
(Y) lysine (K), arginine (R), or histidine (H);

[20] the method for producing an antigen-binding molecule of any one of [17] to [19], further comprising in step (1), modifying nucleic acids so that two or more amino acid residues forming the interface between the heavy chain variable region and light chain variable region are amino acid residues that mutually repel electrically;

[21] the method for producing an antigen-binding molecule of [20], wherein the amino acid residues that mutually repel electrically are amino acid residues of any one set selected from the group consisting of the sets of amino acid residues shown in (a) or (b) below:
(a) the amino acid residue comprised in the heavy chain variable region at position 39 as indicated by Kabat numbering, and the amino acid residue comprised in the light chain variable region at position 38 as indicated by Kabat numbering; or
(b) the amino acid residue comprised in the heavy chain variable region at position 45 as indicated by Kabat numbering, and the amino acid residue comprised in the light chain variable region at position 44 as indicated by Kabat numbering;

[22] the method for producing an antigen-binding molecule of [20] or [21], wherein the amino acid residues that mutually repel electrically are selected from amino acid residues comprised in either set of (X) and (Y) below:
(X) glutamic acid (E) or aspartic acid (D); and
(Y) lysine (K), arginine (R), or histidine (H);

[23] a method for producing an antigen-binding molecule in which association of the heavy chain and light chain is regulated, comprising the following steps of (1) to (3):
(1) modifying nucleic acids encoding a heavy chain constant region (CH1) and a light chain constant region (CL) so that one set or two or more sets of amino acid residues selected from the group consisting of the sets of amino acid residues shown in (a) to (c) below do not mutually repel electrically:
  (a) the amino acid residue comprised in the heavy chain constant region (CH1) at position 147 as indicated by EU numbering, and the amino acid residue comprised in the light chain constant region (CL) at position 180 as indicated by EU numbering;
  (b) the amino acid residue comprised in CH1 at position 147 as indicated by EU numbering, and the amino acid residue comprised in CL at position 131 as indicated by EU numbering; and,
  (c) the amino acid residue comprised in CH1 at position 175 as indicated by EU numbering, and the amino acid residue comprised in CL at position 160 as indicated by EU numbering, (2) introducing the modified nucleic acids into a host cell and culturing the host cell so that it expresses the nucleic acids, and
(3) collecting the antigen-binding molecule from a culture of the host cell;

[24] the method for producing an antigen-binding molecule of [23], further comprising in step (1), modifying nucleic acids so that the amino acid residues in the set of amino acid residues shown in (d) below do not mutually repel electrically:
(d) the amino acid residue comprised in CH1 at position 213 as indicated by EU numbering, and the amino acid residue comprised in CL at position 123 as indicated by EU numbering;

[25] the method for producing an antigen-binding molecule of [23] or [24], comprising in step (1), modifying the nucleic acids so that the amino acid residues that do not mutually repel electrically are amino acids residues selected from each of two sets selected from the group consisting of (X) to (Z) below, and wherein the two sets are selected from among the combinations of (X) and (Y), (X) and (Z), (Y) and (Z), and (Z) and (Z):
(X) glutamic acid (E) or aspartic acid (D);
(Y) lysine (K), arginine (R), or histidine (H); and
(Z) alanine (A), asparagine (N), cysteine (C), glutamine (Q), glycine (G), isoleucine (I), leucine (L), methionine (M), phenylalanine (F), proline (P), serine (S), threonine (T), tryptophan (W), tyrosine (Y), or valine (V);

[26] the method for producing an antigen-binding molecule of any one of [23] to [25], comprising in step (1), modifying nucleic acids so that the amino acid residues that do not mutually repel electrically are the amino acid residue comprised in CH1 at position 175 as indicated by EU numbering which is lysine (K), and the amino acid residues comprised in CL at position 180, position 131, and position 160 as indicated by EU numbering which are all glutamic acid (E);

[27] the method for producing an antigen-binding molecule of any one of [23] to [25], comprising in step (1), modifying nucleic acids so that the amino acid residues that do not mutually repel electrically are the amino acid residues comprised in CH1 at position 147 and position 175 as indicated by EU numbering which are glutamic acid (E), and the amino acid residues comprised in CL at position 180, position 131, and position 160 as indicated by EU numbering which are all lysine (K);

[28] the method for producing an antigen-binding molecule of [27], further comprising modifying nucleic acids so that the amino acid residue comprised in CH1 at position 213 as indicated by EU numbering is glutamic acid (E), and the amino acid residue comprised in CL at position 123 as indicated by EU numbering is lysine (K);

[29] the method for producing an antigen-binding molecule of any one of [23] to [28], further comprising in step (1), modifying nucleic acids so that two or more amino acid residues forming the interface between the heavy chain variable region and light chain variable region are amino acid residues that do not mutually repel electrically;

[30] the method for producing an antigen-binding molecule of [29], wherein the amino acid residues that do not mutually repel electrically are amino acid residues of any one set selected from the group consisting of the sets of amino acid residues shown in (a) or (b) below:
(a) the amino acid residue comprised in the heavy chain variable region at position 39 as indicated by Kabat numbering, and the amino acid residue comprised in the light chain variable region at position 38 as indicated by Kabat numbering; or
(b) the amino acid residue comprised in the heavy chain variable region at position 45 as indicated by Kabat numbering, and the amino acid residue comprised in the light chain variable region at position 44 as indicated by Kabat numbering;

[31] the method for producing an antigen-binding molecule of [29] or [30], wherein the amino acid residues that do not mutually repel electrically are amino acid residues selected from each of two sets selected from the group consisting of (X) to (Z) below, and wherein the two sets are selected from among the combinations of (X) and (Y), (X) and (Z), (Y) and (Z), and (Z) and (Z):
(X) glutamic acid (E) or aspartic acid (D);
(Y) lysine (K), arginine (R) or histidine (H); and
(Z) alanine (A), asparagine (N), cysteine (C), glutamine (Q), glycine (G), isoleucine (I), leucine (L), methionine (M), phenylalanine (F), proline (P), serine (S), threonine (T), tryptophan (W), tyrosine (Y), or valine (V);

[32] an antigen-binding molecule produced according to the method for producing an antigen-binding molecule of any one of [17] to [31];

[33] the antigen-binding molecule of [32], wherein the antigen-binding molecule is a bispecific antibody;

[34] a method for regulating association of the heavy chain and light chain of an antigen-binding molecule, comprising:
modifying nucleic acids so that one set or two or more sets of amino acid residues selected from the group consisting of the sets of amino acid residues shown in (a) to (c) below are amino acid residues that mutually repel electrically:
(a) the amino acid residue comprised in CH1 at position 147 as indicated by EU numbering, and the amino acid residue comprised in CL at position 180 as indicated by EU numbering;
(b) the amino acid residue comprised in CH1 at position 147 as indicated by EU numbering, and the amino acid residue comprised in CL at position 131 as indicated by EU numbering; and
(c) the amino acid residue comprised in CH1 at position 175 as indicated by EU numbering, and the amino acid residue comprised in CL at position 160 as indicated by EU numbering;

[35] the method of [34], further comprising modifying nucleic acids so that the amino acid residues in the set of amino acid residues shown in (d) below are amino acid residues that mutually repel electrically:
(d) the amino acid residue comprised in CH1 at position 213 as indicated by EU numbering, and the amino acid residue comprised in CL at position 123 as indicated by EU numbering;

[36] the method of [34] or [35], wherein the amino acid residues that mutually repel electrically are selected from amino acid residues comprised in either set of (X) and (Y) below:
(X) glutamic acid (E) or aspartic acid (D); and
(Y) lysine (K), arginine (R), or histidine (H);

[37] the method of any one of [34] to [36], further wherein two or more amino acid residues forming the interface between the heavy chain variable region and light chain variable region are amino acid residues that mutually repel electrically;

[38] the method of [37], wherein the amino acid residues that mutually repel electrically are amino acid residues of any one set selected from the group consisting of the sets of amino acid residues shown in (a) or (b) below:
(a) the amino acid residue comprised in the heavy chain variable region at position 39 as indicated by Kabat numbering, and the amino acid residue comprised in the light chain variable region at position 38 indicated according to the Kabat numbering; or
(b) the amino acid residue comprised in the heavy chain variable region at position 45 as indicated by Kabat numbering, and the amino acid residue comprised in the light chain variable region at position 44 as indicated by Kabat numbering;

[39] the method of [37] or [38], wherein the amino acid residues that mutually repel electrically are selected from amino acid residues comprised in either set of (X) and (Y) below:
(X) glutamic acid (E) or aspartic acid (D); and
(Y) lysine (K), arginine (R), or histidine (H);

[40] a method for regulating association of the heavy chain and light chain of an antigen-binding molecule, comprising:
modifying nucleic acids so that one set or two or more sets of amino acid residues selected from the group consisting of the sets of amino acid residues shown in (a) to (c) below are amino acid residues that do not mutually repel electrically:
(a) the amino acid residue comprised in CH1 at position 147 as indicated by EU numbering, and the amino acid residue comprised in CL at position 180 as indicated by EU numbering;
(b) the amino acid residue comprised in CH1 at position 147 as indicated by EU numbering, and the amino acid residue comprised in CL at position 131 as indicated by EU numbering; and,
(c) the amino acid residue comprised in CH1 at position 175 as indicated by EU numbering, and the amino acid residue comprised in CL at position 160 as indicated by EU numbering;

[41] the method of [40], further comprising modifying nucleic acids so that the amino acid residues in the set of amino acid residues shown in (d) below are amino acid residues that do not mutually repel electrically:
(d) the amino acid residue comprised in CH1 at position 213 as indicated by EU numbering, and the amino acid residue comprised in CL at position 123 as indicated by EU numbering;

[42] the method of [40] or [41], wherein the amino acid residues that do not mutually repel electrically are amino acid residues selected from each of two sets selected from the group consisting of (X) to (Z) below, and wherein the two sets are selected from among the combinations of (X) and (Y), (X) and (Z), (Y) and (Z), and (Z) and (Z):
(X) glutamic acid (E) or aspartic acid (D);
(Y) lysine (K), arginine (R), or histidine (H); and
(Z) alanine (A), asparagine (N), cysteine (C), glutamine (Q), glycine (G), isoleucine (I), leucine (L), methionine (M), phenylalanine (F), proline (P), serine (S), threonine (T), tryptophan (W), tyrosine (Y), or valine (V);

[43] the method of any one of [40] to [42], wherein the amino acid residues that do not mutually repel electrically are the amino acid residue comprised in CH1 at position 175 as indicated by EU numbering which is lysine (K), and the amino acid residues comprised in CL at position 180, position 131, and position 160 as indicated by EU numbering which are all glutamic acid (E);

[44] the method of any one of [40] to [42], wherein the amino acid residues that do not mutually repel electrically are the amino acid residues comprised in CH1 at position 147 and position 175 as indicated by EU numbering which are glutamic acid (E), and the amino acid residues comprised in CL at position 180, position 131, and position 160 as indicated by EU numbering which are all lysine (K);

[45] the method of [44], further wherein the amino acid residue contained in CH1 at position 213 as indicated by EU numbering is glutamic acid (E), and the amino acid residue contained in CL at position 123 as indicated by EU numbering is lysine (K);

[46] the method of any one of [34] to [45], wherein the antigen-binding molecule is a bispecific antibody;

[47] a composition containing the antigen-binding molecule of any one of [1] to [16], [32], and [33], and a pharmaceutically acceptable carrier;

[48] a nucleic acid encoding the antigen-binding molecule of any one of [1] to [16], [32], and [33]; and

[49] a host cell having the nucleic acid of [48].

BRIEF DESCRIPTION OF THE DRAWINGS

FIG. 9-1 depicts graphs showing the results of COAX analysis of each of the antibodies.

FIG. 9-2 is a continuation of FIG. 9-1.

FIG. 12 is a diagram comparing the H chain CH1 by aligning the amino acid sequences of human IgA1 (SEQ ID NO: 63), IgA2 (SEQ ID NO: 64), IgD (SEQ ID NO: 65), IgE (SEQ ID NO: 66), IgG1 (SEQ ID NO: 67), IgG2 (SEQ ID NO: 68), IgG3 (SEQ ID NO: 69), IgG4 (SEQ ID NO: 70), and IgM (SEQ ID NO: 71); and the L chain CL by aligning the amino acid sequences of human IgK (Kappa) (SEQ ID NO: 72), IgL1 (SEQ ID NO: 73), IgL2 (SEQ ID NO: 74), IgL3 (SEQ ID NO: 75), IgL6 (SEQ ID NO: 76), IgL7 (SEQ ID NO: 77) (Lambda).

MODE FOR CARRYING OUT THE INVENTION

Figure 1:
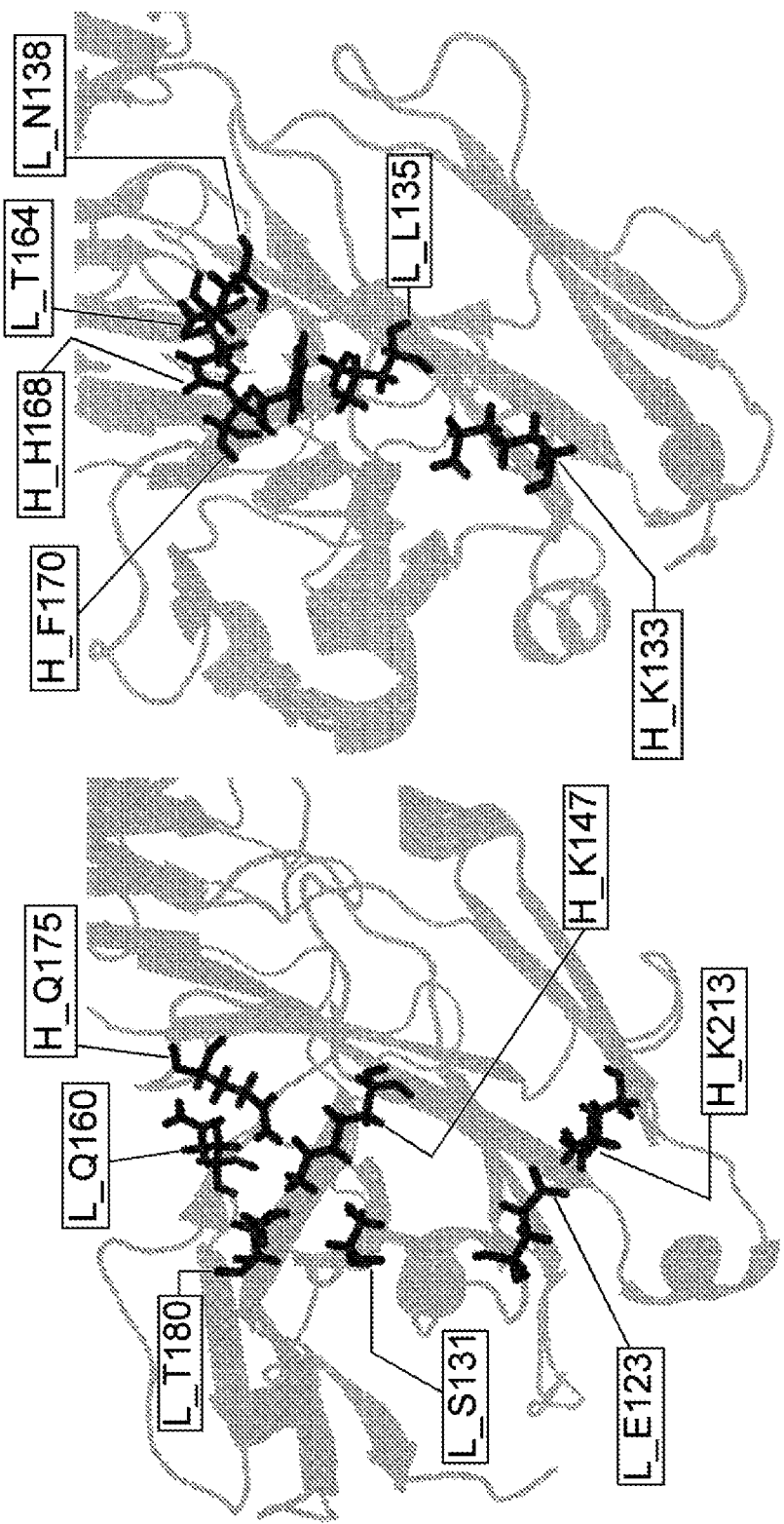
FIG. 1 is a model diagram of an CH1/CL interface.

The present invention relates to antibodies in which the association of the heavy chains and light chains is regulated, methods for producing an antibody in which the association of the heavy chains and light chains is regulated, and methods for regulating the association of the heavy chains and light chains of an antibody.

In the present invention, the term "antibody" is used synonymously with "antigen-binding molecule". That is, in the present invention, the terms "antibody" and "antigen-binding molecule" are used in the broadest sense, and include monoclonal antibodies, polyclonal antibodies, and antibody variants (such as chimeric antibodies, humanized antibodies, low molecular weight antibodies (including antibody fragments to which other molecules may be added arbitrarily), and polyspecific antibodies) provided that they demonstrate the desired antigen-binding activity or biological activity. An example of an "antibody" or "antigen-binding molecule" in the present invention is a molecule in which an HAS-binding scaffold has been added to the Fab (an antibody in which only the Fab portion is normal). In addition, in the present invention, an "antibody" may also be a polypeptide or a heteromeric multimer. Preferred antibodies are monoclonal antibodies, chimeric antibodies, humanized antibodies, human antibodies, Fc-fusion antibodies and low molecular weight antibodies such as antibody fragments.

The antibody of the present invention is an antibody in which the association of the heavy chain and light chain is regulated, in which the heavy chain and light chain constituting the antibody are a combination of heavy chain and light chain of interest, and in which the amino acid residues at given locations in the constant region of the heavy chain (CH1) and the constant region of the light chain are mutually electrically repelling amino acid residues (having the same charge).

In the present invention, by making amino acid residues at given locations in the constant region of the heavy chain (CH1) and constant region of the light chain of an undesired combination of heavy chain and light chain into amino acid residues that mutually repel electrically (i.e., that have the same charge), the formation of undesired combinations of heavy chain and light chain can be prevented by utilizing this charge repulsion, and as a result, the desired combination of heavy chain and light chain can be formed.

In another embodiment, the antibody of the present invention is an antibody in which the association of the heavy chain and light chain is regulated, in which the heavy chain and light chain constituting the antibody associate as a combination of heavy chain and light chain of interest, and in which the amino acid residues at given locations in the constant region of the heavy chain (CH1) and in the constant region of the light chain do not mutually repel electrically. By making amino acid residues at given locations in the heavy chain constant region (CH1) and the light chain constant region of a desired combination of heavy chain and light chain into amino acid residues that do not mutually repel electrically, a desired combination of heavy chain and light chain can be formed, for example, by using the attractive force of the electric charges.

In the present invention, the term "polypeptide" generally refers to peptides and proteins whose length is about ten amino acids or longer. Polypeptides are ordinarily derived from organisms but are not particularly limited thereto, and for example, they may be composed of an artificially designed sequence. They may also be any of naturally derived polypeptides, synthetic polypeptides, recombinant polypeptides, or such. Additionally, fragments of the above-mentioned polypeptides are also included in the polypeptides of the present invention.

In the present invention, the phrases "to regulate association" and "association is regulated" refer to regulating to achieve a desired association condition, and more specifically refers to regulating so that undesirable associations are not formed between the heavy chain and light chain.

In the present invention, the term "interface" generally refers to the association surface that results from association (interaction), and amino acid residues that form the interface are ordinarily one or more amino acid residues included in the polypeptide regions which participate in the association, and are more preferably amino acid residues that approach each other during association and are involved in the interaction. More specifically, this interaction includes, for example, instances where the amino acid residues come close during the association to form hydrogen bonds, electrostatic interactions, or salt bridges with each other.

In the present invention, the phrase, "amino acid residues forming an interface" more specifically refers to amino acid residues included in the polypeptide region that constitutes the interface. For example, polypeptide regions constituting the interface refer to polypeptide regions responsible for selective binding between molecules such as in antibodies, ligands, receptors, or substrates. More specifically, in antibodies, such examples include heavy chain constant regions, heavy chain variable regions, light chain constant regions, and light chain variable regions.

"Modification" of amino acid residues in the present invention specifically refers to substituting original amino acid residue(s) for other amino acid residue(s), deleting original amino acid residue(s), adding new amino acid residue(s), and such, but preferably refers to substituting one or more original amino acid residues for other amino acid residues.

In a preferred embodiment of the antibody of the present invention, the antibody has amino acid residues at given locations in the heavy chain constant region (CH1) and light chain constant region of an undesired combination of heavy chain and light chain before association regulation which electrically repel (which have the same charge).

By modifying amino acid residues in the aforementioned antibody into amino acid residues that mutually repel electrically (have the same charge), association of these amino acid residues is thought to be inhibited by the repulsive force of electrical charges.

In another preferred embodiment of the antibody of the present invention, the antibody has amino acid residues involved in association at the interface of polypeptides that do not mutually repel electrically.

In the aforementioned antibody, by modifying amino acid residues involved in association at the interface of polypeptides into amino acid residues that do not mutually repel electrically, association of these amino acid residues is thought to be promoted by, for example, the attractive force of their electrical charges.

Thus, in the aforementioned antibody, the modified amino acid residues are preferably amino acid residues that approach each other at association, in the polypeptide regions forming the interface.

The amino acid residues that approach during association can be determined by, for example, analyzing the three-dimensional structure of a polypeptide, and investigating the amino acid sequences of the polypeptide regions that form an interface during polypeptide association. Amino acid residues at the interface that mutually approach each other are preferable targets of "modification" in the antibody of the present invention.

Some amino acids are known to be electrically charged. In general, lysine (K), arginine (R) and histidine (H) are known to be amino acids having a positive charge (positively charged amino acids). Aspartic acid (D), glutamic acid (E), and such are known to be amino acids having a negative charge (negatively charged amino acids). In addition, alanine (A), asparagine (N), cysteine (C), glutamine (Q), glycine (G), isoleucine (I), leucine (L), methionine (M), phenylalanine (F), proline (P), serine (S), threonine (T), tryptophan (W), tyrosine (Y), valine (V), and the like are known to be amino acids that do not have a charge, or nonpolar amino acids.

Thus, amino acids that mutually repel electrically (have the same charge) in the present invention refer to:
(1) amino acids in which one of the amino acids is a positively charged amine acid and the other amino acid is also a positively charged amino acid, and
(2) amino acids in which one of the amino acids is a negatively charged amino acid and the other amino acid is also a negatively charged amino acid.

Further, amino acids that do not mutually repel electrically in the present invention refer to:
(1) amino acids in which one of the amino acids is a positively charged amino acid and the other amino acid is a negatively charged amino acid,
(2) amino acids in which one of the amino acids is a positively charged amino acid and the other amino acid is an uncharged amino acid or a nonpolar amino acid,
(3) amino acids in which one of the amino acids is a negatively charged amino acid and the other amino acid is an uncharged amino acid or a nonpolar amino acid, and
(4) amino acids in which both of the amino acids are uncharged amino acids or nonpolar amino acids.

Amino acids can be modified according to various methods known in the field of the art. Examples of these methods include, but are not limited to site-directed mutagenesis (Hashimoto-Gotoh, T., Mizuno, T., Ogasahara, Y. and Nakagawa, M. (1995) An oligodeoxyribonucleotide-directed dual amber method for site-directed mutagenesis, Gene 152, 271-275; Zoller, M. J. and Smith, M. (1983) Oligonucleotide-directed mutagenesis of DNA fragments cloned into M13 vectors, Methods Enzymol. 100, 468-500; Kramer, W., Drutsa, V., Jansen, H. W., Kramer, B., Pflugfelder, M. and Fritz, H. J. (1984) The gapped duplex DNA approach to oligonucleotide-directed mutation construction, Nucleic Acids Res. 12, 9441-9456; Kramer, W. and Fritz, H. J. (1987) Oligonucleotide-directed construction of mutations via gapped duplex DNA, Methods Enzymol. 154, 350-367; Kunkel, T. A. (1985) Rapid and efficient site-specific mutagenesis without phenotypic selection, Proc. Natl. Acad. Sci. USA 82, 488-492), PCR mutagenesis, cassette mutagenesis, etc.

Examples of amino acid modifications include modification of an uncharged amino acid or a nonpolar amino acid into a positively charged amino acid, modification of an uncharged amino acid or a nonpolar amino acid into a negatively charged amino acid, modification of a positively charged amino acid into a negatively charged amino acid, and modification of a negatively charged amino acid into a positively charged amino acid. Furthermore, modification of an uncharged amino acid or a nonpolar amino acid into a different uncharged or nonpolar amino acid, modification of a positively charged amino acid into a different positively charged amino acid, and modification of a negatively charged amino acid into a different negatively charged amino acid are also included in the amino acid modifications of the present invention.

Modifying amino acids in the present invention includes making one modification in each of the heavy and light chain, or making multiple modifications to each of the heavy and light chain. In addition, the number of modifications added to the heavy chain and light chain may be the same or different.

Modifying amino acids in the present invention includes making multiple modifications into positively charged amino acids on either the heavy chain or light chain, and making multiple modifications into negatively charged amino acids on the other chain. Moreover, multiple modifications into positively charged amino acids as well as multiple modifications into negatively charged amino acids may be made on the same heavy chain or light chain. In these modifications, modifications into uncharged amino acids or nonpolar amino acids as well as modifications of uncharged amino acids or nonpolar amino acids may also be suitably combined.

In the modifications of the present invention, for example, the amino acids on one of the chains can be used as they are without being modified, and in such cases, the heavy chain and light chain do not need to be both modified, and only one of the chains may be modified.

Although there are no particular limitations to the number of amino acid residues subjected to modification in the antibody of the present invention, for example, when modifying the constant region of the antibody, in order not to reduce the binding activity toward the antigen and not to increase immunogenicity, it is preferable to modify as few amino acid residues as possible. The aforementioned "few" refers to, for example, a number of about 1 to 30, preferably a number of about 1 to 20, even more preferably a number of about 1 to 15, and most preferably a number of 1 to 5.

In the present invention, the term "antibody" is used in the broadest sense, and includes monoclonal antibodies, polyclonal antibodies, antibody variants (such as chimeric antibodies, humanized antibodies, low molecular weight antibodies (including antibody fragments), and polyspecific antibodies) as long as they demonstrate the desired biological activity. In addition, the "antibody" in the present invention may be either a polypeptide or a heteromeric multimer. Preferred antibodies are monoclonal antibodies, chimeric antibodies, humanized antibodies, human antibodies, Fc-fusion antibodies, and low molecular weight antibodies such as antibody fragments.

In the context of the present invention, the term "multispecific antibody" (used in the present description to have the same meaning as "polyspecific antibody") refers to an antibody that may bind specifically to different types of epitopes. More specifically, multispecific antibodies are antibodies having specificity to at least two different types of epitopes, and, in addition to antibodies recognizing different antigens, antibodies recognizing different epitopes on the same antigen are also included. (For example, when the antigens are heterologous receptors, multispecific antibodies can recognize different domains constituting the heterologous receptors; alternatively, when the antigens are monomers, multispecific antibodies recognize multiple sites on the monomer antigens.) Ordinarily, such molecules bind to two antigens (bispecific antibodies; used in the present description to have the same meaning as "dual-specific antibodies"), but they may even have specificity toward more antigens (for example three types).

In addition to the antibodies described above, the antibodies of the present invention include antibodies whose amino acid sequences have been modified by amino acid substitutions, deletions, additions, and/or insertions, or chimerization, humanization, and such. Such amino acid sequence modifications, such as amino acid substitutions, deletions, additions, and/or insertions, and humanization and chimerization, can be achieved by methods known to those skilled in the art. When the antibodies of the present invention are prepared as recombinant antibodies, likewise, the amino acid sequences of the antibody variable and constant regions may also be modified by amino acid substitutions, deletions, additions, and/or insertions, or chimerization, humanization and the like.

The antibodies of the present invention may be derived from any animal, such as a mouse, human, rat, rabbit, goat, or camel. Furthermore, the antibodies may be modified, for example, chimeric antibodies, and in particular, modified antibodies that include amino acid substitutions in their sequence, such as humanized antibodies. The antibodies may be any type of antibody, such as antibody modification products linked with various molecules, antibody fragments, and low molecular weight antibodies.

"Chimeric antibodies" are antibodies prepared by combining sequences derived from different animals. An example is an antibody having heavy and light chain variable (V) regions from a mouse antibody and heavy and light chain constant (C) regions from a human antibody. Chimeric antibodies can be prepared by known methods. To obtain such chimeric antibodies, for example, a DNA encoding an antibody V region may be ligated with a DNA encoding a human antibody constant region; the resulting ligation product can be inserted into an expression vector; and the construct can be introduced into a host to produce the chimeric antibody.

"Humanized antibodies" are also referred to as reshaped human antibodies, and can be obtained by substituting the complementarity determining region (CDR) of a human antibody for the CDR of an antibody derived from a non-human mammal, for example, a mouse. Methods for identifying CDRs are known in the art (Kabat et al., Sequence of Proteins of Immunological Interest (1987), National Institute of Health, Bethesda, Md.; Chothia et al., Nature (1989) 342:877). General genetic recombination techniques suitable for this purpose are also known (see European Patent Application Publication No. EP 125023; and WO 96/02576). For example, the CDR of a mouse antibody can be determined by known methods, and a DNA can be prepared such that it encodes an antibody in which the CDR is ligated with the framework region (FR) of a human antibody. A humanized antibody can then be produced using a system that uses conventional expression vectors. Such DNAs can be synthesized by PCR, using as primers several oligonucleotides designed to include portions that overlap the ends of both the CDR and FR regions (see the method described in WO 98/13388). Human antibody FRs linked via CDRs are selected such that the CDRs form a suitable antigen binding site. If required, amino acids in the FRs of an antibody variable region may be modified so that the CDRs of the reshaped human antibody can form a suitable antigen binding site (Sato, K. et al., Cancer Res. (1993) 53:851-856). Modifiable amino acid residues in the FRs include portions that directly bind to an antigen via non-covalent bonds (Amit et al., Science (1986) 233: 747-53), portions that have some impact or effect on the CDR structure (Chothia et al., J. Mol. Biol. (1987) 196: 901-17), and portions involved in the interaction between VH and VL (EP 239400).

The heavy chain constant region of the antibody of the present invention is preferably a human heavy chain constant region. In addition, examples of antibody heavy chain constant regions include IgA1, IgA2, IgD, IgE, IgG1, IgG2, IgG3, IgG4 and IgM type constant regions. The heavy-chain constant region of the antibody of the present invention is preferably an IgG1 type constant region, and particularly preferably a human IgG1 constant region, but it is not limited thereto. Several allotype sequences obtained by genetic polymorphism are described in Sequences of Proteins of Immunological Interest, NIH Publication No. 91-3242 as human IgG1 constant region, and any of these may be used in the present invention.

Moreover, the light chain constant region of the antibody of the present invention is preferably a human light chain constant region. Examples of antibody light chain constant region include IgK (Kappa), IgL1, IgL2, IgL3, IgL6 and IgL7 (Lambda) type constant regions. The light chain constant region of the antibody of the present invention is preferably a human IgK (Kappa) constant region, but is not limited thereto. The amino acid sequence of the human IgK (Kappa) constant region is known (SEQ ID NO: 72). Several allotype sequences obtained by genetic polymorphism are described in Sequences of Proteins of Immunological Interest, NIH Publication No. 91-3242 as human IgK (Kappa) constant region and human IgL7 (Lambda) constant region, and any of these may be used in the present invention.

Antibody constant regions, in particular, heavy chain constant regions, may be modified as necessary in order to improve antibody function or antibody stability. Examples of modifications for improving antibody function include modifications that strengthen or weaken the binding between an antibody and an Fcγ receptor (FcγR), modifications that strengthen or weaken the binding between an antibody and FcRn, modifications that strengthen or weaken antibody cytotoxic activity (such as ADCC activity and CDC activity), and such. In addition, modifications that improve antibody heterogeneity and modifications that improve immunogenicity and/or pharmacokinetics may also be included.

Moreover, as the heterogeneity of the heavy chain C-terminal sequence of the IgG antibody, amidation of the C-terminal carboxyl group by deletion of the C-terminal amino acid, lysine residue, or by deletion of the two C-terminal amino acids, glycine and lysine, has been reported the (Anal. Biochem. 2007 Jan. 1:360(1):75-83). Thus, in the present invention, to lower heterogeneity of the heavy chain C terminus, it is preferable to use an IgG in which the C-terminal lysine or the C-terminal lysine and glycine have been deleted.

Since their antigenicity in the human body has been attenuated, chimeric and humanized antibodies using human-derived sequences are expected to be useful when administered to humans for therapeutic purposes or such.

Moreover, low molecular weight antibodies are useful as the antibodies because of their in vivo kinetic characteristics and low-cost production using *E. coli*, plant cells, or such.

Antibody fragments are one type of low molecular weight antibody. The term "low molecular weight antibody" includes antibodies that include an antibody fragment as a partial structural unit. The low molecular weight antibodies of the present invention are not particularly limited by their structure nor their method of production, so long as they have antigen binding activity. Some low molecular weight antibodies have an activity greater than that of a whole antibody (Orita et al., Blood (2005) 105:562-566). Herein, the "antibody fragments" are not particularly limited, so long as they are a portion of a whole antibody (for example, whole IgG). However, the antibody fragments preferably include a heavy chain variable region (VH) or a light chain variable region (VL), and further include CH1 or CL. Examples of preferred antibody fragments are: Fab, F(ab')$_2$, and Fab'. The amino acid sequences of a VH, VL, CH1, and CL in an antibody fragment may be modified by substitution, deletion, addition, and/or insertion. Furthermore, some portions of a CH1, CL, VH, and VL may be deleted, so long as the resulting fragments retain their antigen binding ability, and antibody fragments such as scFv, Fab, domain antibody (dAb), and VHH, HAS binding scaffold, PEG, albumin, cytokines, toxins, and the like (the molecules described in Biodrugs, 2009, 23(2):93-109; Methods Mol. Med., 2005, 109:347-74; AAPS J., 2006 Aug. 18, 8(3):E532-51; etc.) may also be added to increase the pharmacokinetics (PK) or drug efficacy.

An antibody fragment can be prepared by treating an antibody with an enzyme, for example, a protease such as papain or pepsin (see Morimoto et al., J. Biochem. Biophys. Methods (1992) 24: 107-17; Brennan et al., Science (1985) 229:81). Alternatively, antibody fragments can also be produced by genetic recombination based on their amino acid sequence.

A low molecular weight antibody having a structure that results from modification of an antibody fragment can be prepared using antibody fragments obtained by enzyme treatment or genetic recombination. Alternatively, after constructing a gene which encodes a whole low molecular weight antibody, and introducing the construct into an expression vector, the low molecular weight antibody may be expressed in appropriate host cells (see, for example, Co et al., J. Immunol. (1994) 152: 2968-76; Better and Horwitz, Methods Enzymol. (1989) 178: 476-96; Pluckthun and Skerra, Methods Enzymol. (1989) 178: 497-515; Lamoyi, Methods Enzymol. (1986) 121: 652-63; Rousseaux et al., Methods Enzymol. (1986) 121: 663-9; Bird and Walker, Trends Biotechnol. (1991) 9: 132-7).

A preferred example of the antibody of the present invention is a heteromeric multimer having two or more types of CH1 and two or more types of CL. This heteromeric multimer preferably recognizes two or more types of epitopes, and an example thereof is a polyspecific antibody.

A preferred example of a polyspecific antibody of the present invention is a bispecific antibody. Thus, an example of a preferred embodiment of the antibody of the present invention is a bispecific antibody composed of two types of heavy chains (a first heavy chain and a second heavy chain) and two types of light chains (a first light chain and a second light chain).

Describing the "bispecific antibodies" of the preferred embodiments of the antibodies of the present invention more precisely, the above-mentioned "first heavy chain" refers to one of the two heavy chains (H chains) forming the antibody, and the "second H chain" refers to the other H chain that is different from the first H chain. That is, of the two H chains, one of them can be arbitrarily defined as the first H chain and the other can be defined as the second H chain. Similarly, the "first light chain" refers to one of the two light chains (L chains) forming the bispecific antibody, and the "second L chain" refers to the other L chain that is different from the first L chain. Of the two L chains, one of them can be arbitrarily defined as the first L chain and the other can be defined as the second L chain. Ordinarily, the first L chain and the first H chain are derived from a same antibody that recognizes a certain antigen (or epitope), and the second L chain and the second H chain are also derived from a same antibody that recognizes a certain antigen (or epitope). Herein, the L chain-H chain pair formed by the first H chain and L chain is called the first pair, and the L chain-H chain pair formed by the second H chain and L chain is called the second pair. The antigen (or epitope) used to produce the antibody from which the second pair derives is preferably different from the antigen used to produce the antibody from which the first pair derives. More specifically, antigens recognized by the first pair and the second pair may be the same, but preferably, the pairs recognize different antigens (or epitopes). In this case, the H chains and L chains of the first pair and second pair preferably have amino acid sequences that differ from each other. When the first pair and the second pair recognize different epitopes, the first pair and the second pair may recognize a completely different antigen, or they may recognize different sites (different epitopes) on the same antigen. Furthermore, one of them may recognize an antigen such as a protein, peptide, gene, or sugar, and the other may recognize cytotoxic substances such as radioactive substances, chemotherapeutic agents, or cell-derived toxins. However, when one wishes to produce an antibody having pairs formed by specific combinations of H chains and L chains, those specific H chains and L chains may be arbitrary determined to be the first pair and second pair.

As for the genes encoding the H chain or L chain of antibodies before introduction of mutations in the present invention (herein, it may be simply referred to as "an antibody of the present invention"), known sequences can be used, or they can be obtained by methods known to those skilled in the art. For example, they may be obtained from an antibody library, or they may be obtained by cloning genes encoding the antibody from hybridomas producing monoclonal antibodies.

Regarding antibody libraries, many antibody libraries are already well known, and since methods for producing antibody libraries are known, those skilled in the art can appropriately obtain antibody libraries. For example, regarding antibody phage libraries, one can refer to the literature such as Clackson et al., Nature 1991, 352: 624-8; Marks et al., J. Mol. Biol. 1991, 222: 581-97; Waterhouses et al., Nucleic Acids Res. 1993, 21: 2265-6; Griffiths et al., EMBO J. 1994, 13: 3245-60; Vaughan et al., Nature Biotechnology 1996, 14: 309-14; and Japanese Patent Kohyo Publication No. (JP-A) H10-504970 (unexamined Japanese national phase publication corresponding to a non-Japanese international publication). In addition, known methods, such as methods that use eukaryotic cells as libraries (WO95/15393) and ribosome display methods, may be used. Furthermore, techniques to obtain human antibodies by panning using human antibody libraries are also known. For example, variable regions of human antibodies can be expressed on the surface of phages as single chain antibodies (scFvs) using phage display methods, and phages that bind to antigens can be selected. Genetic analysis of the selected phages can determine the DNA sequences encoding the variable regions of human antibodies that bind to the antigens. Once the DNA sequences of scFvs that bind to the antigens is revealed, suitable expression vectors can be produced based on these sequences to obtain human antibodies. These methods are already well known, and one can refer to WO92/01047, WO92/20791, WO93/06213, WO93/11236, WO93/19172, WO95/01438, and WO95/15388.

As for methods for obtaining genes encoding antibodies from hybridomas, known techniques may be basically used, which involve using of desired antigens or cells expressing the desired antigens as sensitizing antigens, using these to perform immunizations according to conventional immunization methods, fusing the immune cells thus obtained with known parent cells by ordinary cell fusion methods, screening monoclonal antibody producing cells (hybridomas) by ordinary screening methods, synthesizing cDNAs of antibody variable regions (V regions) from mRNAs of the obtained hybridomas using reverse transcriptase, and linking them with DNAs encoding the desired antibody constant regions.

The sensitizing antigens for obtaining the aforementioned antibody genes encoding the H chain and L chain are not particularly limited to the examples described below, but include both complete antigens having immunogenicity and incomplete antigens including haptens and the like that do not demonstrate immunogenicity. There are no particular limitations on the antigen for the antibodies of the present invention, and for example, a full-length protein or a partial peptide of a target protein, as well as substances composed of polysaccharides, nucleic acids, lipids, and the like that are known to be able to serve as an antigen can be used. Antigens can be prepared in accordance with methods that are known to those skilled in the art, such as methods using baculoviruses (such as that described in WO 98/46777). Hybridomas can be produced, for example, following methods of Milstein et al. (G. Kohler and C. Milstein, Methods Enzymol. 1981, 73: 3-46), and such. When the immunogenicity of an antigen is low, it can be linked to a macromolecule that has immunogenicity, such as albumin, and then used for immunization. Furthermore, by linking antigens with other molecules as necessary, they can be converted into soluble antigens. When transmembrane molecules such as receptors are used as antigens, portions of the extracellular regions of the receptors can be used as a fragment, or cells expressing transmembrane molecules on their cell surface may be used as immunogens.

Antibody-producing cells can be obtained by immunizing animals using suitable sensitizing antigens described above. Alternatively, antibody-producing cells can be prepared by in vitro immunization of lymphocytes that can produce antibodies. Various mammals can be used as the animals for immunization, and rodents, lagomorphas and primates are generally used. Specific examples of such animals include mice, rats, and hamsters for rodents, rabbits for lagomorphas, and monkeys including the cynomolgus monkey, rhesus monkey, hamadryas, and chimpanzees for primates.

Transgenic animals carrying human antibody gene repertoires are also known, and human antibodies can be obtained by using these animals (see WO96/34096; Mendez et al., Nat. Genet. 1997, 15: 146-56). Instead of using such transgenic animals, for example, desired human antibodies having binding activity against antigens can be obtained by in vitro sensitization of human lymphocytes with desired antigens or cells expressing the desired antigens, and then fusing the sensitized lymphocytes with human myeloma cells such as U266 (see Japanese Patent Application Kokoku Publication No. (JP-B) H1-59878 (examined, approved Japanese patent application published for opposition)). Furthermore, desired human antibodies can be obtained by immunizing transgenic animals carrying a complete repertoire of human antibody genes with desired antigens (see WO93/12227, WO92/03918, WO94/02602, WO96/34096, and WO96/33735).

Animal immunization is carried out by appropriately diluting and suspending a sensitizing antigen in Phosphate-Buffered Saline (PBS), physiological saline, or such, forming an emulsion by mixing an adjuvant if necessary, and intraperitoneally or subcutaneously injecting this into animals. After that, the sensitizing antigen mixed with Freund's incomplete adjuvant is preferably administered several times every four to 21 days. Antibody production can be confirmed by measuring the target antibody titer in animal sera using conventional methods.

Antibody-producing cells obtained from lymphocytes or animals immunized with a desired antigen can be fused with myeloma cells to generate hybridomas using conventional fusing agents (for example, polyethylene glycol) (Goding, Monoclonal Antibodies: Principles and Practice, Academic Press, 1986, 59-103). Then, as required, hybridoma cells can be cultured and grown, and the binding specificity, affinity, or activity of the antibody produced from these hybridomas can be measured using known analysis methods, such as immunoprecipitation, radioimmunoassay (RIA), and enzyme-linked immunosorbent assay (ELISA). Thereafter, hybridomas that produce antibodies of interest whose binding specificity, affinity, or activity has been determined can be subcloned by methods such as limiting dilution.

Next, genes encoding the antibodies of interest can be cloned from hybridomas or antibody-producing cells (sensitized lymphocytes, and such) using probes that may specifically bind to the antibodies (for example, oligonucleotides complementary to sequences encoding the antibody constant regions). Cloning from mRNAs using RT-PCR is also possible. Immunoglobulins are classified into five different classes, IgA, IgD, IgE, IgG, and IgM. These classes are further divided into several subclasses (isotypes) (for example, IgG-1, IgG-2, IgG-3, and IgG-4; IgA-1 and IgA-2; and such). H chains and L chains used in the present invention to produce antibodies are not particularly limited and may derive from antibodies belonging to any of these classes or subclasses; however, IgG is particularly preferred.

Herein, it is possible to modify H-chain-encoding genes and L-chain-encoding genes using genetic engineering techniques. Genetically modified antibodies, such as chimeric antibodies and humanized antibodies, that have been artificially modified for the purpose of decreasing heterologous antigenicity and such against humans, can be appropriately produced for antibodies such as mouse antibodies, rat antibodies, rabbit antibodies, hamster antibodies, sheep antibodies, and camel antibodies.

Chimeric antibodies are antibodies composed of a non-human mammal antibody H chain and L chain variable regions, such as those of a mouse antibody, and the H chain and L chain constant regions of a human antibody. They can be obtained by ligating the DNA encoding a variable region of a mouse antibody to the DNA encoding a constant region of a human antibody, incorporating them into an expression vector, and introducing the vector into a host for production of the antibody. A humanized antibody is also called a reshaped human antibody. This humanized antibody can be synthesized by PCR from a number of oligonucleotides produced so that they have overlapping portions at the ends of DNA sequences designed to link the complementarity determining regions (CDRs) of an antibody of a nonhuman mammal (such as a mouse). The obtained DNA can be ligated to a DNA encoding a human antibody constant region. The ligated DNA can be incorporated into an expression vector, and the vector can be introduced into a host to produce the antibody (see EP239400 and WO96/02576). Human antibody FRs that are ligated via the CDRs are selected when the CDRs form a favorable antigen-binding site. If necessary, amino acids in the framework region of an antibody variable region may be substituted such that the CDRs of the reshaped human antibody form an appropriate antigen-binding site (K. Sato et al., Cancer Res. 1993, 53: 851-856).

In addition to the humanization techniques described above, antibodies may be modified to improve their biological properties, for example, antigenic affinity. Such modifications can be carried out using methods such as site-directed mutagenesis (see for example, Kunkel (1985) Proc. Natl. Acad. Sci. USA 82: 488), PCR mutagenesis, and cassette mutagenesis. In general, mutant antibodies whose biological properties have been improved show amino acid sequence homology and/or similarity of 70% or higher, more preferably 80% or higher, and even more preferably 90% or higher (for example, 95% or higher, 97%, 98%, 99%, etc.), when compared to the amino acid sequence of the original antibody variable region. Herein, a sequence homology and/or similarity is defined as the ratio of amino acid residues that are homologous (same residue) or similar (amino acid residues classified into the same group based on the general properties of amino acid side chains) to the original antibody residues, after the sequence homology value has been maximized by sequence alignment and gap introduction as necessary. Generally, naturally-occurring amino acid residues are classified into groups based on the characteristics of their side chains:
(1) hydrophobic: alanine, isoleucine, norleucine, valine, methionine, and leucine;
(2) neutral hydrophilic: asparagine, glutamine, cysteine, threonine, and serine;
(3) acidic: aspartic acid, and glutamic acid;
(4) basic: arginine, histidine, and lysine;
(5) residues that affect the orientation of the chain: glycine, and proline; and
(6) aromatic: tyrosine, tryptophan, and phenylalanine.

Normally, an antigen binding site of an antibody is formed by the interactions of a total of six complementarity determining regions (hypervariable portions; CDRs) present in the variable regions of the H chain and L chain. It is known that even one of these variable regions has the ability to recognize and bind the antigen, although the affinity will be lower than that of the variable regions containing all the binding sites. Thus, with regard to the antibody genes of the present invention encoding H chains and L chains, the polypeptides encoded by these genes are only required to maintain the ability of binding to a desired antigen and to encode a fragment portion containing the respective antigen-binding sites of the H chain and L chain.

A more detailed explanation is provided below on the case of an IgG-type bispecific antibody having two types of heavy chain constant regions CH1 (CH1-A and CH1-B) and two types of light chain constant regions (CL-A and CL-B); however, the present invention can be similarly applied to other antibodies as well.

When one wishes to obtain a bispecific antibody that would recognize one epitope by the first CH1-A and the first CL-A, and another epitope by the second CH1-B and the second CL-B, theoretically there is the possibility that 10 types of antibody molecules may be produced when each of the four types of chains is expressed for producing that antibody.

In this case, desired antibody molecules can be preferentially acquired if, for example, the association is regulated so that association of CH1-A and CL-B and/or between CH1-B and CL-A is inhibited.

An example is modifying amino acid residues forming an interface between CH1-A and CL-B into positively charged amino acid residues and modifying amino acid residues forming an interface between CH1-B and CL-A into negatively charged amino acid residues. As a result of these modifications, unintended association between CH1-A and CL-B is inhibited since the amino acid residues forming the interface are both positively charged, and association between CH1-B and CL-A is also inhibited since the amino acid residues forming the interface are both negatively charged. Thus, the unintended association between CH1-A and CL-B and association between CH1-B and CL-A are inhibited because the amino acid residues forming the interfaces mutually have the same charge. As a result, antibodies having the intended association between CH1-A and CL-A, and the intended association between CH1-B and CL-B can be acquired efficiently. Moreover, the intended association between CH1-A and CL-A is promoted since the amino acid residues forming the interface have different types of charges from each other; and the intended association between CH1-B and CL-B is also promoted since the amino acid residues forming the interface have different types of charges from each other. Consequently, antibodies with intended association can be efficiently obtained.

Another example is modifying the amino acid residues forming the interface between CH1-A and CL-B into positively charged amino acid residues, when the amino acid residues forming the interface between CL-A and CH1-B are mutually uncharged or nonpolar amino acids. As a result of this modification, the unintended association between CH1-A and CL-B is inhibited because the amino acid residues forming the interface are both positively charged. On the other hand, since the amino acid residues forming the interfaces are amino acids that do not mutually repel electrically, the intended association between CH1-A and CL-A, and the intended association between CH1-B and CL-B will occur more easily than in the case where the amino acids repel electrically. Consequently, antibodies having the intended association between CH1-A and CL-A, and the intended association between CH1-B and CL-B can be efficiently obtained. Meanwhile, in this example, in the case that the amino acid residues forming the interface between CL-A and CH1-B are not mutually uncharged or nonpolar amino acids, they may be modified so as to become mutually uncharged or nonpolar amino acids.

In another example, when amino acid residues forming the interface between CL-B and CH1-B are mutually uncharged or nonpolar amino acids, one of the amino acid residues forming the interface between CH1-A and CL-A is modified into a positively charged amino acid residue, and the other is modified into a negatively charged amino acid residue. As a result of this modification, while the intended association between CH1-A and CL-A is promoted because the amino acid residues forming the interface are a combination of positive charge and negative charge, the intended association between CH1-B and CL-B is not inhibited because the amino acid residues forming the interface are amino acids that do not mutually repel electrically. As a result, one can efficiently obtain an antibody having intended association between CH1-A and CL-A, and intended association between CH1-B and CL-B. Meanwhile, in this example, when the amino acid residues forming the interface between CL-B and CH1-B are not mutually uncharged or nonpolar amino acids, they may be modified so as to become mutually uncharged or nonpolar amino acids.

Moreover, in another example, when the amino acid residues forming the interface between CL-B and CH1-B are uncharged or nonpolar amino acids in CH1-B, one of the amino acid residues forming the interface between CH 1-A and CL-A is modified into a positively charged amino acid residue while the other is modified into a negatively charged amino acid residue; and amino acid residues forming the interface between CL-B and CH1-B in CL-B are modified so as to have the same charge as the modification made to CH1-A. As a result of this modification, while the intended association between CH1-A and CL-A is promoted because the amino acid residues forming the interface are a combination of positive charge and negative charge, the intended association between CH1-B and CL-B is not inhibited because the amino acid residues forming the interface are amino acids that do not mutually repel electrically. As a result, one can efficiently obtain an antibody having intended association between CH1-A and CL-A, and intended association between CH1-B and CL-B. Meanwhile, in this example, when the amino acid residues forming the interface between CL-B and CH1-B are not uncharged or nonpolar amino acids in CH1-B, they may be modified so as to become uncharged or nonpolar amino acids.

In addition, use of the association regulation of the present invention makes it possible to suppress association between CH1s (CH1-A and CH1-B), or association between CLs (CL-A and CL-B).

Those skilled in the art would be able to suitably determine the types of amino acid residues that come close during association at the CH1 and CL interface in a desired polypeptide for which regulation of association by the present invention is desired.

Further, those skilled in the art can also suitably acquire sequences that can be used as CH1 or CL of an antibody in an organism such as a human, monkey, mouse, rabbit, and the like by using a public database and such. More specifically, the amino acid sequence information of CH1 or CL can be acquired by means described in the Examples described below.

For example, with respect to the bispecific antibodies described in the Examples below, specific examples of amino acid residues that come close (that face or are in contact) at the interface of CH1 and CL upon association include the combinations shown below:

lysine (K) at position 147 as indicated by EU numbering in CH1 (for example, position 147 in the amino acid sequence of SEQ ID NO: 1) and the facing (contacting) threonine (T) at position 180 as indicated by EU numbering in CL;

lysine (K) at position 147 as indicated by EU numbering in CH1 and the facing (contacting) serine (S) at position 131 as indicated by EU numbering in CL;

glutamine (Q) at position 175 as indicated by EU numbering in CH1 and the facing (contacting) glutamine (Q) at position 160 as indicated by EU numbering in CL; and, lysine (K) at position 213 as indicated by EU numbering in CH1 and the facing (contacting) glutamic acid (E) at position 123 as indicated by EU numbering in CL.

The numbers described in EU numbering in the present invention are indicated in accordance with EU numbering (Sequences of proteins of immunological interest, NIH Publication No. 91-3242). In the present invention, the phrases "an amino acid residue at position X as indicated by EU numbering" and "an amino acid at position X as indicated by EU numbering" (where X is an arbitrary number) can also be read as "an amino acid residue that corresponds to position X as indicated by EU numbering" and "an amino acid that corresponds to position X as indicated by EU numbering".

As indicated in the Examples described below, desired antibodies can be preferentially acquired by modifying these amino acid residues and carrying out the methods of the present invention.

Accordingly, the present invention provides an antibody in which association of the heavy chain and light chain is regulated, wherein one or two or more sets of amino acid residues selected from the group consisting of the sets of amino acid residues shown in (a) to (c) below in the heavy chain and light chain of the antibody are amino acid residues that mutually repel electrically:

(a) the amino acid residue contained in the heavy chain constant region (CH1) at position 147 as indicated by EU numbering, and the amino acid residue contained in the light chain constant region (CL) at position 180 as indicated by EU numbering;

(b) the amino acid residue contained in CH1 at position 147 as indicated by EU numbering, and the amino acid residue contained in CL at position 131 as indicated by EU numbering; and (c) the amino acid residue contained in CH1 at position 175 as indicated by EU numbering, and the amino acid residue contained in CL at position 160 as indicated by EU numbering.

As another embodiment, the present invention further provides an antibody in which the amino acid residues in the set of the amino acid residues of (d) below are amino acid residues that mutually repel electrically:

(d) the amino acid residue contained in CH1 at position 213 as indicated by EU numbering, and the amino acid residue contained in CL at position 123 as indicated by EU numbering.

In the aforementioned antibody, the "amino acid residues that mutually repel electrically" or "amino acid residues having the same charge" are preferably selected from amino acid residues contained in, for example, either of the set of (X) or (Y) below:

(X) glutamic acid (E) or aspartic acid (D); or (Y) lysine (K), arginine (R), or histidine (H).

In the aforementioned antibody, specific examples of amino acid residues that mutually repel electrically include the amino acid residues below:

the amino acid residue contained in CH1 at position 175 as indicated by EU numbering is lysine (K), and the amino acid residues contained in CL at position 180, position 131, and position 160 as indicated by EU numbering are all glutamic acid (E); and, the amino acid residues contained in CH1 at position 147 and position 175 as indicated by EU numbering are glutamic acid (E), and the amino acid residues contained in CL at position 180, position 131, and position 160 as indicated by EU numbering are all lysine (K).

In the aforementioned antibody, examples of amino acid residues that do not electrically repel further include one in which the amino acid residue contained in CH1 at position 213 as indicated by EU numbering is glutamic acid (E), and the amino acid residue contained in CL at position 123 as indicated by EU numbering is lysine (K).

Moreover, methods for producing an aforementioned antibody and methods of the present invention for regulating association through modification of the amino acid residues in the sets of amino acid residues of (a) to (d) mentioned above into amino acid residues that mutually repel electrically are also preferred embodiments of the present invention.

Further, the present invention provides an antibody in which association of the heavy chain and light chain is regulated, wherein one or two or more sets of amino acid residues selected from the group consisting of the sets of amino acid residues shown in (a) to (c) below in the associating heavy chain and light chain of the antibody are amino acid residues that do not mutually repel electrically:

(a) the amino acid residue contained in CH1 at position 147 as indicated by EU numbering, and the amino acid residue contained in CL at position 180 as indicated by EU numbering;

(b) the amino acid residue contained in CH1 at position 147 as indicated by EU numbering, and the amino acid residue contained in CL at position 131 as indicated by EU numbering; and (c) the amino acid residue contained in CH1 at position 175 as indicated by EU numbering, and the amino acid residue contained in CL at position 160 as indicated by EU numbering.

As another embodiment, the present invention further provides an antibody in which the amino acid residues in the set of amino acid residues shown in (d) below are amino acid residues that do not mutually repel electrically:
(d) the amino acid residue contained in CH1 at position 213 as indicated by EU numbering, and the amino acid residue contained in CL at position 123 as indicated by EU numbering.

As indicated in the Examples described below and FIG. 1, each of the amino acid residues of the aforementioned combinations mutually approaches upon association. Those skilled in the art would be able to find sites corresponding to the amino acid residues described in (a) to (d) mentioned above for the desired CH1 or CL by homology modeling and such using commercially available software, and to suitably modify the amino acid residues at those sites.

In the aforementioned antibody, the "amino acid residues that do not mutually repel electrically" are preferably selected from, for example, each of the two sets selected from the group consisting of (X) to (Z) shown below, and where the two sets are selected from among the combinations of (X) and (Y), (X) and (Z), (Y) and (Z), and (Z) and (Z):
(X) glutamic acid (E) or aspartic acid (D);
(Y) lysine (K), arginine (R) or histidine (H);
(Z) alanine (A), asparagine (N), cysteine (C), glutamine (Q), glycine (G), isoleucine (I), leucine (L), methionine (M), phenylalanine (F), proline (P), serine (S), threonine (T), tryptophan (W), tyrosine (Y) or valine (V).

An example involves selecting (X) and (Y) from the group consisting of (X) to (Z), selecting glutamic acid from (X) and selecting lysine (K) from (Y); and modifying the amino acid residue contained in CH1 at position 147 as indicated by EU numbering to glutamic acid (E), and modifying the amino acid residue contained in CL at position 180 as indicated by EU numbering to lysine (K). In this case, there is no need to modify the amino acid residue contained in CH1 at position 147 as indicated by EU numbering if the amino acid residue is glutamic acid (E) from before the modification.

In the aforementioned antibody, specific examples of amino acid residues that do not mutually repel electrically include the amino acid residues shown below:
the amino acid residue contained in CH1 at position 175 as indicated by EU numbering is lysine (K), and the amino acid residues contained in CL at position 180, position 131, and position 160 as indicated by EU numbering are all glutamic acid (E); and
the amino acid residues contained in CH1 at position 147 and position 175 as indicated by EU numbering are glutamic acid (E), and the amino acid residues contained in CL at position 180, position 131, and position 160 as indicated by EU numbering are all lysine (K).

In the aforementioned antibody, examples of amino acid residues that do not electrically repel further include one in which the amino acid residue contained in CH1 at position 213 as indicated by EU numbering is glutamic acid (E), and the amino acid residue contained in CL at position 123 as indicated by EU numbering is lysine (K).

Moreover, methods for producing an aforementioned antibody, and methods of the present invention for regulating association through modification of the amino acid residues in the sets of amino acid residues in (a) to (d) mentioned above into amino acid residues that do not mutually repel electrically are also preferred embodiments of the present invention.

A technique for introducing electrical repulsion into the interface of the second constant region of the heavy chain (CH2) or the third constant region of the heavy chain (CH3) to suppress undesired association between heavy chains, a technique for introducing electrical repulsion into the interface of the heavy chain variable region and light chain variable region to suppress unintended association between the heavy chain and light chain, or a technique for modifying amino acid residues forming a hydrophobic core present at the interface of the heavy chain variable region and light chain variable region into polar amino acids having an electrical charge to suppress unintended association between the heavy chain and light chain can be further applied to the antibody of the present invention (see WO 2006/106905).

In the technique that suppresses unintended association between heavy chains by introducing electrical repulsion at the interface of CH2 or CH3, examples of amino acid residues that are in contact at the interface of other constant regions of the heavy chain include regions corresponding to position 377 (position 356) and position 470 (position 439), position 378 (position 357) and position 393 (position 370), and position 427 (position 399) and position 440 (position 409) in the CH3 region. For the numbering of the antibody constant regions, one may refer to the publication by Kabat et al. (Kabat, E. A., et al., 1991, Sequences of Proteins of Immunological Interest, NIH); and for the numbering of the heavy chain constant regions, the EU numbering are shown inside the parentheses.

The technique of modifying the amino acid residue at position 435 as indicated by EU numbering, which is a site related to binding between IgG and Protein A, to an amino acid having a different binding strength toward Protein A, such as Arg, may also be used on the antibody of the present invention in combination with the aforementioned techniques. By using this technique, the interaction between the H chain and Protein A can be changed, and only heterodimeric antibodies can be efficiently purified using a Protein A column. This technique can also be used independently without combining with the aforementioned techniques.

More specifically, for example, in an antibody containing two types of heavy chain CH3 regions, one to three sets of amino acid residues in the first heavy chain CH3 region, which are selected from the sets of amino acid residues of (1) to (3) below, may be made to mutually repel electrically:
(1) the amino acid residues contained in the heavy chain CH3 region at position 356 and position 439 as indicated by EU numbering;
(2) the amino acid residues contained in the heavy chain CH3 region at position 357 and position 370 as indicated by EU numbering; and
(3) the amino acid residues contained in the heavy chain CH3 region at position 399 and position 409 as indicated by EU numbering.

Moreover, the antibody can be an antibody having a set of amino acid residues in the second heavy chain CH3 region distinct from the aforementioned first heavy chain CH3 region, wherein the set of amino acid residues is selected from the sets of amino acid residues shown in (1) to (3) above, and wherein the one to three sets of amino acid residues that correspond to the sets of amino acid residues shown in (1) to (3) above, which mutually repel electrically in the first heavy chain CH3 region, do not electrically repel from the corresponding amino acid residues in the first heavy chain CH3 region.

The amino acid residues described in (1) to (3) above approach each other upon association. Those skilled in the art would be able to find sites corresponding to the amino acid residues described in (1) to (3) mentioned above for a desired heavy chain CH3 region or heavy chain constant region by homology modeling and such using commercially available software, and to suitably modify the amino acid residues at those sites.

In the aforementioned antibody, "electrically repelling" or "having a same charge" means that, for example, any two or more amino acid residues have amino acid residues that are contained in either one group of (X) and (Y) mentioned above. On the other hand, "not electrically repelling" means that, for example, the antibody has amino acid residues that are selected from each of two sets selected from the group consisting of (X) and (Y) mentioned above and (Z) below, where the two sets are selected from among the combinations of (X) and (Y), (X) and (Z), (Y) and (Z), and (Z) and (Z):

(Z) alanine (A), asparagine (N), cysteine (C), glutamine (Q), glycine (G), isoleucine (I), leucine (L), methionine (M), phenylalanine (F), proline (P), serine (S), threonine (T), tryptophan (W), tyrosine (Y) or valine (V).

In a preferred embodiment of the aforementioned antibody, the first heavy chain CH3 region and the second heavy chain CH3 region may be cross-linked by disulfide bonds.

In the present invention, an amino acid residue subjected to "modification" is not limited to an amino acid residue of the antibody variable region or antibody constant region mentioned above. Those skilled in the art would be able to find amino acid residues that form an interface in a polypeptide variant or heteromeric multimer by homology modeling and the like using commercially available software, and to modify amino acid residues at those sites so as to regulate association. Homology modeling is a technique for predicting the three-dimensional structure of a protein using commercially available software. When constructing the structure of a protein with unknown three-dimensional structure, one first searches for a protein that has been determined to have a highly homologous three-dimensional structure to the protein. Next, using this three-dimensional structure as a template, one constructs the structure of the protein with unknown structure, and the structure is further optimized by molecular dynamics methods and the like to predict the three-dimensional structure of the unknown protein.

In the technique for introducing electrical repulsion into the interface of the heavy chain variable region and light chain variable region to suppress undesired association of the heavy chain and light chain, examples of amino acid residues that are in contact at the interface of the heavy chain variable region (VH) and light chain variable region (VL) include glutamine (Q) at position 39 as indicated by Kabat numbering in the heavy chain variable region (FR2 region) and the facing (contacting) glutamine (Q) at position 38 as indicated by Kabat numbering in the light chain variable region (FR2 region). Moreover, a preferable example is leucine (L) at position 45 according to the Kabat numbering in the heavy chain variable region (FR2) and the facing proline (P) at position 44 according to the Kabat numbering in the light chain variable region (FR2). The publication by Kabat, et al. (Kabat, E. A., et al., 1991, Sequence of Proteins of Immunological Interest, NIH) was referred to for the numbering of these sites.

Since these amino acid residues are known to be highly conserved in humans and mice (J. Mol. Recognit. 2003; 16: 113-120), association of antibody variable regions can be regulated for VH-VL association of antibodies other than those indicated in the Examples by modifying amino acid residues corresponding to the above-mentioned amino acid residues.

A specific example is an antibody in which two or more amino acid residues forming the interface of the heavy chain variable region and light chain variable region are amino acid residues that mutually repel electrically.

More specifically, examples include an antibody with one set or two sets of amino acid residues selected from the group consisting of the sets of amino acid residues shown in (a) or (b) below:

(a) the amino acid residue contained in the heavy chain variable region (1) at position 39 as indicated by Kabat numbering and the amino acid residue contained in the light chain (2) at position 38 as indicated by Kabat numbering; or (b) the amino acid residue contained in the heavy chain variable region (3) at position 45 as indicated by Kabat numbering and the amino acid residue contained in the light chain variable region (4) at position 44 as indicated by Kabat numbering.

Each of the amino acid residues described in the aforementioned (a) or (b) approaches each other upon association. Those skilled in the art would be able to find sites that correspond to the amino acid residues described in the aforementioned (a) or (b) in a desired heavy chain variable region or light chain variable region by homology modeling and the like using commercially available software, and to suitably modify the amino acid residues at those sites.

In the aforementioned antibody, "amino acid residues that mutually repel electrically" are preferably selected from amino acid residues contained in, for example, either of the sets (X) and (Y) below:

(X) glutamic acid (E) or aspartic acid (D); or
(Y) lysine (K), arginine (R), or histidine (H).

In addition, another embodiment of the antibody of the present invention is, for example, an antibody in which two or more amino acid residues that form the interface of the heavy chain variable region and light chain variable region are amino acid residues that do not electrically repel each other. Specifically, an example of such an antibody is one having one set or two sets of amino acid residues selected from the group consisting of the sets of amino acid residues shown in the aforementioned (a) and (b).

The respective amino acid residues described in the aforementioned (a) or (b) are close to each other upon association. Those skilled in the art would be able to find sites that correspond to the amino acid residues described in the aforementioned (a) or (b) for a desired heavy chain variable region or light chain variable region by homology modeling and the like using commercially available software, and to suitably subject amino acid residues at those sites to modification.

In the aforementioned antibody, "amino acid residues that do not mutually repel electrically" refers to, for example, amino acid residues selected from each of two sets selected from the group consisting of (X) to (Z) mentioned above, and where the two sets are selected from among the combinations of (X) and (Y), (X) and (Z), (Y) and (Z), and (Z) and (Z).

Generally, the amino acid residues described in the aforementioned (a) or (b) in humans and mice are:
(1) glutamine (Q),
(2) glutamine (Q),
(3) leucine (L), and
(4) proline (P).

Thus, in a preferred embodiment of the present invention, these amino acid residues are subjected to modification (such as substitution with amino acids having an electrical charge). Furthermore, the types of amino acid residues of the aforementioned (a) or (b) are not necessarily limited to the aforementioned amino acid residues, but may also be other amino acids equivalent to these amino acids. For example, the amino acid at position 38 as indicated by Kabat numbering in the light chain variable region may be, for example, histidine (H) in the case of humans.

In the technique for modifying amino acid residues forming a hydrophobic core present at the interface of the heavy chain variable region and light chain variable region into polar amino acids having an electrical charge to suppress unintended association of the heavy chain and light chain, preferable examples of amino acid residues which are able to form a hydrophobic core at the interface of the heavy chain variable region (VH) and light chain variable region (VL) include leucine (L) at position 45 as indicated by Kabat numbering in the heavy chain variable region (FR2) and the facing proline (P) at position 44 as indicated by Kabat numbering in light chain variable region (FR2). For the numbering of these sites, Kabat, et al. (Kabat, E. A., et al., 1991, Sequences of Proteins of Immunological Interest, NIH) was used as a reference.

In general, the term "hydrophobic core" refers to a part that is formed by an assembly of hydrophobic amino acid side chains at the interior of associated polypeptides. Examples of hydrophobic amino acids include alanine, isoleucine, leucine, methionine, phenylalanine, proline, tryptophan, and valine. Furthermore, amino acid residues other than hydrophobic amino acids (for example tyrosine) may be involved in the formation of a hydrophobic core. This hydrophobic core together with a hydrophilic surface, in which hydrophilic amino acid side chains are exposed to the exterior, becomes a driving force for promoting association of water-soluble polypeptides. When hydrophobic amino acids of two different domains are present on a molecular surface and are exposed to water molecules, the entropy will increase and the free energy will increase. Accordingly, the two domains will associate with each other to decrease the free energy and become stable, and hydrophobic amino acids at the interface will be buried into the interior of the molecule to form a hydrophobic core.

It is thought that when polypeptide association occurs, formation of a hydrophobic core is inhibited by modifying hydrophobic amino acids forming the hydrophobic core to polar amino acids having an electrical charge; and consequently, polypeptide association is thought to be inhibited.

Those skilled in the art would be able to recognize the presence or absence of a hydrophobic core, the formation site (region), and the like by analyzing amino acid sequences for a desired polypeptide. Namely, the antibody of the present invention is an antibody characterized in that amino acid residues capable of forming a hydrophobic core at an interface are modified to amino acid residues having an electrical charge. More specifically, examples include an antibody in which the amino acid residues shown in either (1) or (2) below are amino acid residues having an electrical charge. Side chains of the amino acid residues shown in (1) and (2) below are adjacent to each other, and can form a hydrophobic core:
(1) the amino acid residue contained in the heavy chain variable region at position 45 as indicated by Kabat numbering; and
(2) the amino acid residue contained in the light chain variable region at position 44 as indicated by Kabat numbering.

Preferable examples of amino acid residues having an electrical charge in the aforementioned antibody include glutamic acid (E), aspartic acid (D), lysine (K), arginine (R) and histidine (H). More preferable examples include glutamic acid (E) and lysine (K).

Generally, the amino acid residues described in the aforementioned (1) and (2) in humans and mice are respectively:
(1) leucine (L), and
(2) proline (P).

Thus, in a preferred embodiment of the present invention, these amino acid residues are subjected to modification (such as substitution with amino acids having an electrical charge). Furthermore, the types of the aforementioned amino acid residues of (1) and (2) are not necessarily limited to the aforementioned amino acid residues, but may also be other amino acids equivalent to these amino acid residues.

Other known techniques can be applied to the antibodies of the present invention. For example, in order to promote association of the first VH (VH1) and the first VL (VL1) and/or the second VH (VH2) and the second VL (VL2), an amino acid side chain present in the variable region of one of the H chains can be substituted with a larger side chain (knob), and an amino acid side chain present in the opposing variable region of the other H chain can be substituted with a smaller side chain (hole), so that the knob may be arranged in the hole, and association of VH1 and VL1 and/or VH2 and VL2 is promoted; and consequently, association of VH1 and VL2 and/or VH2 and VL1 can be further suppressed (WO 1996/027011; Ridgway, J. B., et al., Protein Engineering (1996) 9, 617-621; Merchant, A. M., et al., Nature Biotechnology (1998) 16, 677-681).

For example, in the case of human IgG1, in order to make an amino acid side chain in the CH3 region of one H chain a larger side chain (knob), the modifications of Y349C and T366W are made, and in order to make an amino acid side chain in the CH3 region of the other H chain a smaller side chain, the modifications of D356C, T336S, L368A and Y407V are made.

Still other known techniques can be applied to the antibodies of the present invention. A target antibody can be efficiently prepared by complementary association of CH3 using strand-exchange engineered domain CH3, in which a portion of CH3 of one H chain of an antibody is changed to a sequence derived from IgA corresponding to that portion, and a complementary portion of CH3 of the other H chain is introduced with a sequence derived from IgA corresponding to that portion (Protein Engineering Design & Selection, 23: 195-202, 2010).

Still other known techniques can be applied to the antibodies of the present invention. When producing bispecific antibodies, a target bispecific antibody can be prepared by, for example, imparting a difference in isoelectric point by making different amino acid modifications to each of the variable regions of the two types of H chains, and utilizing that difference in isoelectric point for purification by ion exchange chromatography (WO 2007/114325).

The modifications of the present invention can be used on antibodies such as the one below, for example, an antibody having a structure in which, to promote association of a first VH (VH1) and a first VL (VL1) and/or a second VH (VH2) and a second VL (VL2), VH1 is linked to an Fc region through a first CH1 and VL1 is linked to a first CL, and VH2 is linked to another Fc region through a second CL and VL2 is linked to a second CH1 (WO 09/80254).

A plurality, for example, two or more of the aforementioned known techniques can be used in combination for the antibody of the present invention. Furthermore, the antibody of the present invention may be prepared based on an antibody to which modifications of the aforementioned known techniques have been made.

The below-mentioned methods of the present invention for regulating association allow, for example, for the efficient production of antibodies or polypeptides that are active.

Examples of such activities include binding activity, neutralizing activity, cytotoxic activity, agonist activity, antagonist activity, and enzyme activity and such. Agonist activity is an activity that induces some kind of changes in physiological activity through binding of an antibody to an antigen, such as a receptor, which causes signal transduction or such in cells. Examples of the physiological activity include growth activity, survival activity, differentiation activity, transcriptional activity, membrane transport activity, binding activity, proteolytic activity, phosphorylation/dephosphorylation activity, redox activity, transfer activity, nucleolytic activity, dehydration activity, cell death-inducing activity, and apoptosis-inducing activity and such, but are not limited thereto.

Antibodies or polypeptides that recognize the desired antigens or bind to the desired receptors can be produced efficiently by the methods of the present invention.

The antigens of the present invention are not particularly limited, and any type of antigen can be used. Examples of antigens include receptors or their fragments, cancer antigens, MHC antigens, and differentiation antigens and the like, but are not particularly limited thereto.

Examples of the receptors of the present invention include receptors belonging to the hematopoietic factor receptor family, cytokine receptor family, tyrosine kinase-type receptor family, serine/threonine kinase-type receptor family, TNF receptor family, G protein-coupled receptor family, GPI-anchored receptor family, tyrosine phosphatase-type receptor family, adhesion factor family, hormone receptor family, and such. Reports on the receptors belonging to these receptor families and their characteristics can be found in various sources of documents, for example, in Cooke B A., King R J B., van der Molen H J. ed. New Comprehensive Biochemistry Vol. 18B "Hormones and their Actions Part II" pp. 1-46 (1988) Elsevier Science Publishers BV., New York, USA; Patthy L. (1990) Cell, 61: 13-14; Ullrich A., et al. (1990) Cell, 61: 203-212; Massagul J. (1992) Cell, 69: 1067-1070; Miyajima A., et al. (1992) Annu Rev. Immunol., 10: 295-331; Taga T. and Kishimoto T. (1992) FASEB J., 7: 3387-3396; Fantl W I., et al. (1993) Annu Rev. Biochem., 62: 453-481; Smith C A., et al. (1994) Cell, 76: 959-962; Flower D R. (1999) Biochim. Biophys. Acta, 1422: 207-234; Miyasaka M. ed. Cell Technology, Handbook Series "Handbook for adhesion factors" (1994) Shujunsha, Tokyo, Japan; and such. Examples of specific receptors belonging to the above-mentioned receptor families include human or mouse erythropoietin (EPO) receptor, human or mouse granulocyte-colony stimulating factor (G-CSF) receptor, human or mouse thrombopoietin (TPO) receptor, human or mouse insulin receptor, human or mouse Flt-3 ligand receptor, human or mouse platelet-derived growth factor (PDGF) receptor, human or mouse interferon (IFN)-α or -β receptor, human or mouse leptin receptor, human or mouse growth hormone (GH) receptor, human or mouse interleukin (IL)-10 receptor, human or mouse insulin-like growth factor (IGF)-I receptor, human or mouse leukemia inhibitory factor (LIF) receptor, and human or mouse ciliary neurotrophic factor (CNTF) receptor (hEPOR: Simon, S. et al. (1990) Blood 76, 31-35; mEPOR: D'Andrea, A D. et al. (1989) Cell 57, 277-285; hG-CSFR: Fukunaga, R. et al. (1990) Proc. Natl. Acad. Sci. USA. 87, 8702-8706; mG-CSFR: Fukunaga, R. et al. (1990) Cell 61, 341-350; hTPOR: Vigon, I. et al. (1992) 89, 5640-5644; mTPOR: Skoda, R C. et al. (1993) 12, 2645-2653; hInsR: Ullrich, A. et al. (1985) Nature 313, 756-761; hFlt-3: Small, D. et al. (1994) Proc. Natl. Acad. Sci. USA. 91, 459-463; hPDGFR: Gronwald, R G K. et al. (1988) Proc. Natl. Acad. Sci. USA. 85, 3435-3439; hIFN α/β R: Uze, G. et al. (1990) Cell 60, 225-234; and Novick, D. et al. (1994) Cell 77, 391-400).

Cancer antigens are antigens that are expressed following malignant transformation of a cell, and are also referred to as tumor specific antigens. In addition, abnormal sugar chains which appear on a cell surface or on a protein molecule when the cell has become cancerous are also cancer antigens, and they are also referred to as cancer sugar chain antigens. Examples of cancer antigens include EpCAM, which is expressed in multiple cancers including lung cancer (Proc. Natl. Acad. Sci. USA (1989) 86 (1), 27-31) (the polynucleotide sequence thereof is indicated as RefSeq Accession No. NM_002354.2 (SEQ ID NO: 78) and the polypeptide sequence thereof is indicated as RefSeq Accession No. NP_002345.2 (SEQ ID NO: 79)), CA19-9, CA15-3, sialyl SSEA-1 (SLX), etc.

MHC antigens can be classified broadly into MHC class I antigens and MHC class II antigens: MHC class I antigens include HLA-A, -B, -C, -E, -F, -G, and -H; and MHC class II antigens include HLA-DR, -DQ, and -DP.

Differentiation antigens include CD1, CD2, CD3, CD4, CD5, CD6, CD7, CD8, CD10, CD11a, CD11b, CD11c, CD13, CD14, CD15s, CD16, CD18, CD19, CD20, CD21, CD23, CD25, CD28, CD29, CD30, CD32, CD33, CD34, CD35, CD38, CD40, CD41a, CD41b, CD42a, CD42b, CD43, CD44, CD45, CD45RO, CD48, CD49a, CD49b, CD49c, CD49d, CD49e, CD49f, CD51, CD54, CD55, CD56, CD57, CD58, CD61, CD62E, CD62L, CD62P, CD64, CD69, CD71, CD73, CD95, CD102, CD106, CD122, CD126, and CDw130.

The antibodies of the present invention may be a bispecific antibody; and in that case, two antigens (or epitopes) recognized by that antibody can be arbitrarily selected from the aforementioned receptors or fragments thereof, cancer antigens, MHC antigens, differentiation antigens and the like. For example, two antigens may be selected from receptors or fragments thereof, two may be selected from cancer antigens, two may be selected from MHC antigens, or two may be selected from differentiation antigens. In addition, one antigen each may be selected from two antigens arbitrarily selected from, for example, receptors or fragments thereof, cancer antigens, MHC antigens, and differentiation antigens.

In addition, the present invention provides a method for producing an antibody in which association of the heavy chain and light chain is regulated.

A preferred embodiment of the production method of the present invention is a method for producing an antibody in which association of the heavy chain and light chain is regulated, comprising:

(1) modifying nucleic acids encoding CH1 and CL so that one set or two or more sets of amino acid residues selected from the group consisting of the sets of amino acid residues shown in (a) to (c) below become amino acid residues that electrically repel each other:

(a) the amino acid residue contained in CH1 at position 147 as indicated by EU numbering, and the amino acid residue contained in CL at position 180 as indicated by EU numbering;
(b) the amino acid residue contained in CH1 at position 147 as indicated by EU numbering, and the amino acid residue contained in CL at position 131 as indicated by EU numbering; and
(c) the amino acid residue contained in CH1 at position 175 as indicated by EU numbering, and amino acid residue contained in CL at position 160 as indicated by EU numbering,
(2) introducing the modified nucleic acids into host cells and culturing so that the host cells express the nucleic acids, and
(3) collecting an antibody from a cell culture of the host cells.

Another embodiment of the production method of the present invention includes a method for producing an antibody, wherein step (1) of the aforementioned production method further comprises modifying the nucleic acids so that the amino acid residues of the set of amino acid residues shown in (d) below become amino acid residues that electrically repel each other:
(d) the amino acid residue contained in CH1 at position 213 as indicated by EU numbering, and the amino acid residue contained in CL at position 123 as indicated by EU numbering.

In addition, the present invention relates to a production method comprising, in the aforementioned step (1), modifying the nucleic acids so that the amino acid residues that electrically repel each other are selected from among the amino acid residues contained in either of the groups of the aforementioned (X) and (Y).

Moreover, the present invention relates to a production method comprising in the aforementioned step (1), modifying the nucleic acids so that two or more amino acid residues that form the interface of the heavy chain variable region and light chain variable region are amino acid residues that electrically repel each other. Preferably, the amino acid residues that electrically repel each other are any set of amino acid residues selected from the group consisting of, for example, the sets of amino acid residues shown in (a) and (b) below:
(a) the amino acid residue contained in the heavy chain variable region at position 39 as indicated by Kabat numbering, and the amino acid residue contained in the light chain variable region at position 38 as indicated by Kabat numbering; or
(b) the amino acid residue contained in the heavy chain variable region at position 45 as indicated by Kabat numbering, and the amino acid residue contained in the light chain variable region at position 44 as indicated by Kabat numbering.

The aforementioned amino acid residues which electrically repel each other are preferably selected from the amino acid residues contained in either set of the aforementioned (X) and (Y).

Another preferred embodiment of the production method of the present invention includes a method for producing an antibody in which association of the heavy chain and light chain is regulated, comprising:
(1) modifying nucleic acids encoding CH1 and CL so that one set or two or more sets of amino acid residues selected from the group consisting of the sets of amino acid residues shown in (a) to (c) below become amino acid residues that do not electrically repel each other:

(a) the amino acid residue contained in CH1 at position 147 as indicated by EU numbering, and the amino acid residue contained in CL at position 180 as indicated by EU numbering;
(b) the amino acid residue contained in CH1 at position 147 as indicated by EU numbering, and the amino acid residue contained in CL at position 131 as indicated by EU numbering; and
(c) the amino acid residue contained in CH1 at position 175 as indicated by EU numbering, and the amino acid residue contained in CL at position 160 as indicated by EU numbering,
(2) introducing the modified nucleic acids into host cells and culturing so that the host cells express the nucleic acids, and
(3) collecting an antibody from a culture of the host cells.

Another embodiment of the production method of the present invention includes a production method further comprising in step (1) of the aforementioned production method, modifying the nucleic acids so that the amino acid residues of the set of amino acid residues shown in (d) below become amino acid residues that do not electrically repel each other:
(d) the amino acid residue contained in CH1 at position 213 as indicated by EU numbering, and the amino acid residue contained in CL at position 123 as indicated by EU numbering.

In addition, the present invention relates to a production method comprising, in the aforementioned step (1), modifying nucleic acids so that the amino acid residues that do not electrically repel each other are amino acid residues selected from each of two sets selected from the group consisting of the aforementioned (X) to (Z), and where the two sets are selected from among the combinations of (X) and (Y), (X) and (Z), (Y) and (Z), and (Z) and (Z).

In addition, specific examples of the amino acid residues that do not electrically repel each other in the aforementioned step (1) of the present invention include the following amino acid residues:
the amino acid residue contained in CH1 at position 175 as indicated by EU numbering which is lysine (K); and the amino acid residues contained in CL at position 180, position 131, and position 160 as indicated by EU numbering which are all glutamic acid (E); and
the amino acid residues contained in CH1 at position 147 and position 175 as indicated by EU numbering which are glutamic acid (E), and the amino acid residues contained in CL at position 180, position 131, and position 160 as indicated by EU numbering which are all lysine (K).

Moreover, in another example, the amino acid residue contained in CH1 at position 213 as indicated by EU numbering is glutamic acid (E), and the amino acid residue contained in CL at position 123 as indicated by EU numbering is lysine (K).

Moreover, the present invention relates to a production method, comprising in the aforementioned step (1), modifying the nucleic acids so that two or more amino acid residues that form the interface of the heavy chain variable region and light chain variable region are amino acid residues that do not electrically repel each other. Preferably, the amino acid residues that do not electrically repel each other are, for example, amino acid residues of any set selected from the group consisting of the sets of amino acid residues indicated in (a) and (b) below:
(a) the amino acid residue contained in the heavy chain variable region at position 39 as indicated by Kabat numbering, and the amino acid residue contained in the light chain variable region at position 38 as indicated by Kabat numbering; and
(b) the amino acid residue contained in the heavy chain variable region at position 45 as indicated by Kabat numbering, and the amino acid residue contained in the light chain variable region at position 44 as indicated by Kabat numbering.

The aforementioned amino acid residues that do not electrically repel each other are preferably amino acid residues selected from each of two sets selected from the group consisting of the aforementioned (X) to (Z), and where the two sets are selected from among the combinations of (X) and (Y), (X) and (Z), (Y) and (Z), and (Z) and (Z).

In addition, the present invention provides a method for regulating association of the heavy chains and light chains of an antibody.

A preferred embodiment of the method for regulating association of the present invention is a method for regulating association of the heavy chains and light chains of an antibody, comprising modifying nucleic acids so that one set or two or more sets of amino acid residues selected from the group consisting of the sets of amino acid residues shown in (a) to (c) below become amino acid residues that electrically repel each other:
(a) the amino acid residue contained in CH1 at position 147 as indicated by EU numbering, and the amino acid residue contained in CL at position 180 as indicated by EU numbering;
(b) the amino acid residue contained in CH1 at position 147 as indicated by EU numbering, and the amino acid residue contained in CL at position 131 as indicated by EU numbering; and
(c) the amino acid residue contained in CH1 at position 175 as indicated by EU numbering, and the amino acid residue contained in CL at position 160 as indicated by EU numbering.

Another embodiment of the present invention provides a method for regulating association in an antibody, further comprising modifying nucleic acids so that amino acid residues of the set of amino acid residues shown in (d) below are amino acid residues that electrically repel each other:
(d) the amino acid residue contained in CH1 at position 213 as indicated by EU numbering, and the amino acid residue contained in CL at position 123 as indicated by EU numbering.

Another preferred embodiment of the method for regulating association of the present invention is a method for regulating association of the heavy chains and light chains of an antibody, comprising modifying nucleic acids so that one set or two or more sets of amino acid residues selected from the group consisting of the sets of amino acid residues shown in (a) to (c) below become amino acid residues that do not electrically repel each other:
(a) the amino acid residue contained in CH1 at position 147 as indicated by EU numbering, and the amino acid residue contained in CL at position 180 as indicated by EU numbering;
(b) the amino acid residue contained in CH1 at position 147 as indicated by EU numbering, and the amino acid residue contained in CL at position 131 as indicated by EU numbering; and
(c) the amino acid residue contained in CH1 at position 175 as indicated by EU numbering, and the amino acid residue contained in CL at position 160 as indicated by EU numbering.

Another embodiment of the present invention provides a method for regulating association in an antibody, further comprising modifying nucleic acids so that amino acid residues of the set of amino acid residues indicated in (d) below are amino acid residues that do not electrically repel each other:
(d) the amino acid residue contained in CH1 at position 213 as indicated by EU numbering, and the amino acid residue contained in CL at position 123 as indicated by EU numbering.

According to the method for regulating association of the present invention, a desired bispecific antibody can be obtained preferentially and efficiently as previously described. Namely, a desired heteromeric multimer in the form of a bispecific antibody can be efficiently formed from a monomer mixture.

The phrase "modify nucleic acids" in the above-mentioned methods of the present invention refers to modifying nucleic acids so that they correspond to amino acid residues introduced by the "modifications" of the present invention. More specifically, it refers to modifying the nucleic acids encoding the original (pre-modified) amino acid residues to the nucleic acids encoding the amino acid residues that are to be introduced by the modification. Ordinarily, it means performing gene manipulations or mutation treatment that would result in at least one nucleotide insertion, deletion, or substitution to the original nucleic acid so that codons encoding amino acid residues of interest is formed. More specifically, codons encoding the original amino acid residues are substituted with codons encoding the amino acid residues that are to be introduced by the modification. Such nucleic acid modification can be performed suitably by those skilled in the art using known techniques such as site-specific mutagenesis and PCR mutagenesis.

In addition, the present invention provides nucleic acids that encode an antibody of the present invention. Moreover, vectors carrying the nucleic acids are also included in the present invention.

The nucleic acids of the present invention are ordinarily carried by (inserted into) suitable vectors and then introduced into host cells. These vectors are not particularly limited so long as the inserted nucleic acid is stably maintained. For example, when using *E. coli* as the host, the cloning vector is preferably a pBluescript vector (Stratagene) and such, but various commercially available vectors may be used. Expression vectors are particularly useful as vectors for producing the polypeptides of the present invention. Expression vectors are not particularly limited so long as they can express polypeptides in test tubes, *E. coli*, cultured cells, or individual organisms. For example, preferred vectors include pBEST vector (Promega) for expression in test tubes, pET vector (Invitrogen) for *E. coli*, pME18S-FL3 vector (GenBank Accession No. AB009864) for cultured cells, and pME18S vector (Mol. Cell Biol. 8:466-472 (1998)) for individual organisms. Insertion of a DNA of the present invention into vectors can be performed using, for example, In-Fusion Advantage PCR Cloning Kit (Clontech).

Further, the present invention provides host cells carrying the above described nucleic acids. The host cells are not particularly limited, and various host cells such as *E. coli* and various animal cells can be used according to the purpose. The host cells may be used, for example, as a production system to produce and express the antibodies or the polypeptides of the present invention. In vitro and in vivo production systems are available for polypeptide production systems. Production systems that use eukaryotic cells or prokaryotic cells are examples of in vitro production systems.

Eukaryotic cells that can be used as a host cell include, for example, animal cells, plant cells, and fungal cells. Animal cells include: mammalian cells, for example, CHO (J. Exp. Med. (1995) 108:945), COS, 3T3, myeloma, BHK (baby hamster kidney), HeLa, C127, HEK293, Bowes melanoma cells, and Vero; amphibian cells such as *Xenopus laevis* oocytes (Valle, et al. (1981) Nature 291:338-340); and insect cells (e.g., *Drosophila* S2, Sf9, Sf21, and Tn5). In the expression of the antibodies of the present invention, CHO-DG44, CHO-DX11B, COS7 cells, and BHK cells can be suitably used. Among animal cells, CHO cells are particularly preferable for large-scale expression.

Vectors can be introduced into a host cell by known methods, for example, by calcium phosphate methods, the DEAE-dextran methods, methods using cationic liposome DOTAP (Boehringer-Mannheim), electroporation methods (Current protocols in Molecular Biology edit. Ausubel et al. (1987) Publish. John Wiley & Sons, Section 9.1-9.9), lipofection, lipofectamine methods (GIBCO-BRL), or microinjection methods. Moreover, gene introduction to polypeptide expression can also be carried out using the Free Style 293 Expression System (Invitrogen).

Plant cells include, for example, *Nicotiana tabacum*-derived cells known as a protein production system. Calluses can be cultured from these cells to produce the antibodies of the present invention.

Known protein expression systems are those using fungal cells including yeast cells, for example, cells of genus *Saccharomyces* such as *Saccharomyces cerevisiae* and *Saccharomyces pombe*; and cells of filamentous fungi, for example, cells of genus *Aspergillus* such as *Aspergillus niger*. These cells can be used as a host to produce the antibodies of the present invention.

Bacterial cells can be used in the production systems using prokaryotic cells. Examples of bacterial cells include *Streptococcus, Staphylococcus, E. coli, Steptomyces, Bacillus subtilis* as well as the *E. coli* described above. Such cells can be used to produce the antibodies of the present invention.

When producing an antibody using a host cell of the present invention, the polynucleotide encoding an antibody of the present invention may be expressed by culturing the host cells transformed with the expression vector containing the polynucleotide. The culture can be performed using known methods. For example, when using animal cells as a host, DMEM, MEM, RPMI 1640, or IMDM may be used as the culture medium, and may be used with serum supplements such as FBS or fetal calf serum (FCS). Serum-free cultures are also acceptable. The preferred pH is about 6 to 8 during the course of culturing. Culture is carried out typically at about 30° C. to 40° C. for about 15 to 200 hours. Medium is exchanged, aerated, or agitated, as necessary.

On the other hand, production systems using animals or plants may be used as systems for producing polypeptides in vivo. A polynucleotide of interest is introduced into an animal or plant and the polypeptide is produced in the body of the animal or plant and then collected. The "host" of the present invention includes such animals and plants.

For secreting host cell-expressed polypeptides into the lumen of the endoplasmic reticulum, periplasmic space, or extracellular environment, suitable secretion signals can be incorporated into the polypeptides of interest. These signals may be intrinsic or foreign to the polypeptides of interest.

When the polypeptides of the present invention are secreted into the culture media, the polypeptides produced by the above-mentioned method can be harvested by collecting the media. When the polypeptides of the present invention are produced inside cells, first, the cells are lysed, and then these polypeptides are collected.

Animals to be used for the production system include mammals and insects. Mammals such as goats, pigs, sheep, mice, and cattle may be used (Vicki Glaser, SPECTRUM Biotechnology Applications (1993)). Alternatively, the mammals may be transgenic animals.

For example, a polynucleotide encoding an antibody of the present invention may be prepared as a fusion gene with a gene encoding a polypeptide specifically produced in milk, such as the goat β-casein. Polynucleotide fragments containing the fusion gene are injected into goat embryos, which are then introduced back to female goats. The desired antibody can be obtained from milk produced by the transgenic goats, which are born from the goats that received the embryos, or from their offspring. Appropriate hormones may be administered to the transgenic goats to increase the volume of milk containing the antibody produced by the transgenic goats (Ebert et al., Bio/Technology 12: 699-702 (1994)).

Insects such as silkworms may also be used for producing the antibodies of the present invention. Baculoviruses carrying a polynucleotide encoding an antibody of interest can be used to infect silkworms, and the antibody of interest can be obtained from their body fluids of (Susumu et al., Nature 315: 592-594 (1985)).

Plants used for producing the antibodies of the present invention include, for example, tobacco. When tobacco is used, a polynucleotide encoding an antibody of interest is inserted into a plant expression vector, for example, pMON 530, and then the vector is introduced into a bacterium, such as *Agrobacterium tumefaciens*. The bacteria are then used to infect tobacco such as *Nicotiana tabacum*, and the desired antibodies can be recovered from the tobacco leaves (Ma et al., Eur. J. Immunol. 24: 131-138 (1994)).

The resulting antibody may be isolated from the inside or outside (such as the medium and milk) of host cells, and purified as a substantially pure and homogenous antibody. Methods are not limited to any specific method and any standard method for isolating and purifying antibodies may be used. Antibodies may be isolated and purified, by appropriately selecting and combining, for example, ammonium sulfate or ethanol precipitation, acid extraction, chromatographic columns, filtration, ultrafiltration, salting out, solvent precipitation, solvent extraction, distillation, immunoprecipitation, SDS-polyacrylamide gel electrophoresis, isoelectric focusing, dialysis, recrystallization, and others.

Chromatographies include, for example, affinity chromatographies, ion exchange chromatographies such as anion exchange chromatographies and cation exchange chromatographies, phosphocellulose chromatographies, hydrophobic (interaction) chromatographies, gel filtrations, reverse-phase chromatographies, adsorption chromatographies, hydroxylapatite chromatographies, and lectin chromatographies (Strategies for Protein Purification and Characterization: A Laboratory Course Manual. Ed Daniel R. Marshak et al., Cold Spring Harbor Laboratory Press, 1996). These chromatographies can be carried out using liquid phase chromatographies such as HPLC and FPLC. Examples of the affinity chromatography columns include protein A columns and protein G columns. Examples of the proteins A columns include Hyper D, POROS, and Sepharose F. F. (Pharmacia).

An antibody can be modified freely and peptide portions can be deleted from it by treating the antibody with an appropriate protein modifying enzyme before or after antibody purification, as necessary. Such protein modifying enzymes include, for example, trypsins, chymotrypsins, lysyl endopeptidases, protein kinases, and glucosidases.

In another preferred embodiment, the present invention also includes methods for producing the antibodies of the present invention, such methods including the steps of culturing the host cells of the present invention as described above and collecting the antibodies from such cell culture.

Moreover, the present invention relates to pharmaceutical compositions (pharmaceutical agents) comprising an antibody of the present invention and a pharmaceutically acceptable carrier. In the present invention, pharmaceutical compositions ordinarily refer to pharmaceutical agents for treating or preventing, or testing and diagnosing diseases.

The pharmaceutical compositions of the present invention can be formulated by methods known to those skilled in the art. Moreover, the antibodies of the present invention can be formulated in combination with other pharmaceutical substances, as required. For example, they can be used parenterally in the form of an injection of a sterile solution or suspension with water or another pharmaceutically acceptable liquid. For example, they may be formulated as unit doses that meet the requirements for the preparation of pharmaceuticals by appropriately combining with pharmaceutically acceptable carriers or media, specifically with sterile water, physiological saline, a vegetable oil, emulsifier, suspension, detergent, stabilizer, flavoring agent, excipient, vehicle, preservative, binder, or such. In such preparations, the amount of active ingredient is adjusted such that the dose falls within an appropriately pre-determined range.

Sterile compositions for injection can be formulated using vehicles such as distilled water for injection, according to standard protocols for formulation.

Aqueous solutions for injection include, for example, physiological saline and isotonic solutions containing dextrose or other adjuvants (for example, D-sorbitol, D-mannose, D-mannitol, and sodium chloride). Appropriate solubilizers, for example, alcohols (ethanol and such), polyalcohols (propylene glycol, polyethylene glycol, and such), non-ionic detergents (polysorbate 80™, HCO-50, and such), may be used in combination.

Oils include sesame and soybean oils. Benzyl benzoate and/or benzyl alcohol can be used in combination as solubilizers. Buffers (for example, phosphate buffer and sodium acetate buffer), soothing agents (for example, procaine hydrochloride), stabilizers (for example, benzyl alcohol and phenol), and/or antioxidants can also be combined. Prepared injectables are generally filled into appropriate ampules.

The pharmaceutical compositions of the present invention are preferably administered parenterally. For example, the compositions may be injections, transnasal compositions, transpulmonary compositions or transdermal compositions. For example, such compositions can be administered systemically or locally by intravenous injection, intramuscular injection, intraperitoneal injection, subcutaneous injection, or such.

The administration methods can be appropriately selected in consideration of a patient's age and symptoms. The dose of a pharmaceutical composition containing an antibody or a polynucleotide encoding an antibody may be, for example, from 0.0001 to 1000 mg/kg for each administration. Alternatively, the dose may be, for example, from 0.001 to 100,000 mg per patient. However, the doses are not necessarily limited to the ranges described above. The doses and administration methods vary depending on a patient's weight, age, symptoms, and such. Those skilled in the art can select appropriate doses and administration methods in consideration of the factors described above.

Amino acids contained in the amino acid sequences of the present invention may be post-translationally modified (for example, the modification of an N-terminal glutamine into a pyroglutamic acid by pyroglutamylation is well-known to those skilled in the art). Naturally, such post-translationally modified amino acids are included in the amino acid sequences in the present invention.

All prior art documents cited in the present specification are incorporated herein by reference.

EXAMPLES

Hereinbelow, the present invention will be specifically described with reference to the Examples, but the present invention is not limited thereto.

Example 1

Search for Sites that Regulate the CH1/CL Interface

It was thought that by introducing mutations into each of the CH1 and CL domains of a bispecific antibody, and utilizing the electrical charge at the CH1/CL interface to regulate the CH1/CL interface, only the H chain and L chain for an antigen A specifically associate, and only the H chain and L chain for an antigen B specifically associate. Hereinafter, it is referred to as regulation of the CH1/CL interface. A search to found out the positions where the CH1/CL interface can be controlled was carried out using a crystal structure model. Amino acids maintain interactions between side chains through hydrophobic interaction, electrical interaction, hydrogen bonding and the like. These interactions are known to occur between side chains present within a range of about 4 Å. Therefore, amino acids were found in a PDB model 1HZH, wherein the distance between amino acids present in CH1 and amino acids present in CL at the interface between CH1 and CL is about 4 Å. The sites at which the amino acids are found are each summarized in FIG. 1 and Table 1 (Summary of Modified Sites). The amino acid numbers shown in Table 1 are indicated in accordance with EU numbering (Sequences of proteins of immunological interest, NIH Publication No. 91-3242). In addition, subsequent amino acid numbers are also indicated in accordance with EU numbering. In the present example, IgG1 was used for the H chain, and IgK (Kappa) was used for the L chain.

TABLE 1

|   | CH   | CL   |
|---|------|------|
| 1 | K147 | T180 |
| 2 | Q175 | Q160 |
| 3 | K213 | E123 |
| 4 | K133 | N138 |
| 5 | K147 | S131 |
| 6 | H168 | T164 |
| 7 | F170 | L135 |

In order to regulate the CH1/CL interface using the electrical charge of amino acids, the amino acids found in CH1 of the H chain or CL of the L chain (Table 1) were substituted with positively charged Lys or His and negatively charged Glu or Asp. More specifically, constant regions: TH2 and TH11, in which amino acids of CH1 of human G1d (SEQ ID NO: 1) were substituted with positively charged Lys; and TH1, TH3, TH4, TH9, TH10, and TH12, in which amino acids of CH1 of human G1d (SEQ ID NO: 1) were substituted with negatively charged Glu or Asp were prepared. Similarly, constant regions: TL2, TL4, TL5, TL6, TLB, and TL12, in which amino acids of human CL (SEQ ID NO: 13) were substituted with positively charged Lys; TL11, in which amino acids of human CL (SEQ ID NO: 13) were substituted with His; and TL1, TL3, TL7, TL9, TL10, and TL13, in which amino acids of human CL (SEQ ID NO: 13) were substituted with negatively charged Glu or Asp were prepared. The names (name), sites of mutation (mutation) and sequence numbers of the prepared constant regions are summarized in Table 2 (Summary of Modified Sites).

TABLE 2

| CH1 | | | CL | | |
|---|---|---|---|---|---|
| name | mutation | SEQ ID NO | name | mutation | SEQ ID NO |
| TH1 | K147E | SEQ ID NO: 002 | TL1 | T180E | SEQ ID NO: 014 |
| TH2 | Q175K | SEQ ID NO: 003 | TL2 | T180K | SEQ ID NO: 015 |
| TH3 | Q175E | SEQ ID NO: 004 | TL3 | Q160E | SEQ ID NO: 016 |
| TH4 | K213E | SEQ ID NO: 005 | TL4 | Q160K | SEQ ID NO: 017 |
| TH9 | K133E | SEQ ID NO: 006 | TL5 | E123K | SEQ ID NO: 018 |
| TH10 | H168D | SEQ ID NO: 007 | TL6 | N138K | SEQ ID NO: 019 |
| TH11 | F170K | SEQ ID NO: 008 | TL7 | N138E | SEQ ID NO: 020 |
| TH12 | F170E | SEQ ID NO: 009 | TL8 | S131K | SEQ ID NO: 021 |
| | | | TL9 | S131E | SEQ ID NO: 022 |
| | | | TL10 | T164D | SEQ ID NO: 023 |
| | | | TL11 | T164H | SEQ ID NO: 024 |
| | | | TL12 | L135K | SEQ ID NO: 025 |
| | | | TL13 | L135E | SEQ ID NO: 026 |

Example 2

Method for Screening Sites that Regulate the CH1/CL Interface, and Preparation and Analysis of each Antibody Effects on the regulation of the CH1/CL interface of the found amino acids were confirmed using the method described below. Screening was carried out using an anti-GPC3 antibody. First, expression vectors of the H chain and L chain were constructed. An H chain expression vector having the H chain variable region GpH7 (SEQ ID NO: 34) and the H chain constant region prepared in Example 1, and an L chain expression vector having the L chain variable region GpL16 (SEQ ID NO: 35) and the L chain constant region prepared in Example 1 were each constructed in accordance with Reference Example 1. Next, combinations of the prepared H chain and L chain expression vectors were selected in the manner described below. A single H chain in which the amino acid at the found site has a positive charge or negative charge was selected from among the constant regions prepared in Example 1. In this case, a mutation was not always introduced. For example, although position 147 of TH1 is substituted with Glu, a mutation is not introduced because the amino acid at position 147 of G1d is Lys and it initially has a positive charge. Next, L chains, which have mutations at the positions corresponding to the mutated positions in CH1 of the selected H chains according Table 1, were selected from Table 2. For example, when TH1 is selected for the H chain, TL1 and TL2 were selected for the L chain, since the amino acid at position 147 of CH1 and the amino acid at position 180 of CL are expected to interact as the CH1/CL interface. Subsequently, the selected two L chains were mixed with the selected one H chain, and antibodies were expressed in accordance with Reference Example 1. Finally, the expressed antibodies were analyzed in accordance with Reference Example 3 or Reference Example 4, and modifications effective for regulating the CH1/CL interface were screened according to the expression ratio of each antibody. Since IgG is composed of a complex of two H chains and two L chains, when one type of H chain and two types of L chains are mixed and expressed, three combinations are expected to be expressed. For example, when combinations of TH1 as the H chain, and TL1 and TL2 as the L chains are expressed, three combinations below are expressed (FIG. 2): H chain_1:H chain_2:L chain_1:L chain_2=TH1:TH1:TL1:TL1 (indicated as TH1/TL1), H chain_1:H chain_2:L chain_1:L chain_2=TH1:TH1:TL1:TL2 (indicated as TH1/TL1_TL2) H chain_1:H chain_2:L chain_1:L chain_2=TH1:TH1:TL2:TL2 (indicated as TH1/TL2). In the case that association of the H chain and L chain is not selective, the H chain and L chains are expected to be expressed in the ratio TH1/TL1:TH1/TL1_TL2:TH1/TL2=1:2:1, since the two L chains are present in equal amounts. However, in the case that the H chain preferentially binds to only either one of the L chains at the CH1/CL interface, it is thought that only that combination is expressed preferentially. For example, in the case that the amino acid at position 147 of CH1 and the amino acid at position 180 of CL are involved at the CH1/CL interface, when TH1 is expressed as the H chain, and TL1 and TL2 are expressed as the L chains, the combination of TH1, in which the amino acid at position 147 of CH1 is Glu (negatively charged), and TL2, in which the amino acid at position 180 of the L chain CL is Lys (positively charged), is expected to be expressed preferentially. However, in the case that the amino acid at position 147 of CH1 and the amino acid at position 180 of CL are not interacting on the CH1/CL interface, since the association of the H chain and L chain is not selective, they are expected to be expressed in the ratio of TH1/TL1:TH1/TL1_TL2:TH1/TL2=1:2:1. In this manner, modifications effective for regulation of the CH1/CL interface (modifications involved in the CH1/CL interface) were screened by mixing and expressing one type of H chain and two types of L chains, and using the expression balance thereof as an indicator.

Combinations of H chain and L chains are summarized in Table 3 (Combinations of H Chain and L Chains Used in Expression; Sites of Mutation in H Chain and L Chain also Shown).

TABLE 3

| Hch | | | Lch | | |
|---|---|---|---|---|---|
| name | mutation | SEQ ID NO | name | mutation | SEQ ID NO |
| G1d | K147K | SEQ ID NO: 001 | TL1_TL2 | T180E_T180K | SEQ ID NO: 014, SEQ ID NO: 015 |
| TH1 | K147E | SEQ ID NO: 002 | TL1_TL2 | T180E_T180K | SEQ ID NO: 014, SEQ ID NO: 015 |
| TH2 | Q175K | SEQ ID NO: 003 | TL3_TL4 | Q160E_Q160K | SEQ ID NO: 016, SEQ ID NO: 017 |
| TH3 | Q175E | SEQ ID NO: 004 | TL3_TL4 | Q160E_Q160K | SEQ ID NO: 016, SEQ ID NO: 017 |
| G1d | K213K | SEQ ID NO: 001 | k0_TL5 | E123E_E123K | SEQ ID NO: 013, SEQ ID NO: 018 |
| TH4 | K213E | SEQ ID NO: 005 | k0_TL5 | E123E_E123K | SEQ ID NO: 013, SEQ ID NO: 018 |
| G1d | K133K | SEQ ID NO: 001 | TL6_TL7 | N138K_N138E | SEQ ID NO: 019, SEQ ID NO: 020 |
| TH9 | K133E | SEQ ID NO: 006 | TL6_TL7 | N138K_N138E | SEQ ID NO: 019, SEQ ID NO: 020 |
| G1d | K147K | SEQ ID NO: 001 | TL8_TL9 | S131K_S131E | SEQ ID NO: 021, SEQ ID NO: 022 |
| TH1 | K147E | SEQ ID NO: 002 | TL8_TL9 | S131K_S131E | SEQ ID NO: 021, SEQ ID NO: 022 |
| G1d | H168H | SEQ ID NO: 001 | TL10_TL11 | T164D_T164H | SEQ ID NO: 023, SEQ ID NO: 024 |
| TH10 | H168D | SEQ ID NO: 007 | TL10_TL11 | T164D_T164H | SEQ ID NO: 023, SEQ ID NO: 024 |
| TH11 | F170K | SEQ ID NO: 008 | TL12_TL13 | L135K_L135E | SEQ ID NO: 025, SEQ ID NO: 026 |
| TH12 | F170E | SEQ ID NO: 009 | TL12_TL13 | L135K_L135E | SEQ ID NO: 025, SEQ ID NO: 026 |

Antibodies were expressed in accordance with the combinations shown in Table 3, and the effects on regulation of the selected CH1/CL interface were confirmed. At that time, antibodies of one type of H chain and one type of L chain were simultaneously expressed, and used as a control in analyses. Antibodies were expressed in accordance with the method of Reference Example 1.

Figure 3:
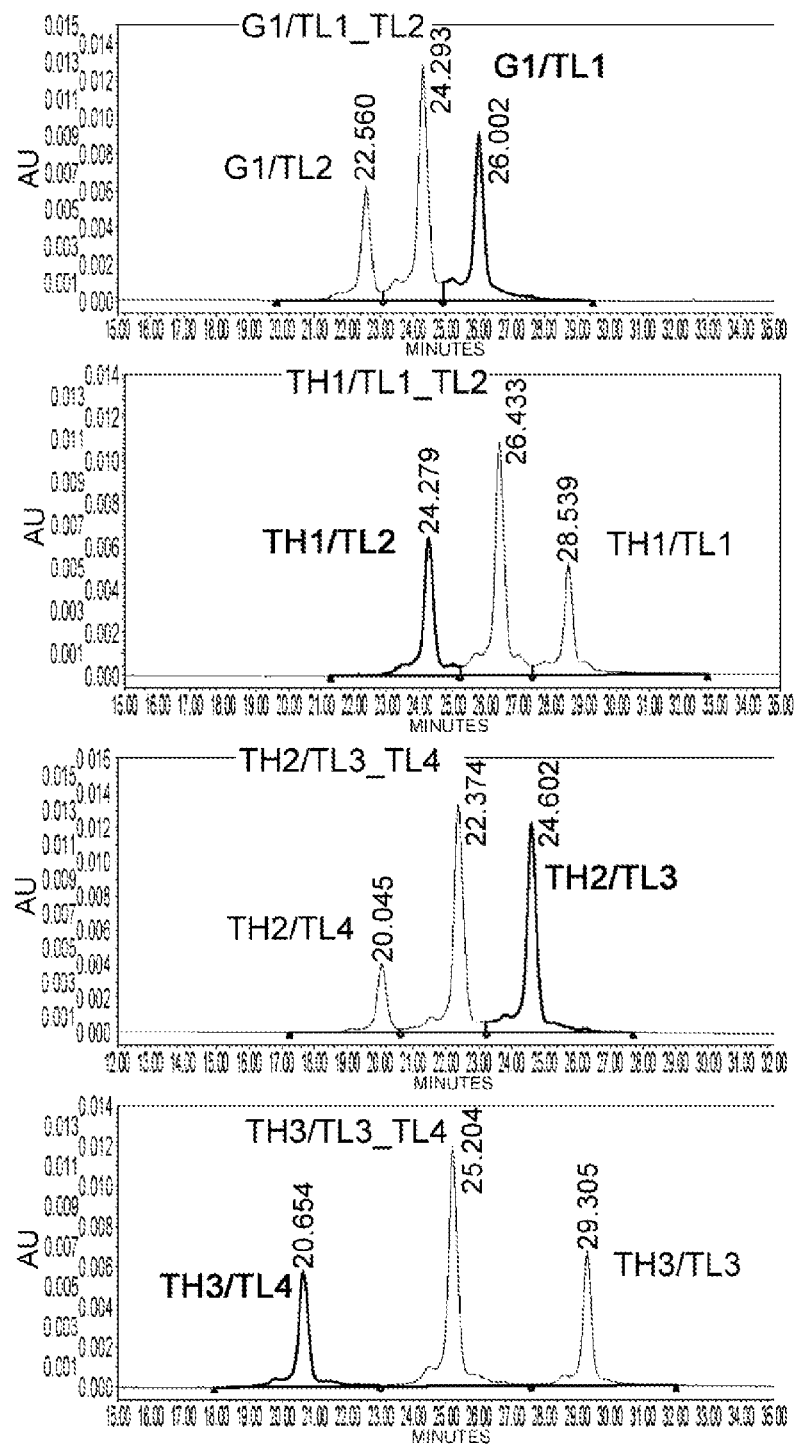
FIG. 3 depicts graphs showing results of the ALEX analysis of each of the antibodies.
Figure 4:
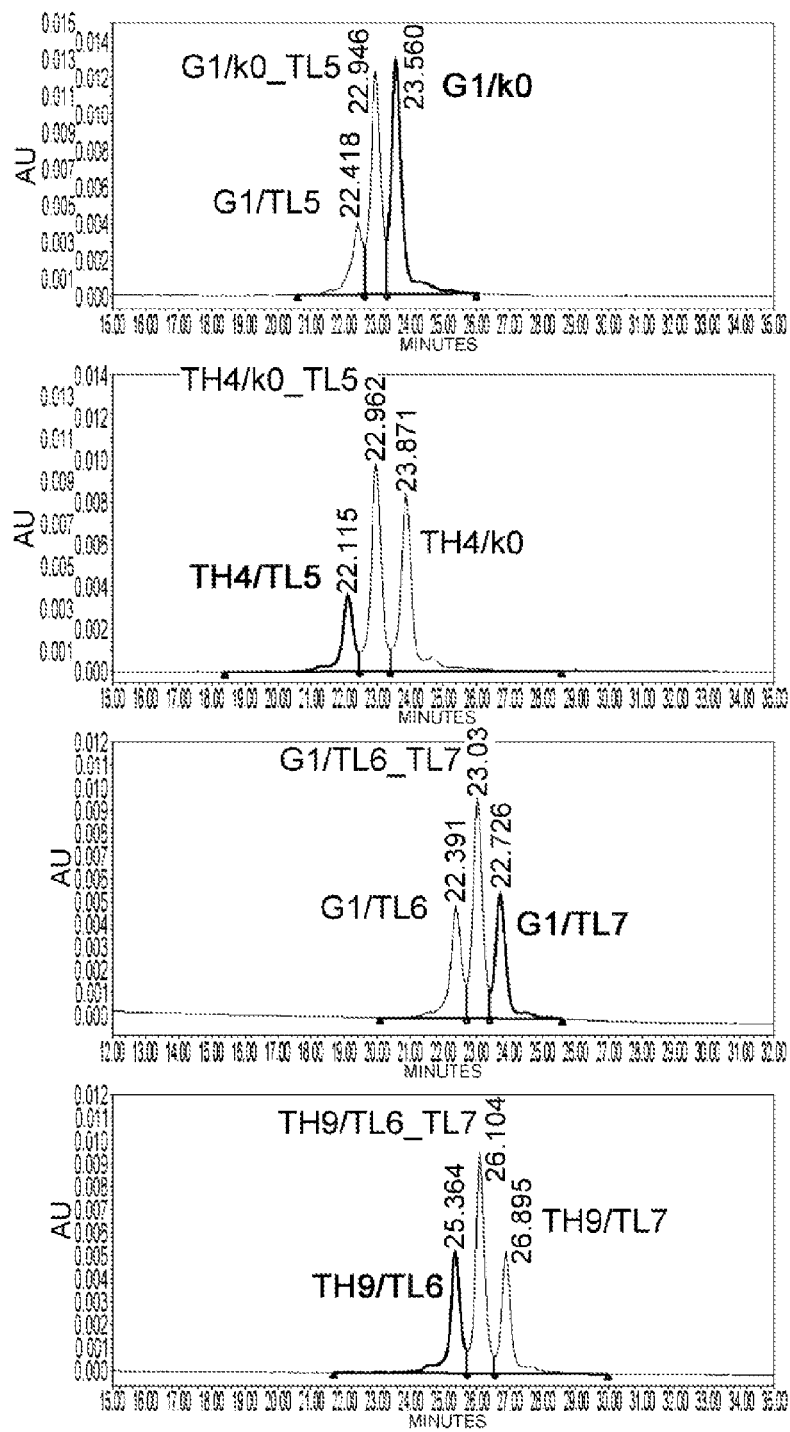
FIG. 4 depicts graphs showing results of the ALEX analysis of each of the antibodies.
Figure 5:
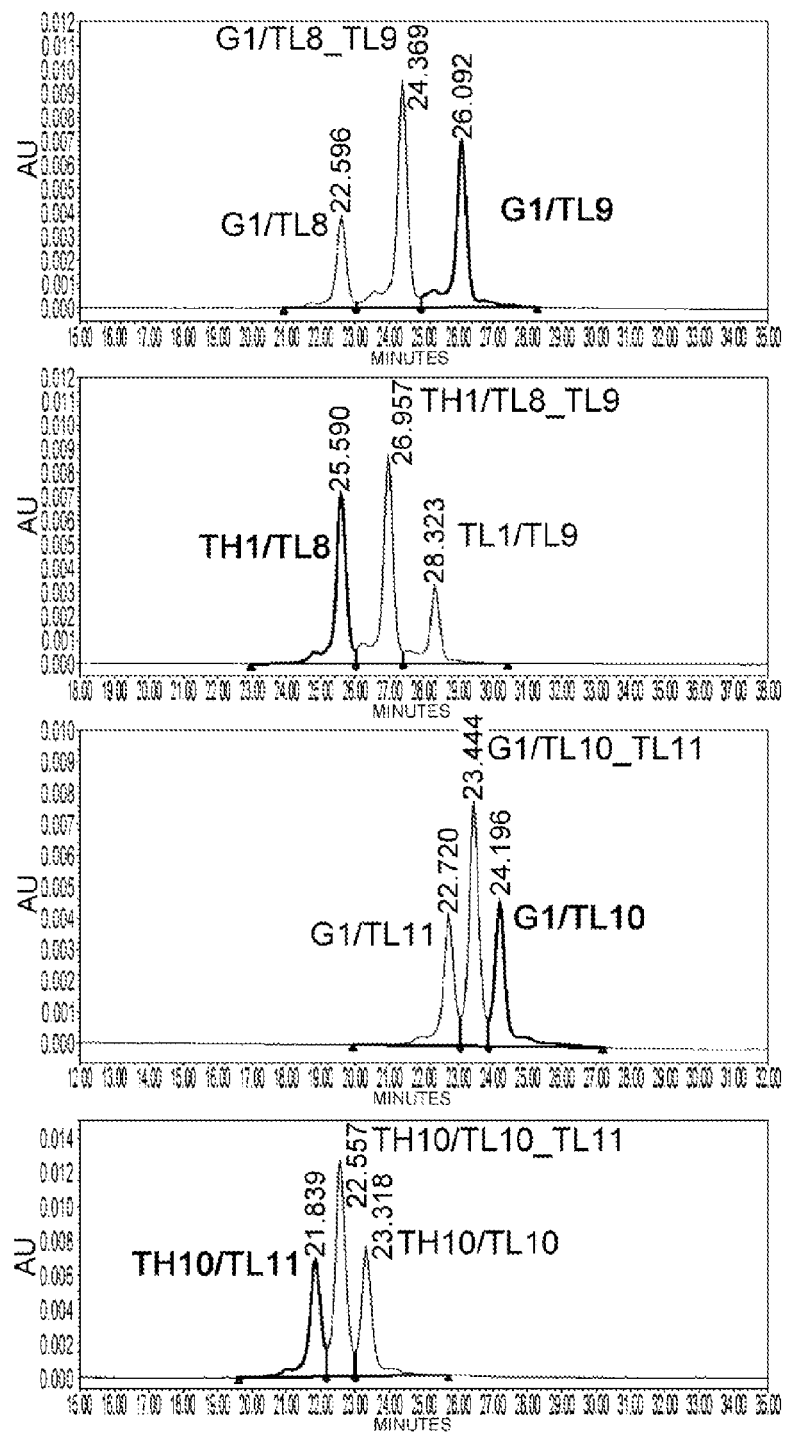
FIG. 5 depicts graphs showing results of the ALEX analysis of each of the antibodies.
Figure 6:
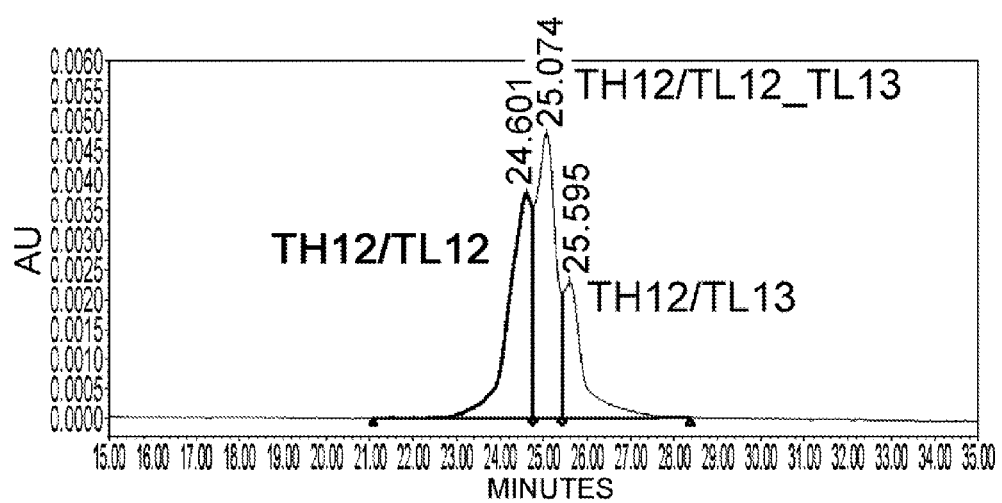
FIG. 6 depicts a graph showing results of the AIEX analysis of each of the antibodies.
Figure 7:
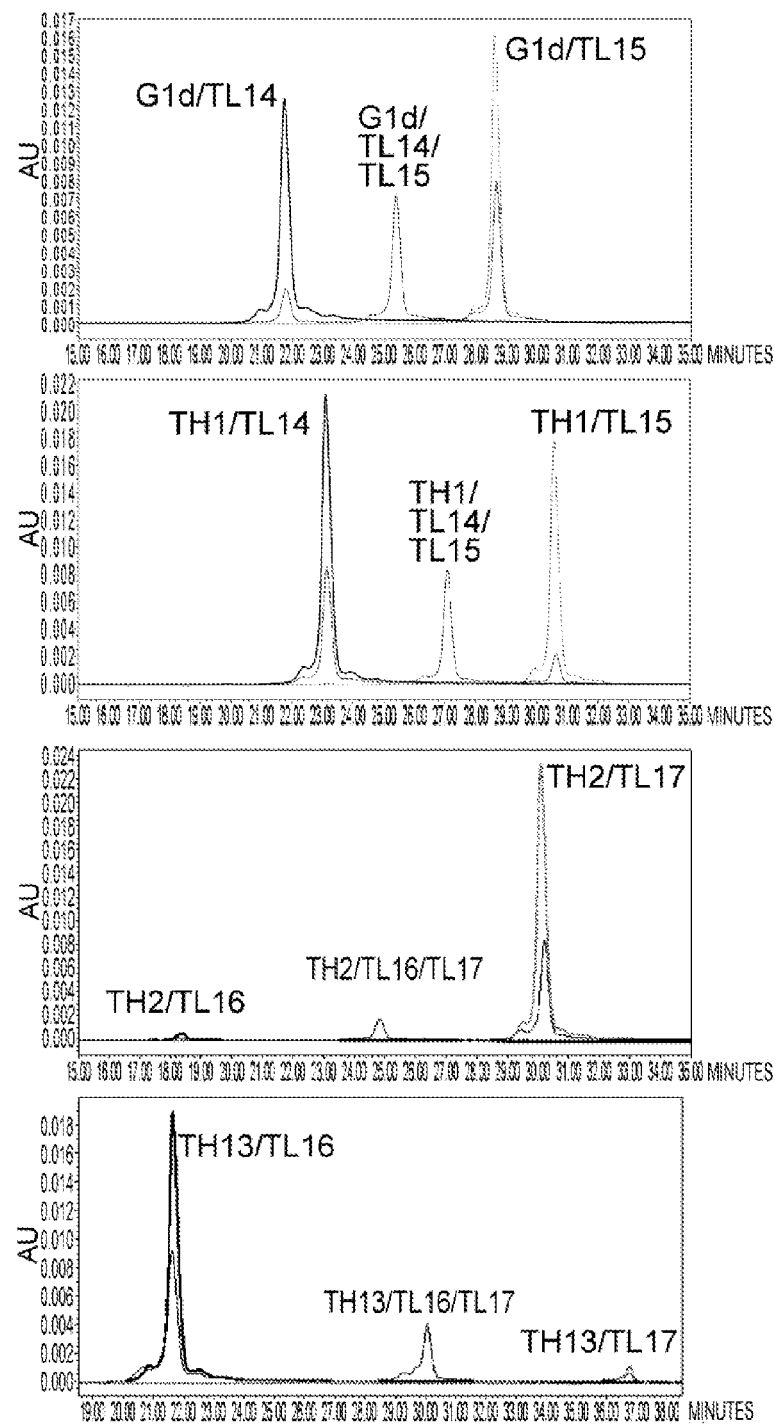
FIG. 7 depicts graphs showing results of the CIEX analysis of each of the antibodies.
Figure 8:
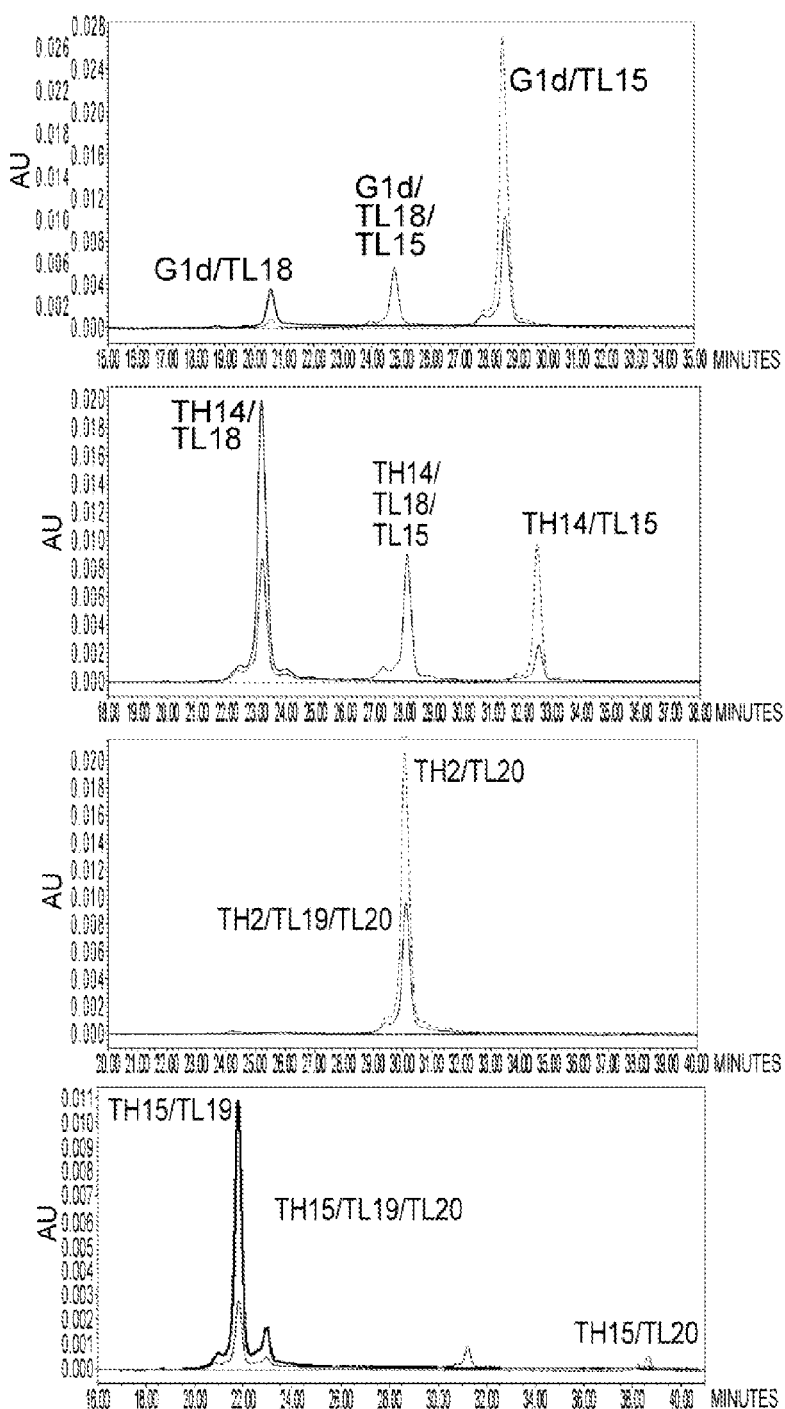
FIG. 8 depicts graphs showing results of the CIEX analysis of each of the antibodies.

The prepared antibodies were analyzed by AIEX in accordance with the method of Reference Example 3. Data of the AIEX analysis are summarized in FIG. 3. Since an anion exchange column is used in the AIEX analysis, positively charged antibodies are eluted more rapidly. The analyzed data are summarized and shown in Table 4. The peaks are indicated as peaks 1, 2, and 3 in the order of increasing elution time. The ratio of each peak was calculated with the total of the peak areas being 100%.

Figure 2:
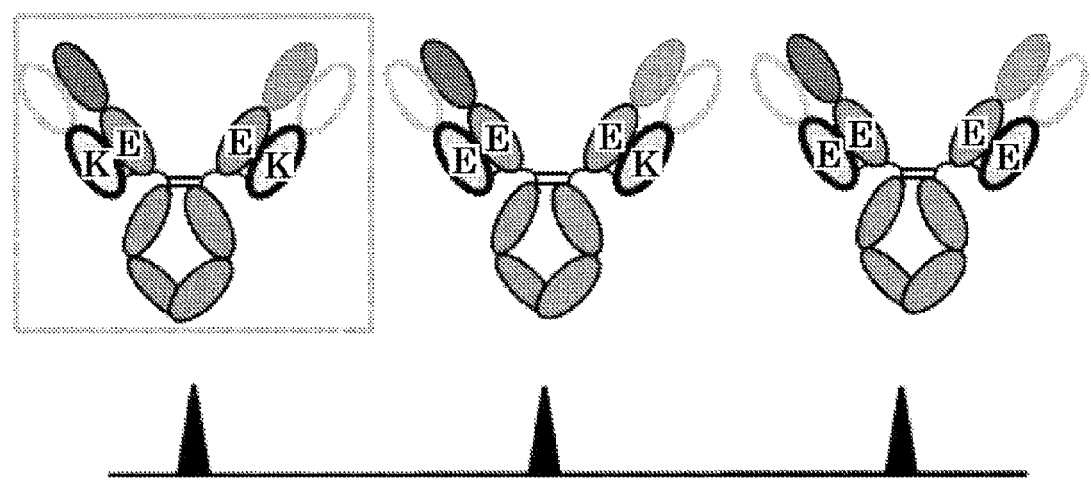
FIG. 2 is a conceptual antibody showing possible combinations of H chain and L chain when the antibody is prepared by mixing one type of H chain and two types of L chains. Mutated sites which gave a large proportion of the antibody with the combination of E and K as shown in the box are thought to interact electrically.

As shown in FIG. 2, in the case that the positions introduced with mutations form electrical interaction, the ratio of antibody at the position of the gray-colored peak increases. Namely, mutation sites at which the ratio of the gray-colored antibody is greater than 25% are thought to be interacting electrically.

TABLE 4

| Hch | | Lch | | peak 1 | peak 2 | peak 3 |
|---|---|---|---|---|---|---|
| name | mutation | name | mutation | % | % | % |
| G1d | K147K | TL1 | T180E | | | 100 |
| G1d | K147K | TL2 | T180K | 100 | | |
| G1d | K147K | TL1_TL2 | T180E_T180K | 20.2 | 44.2 | 35.6 |
| TH1 | K147E | TL1 | T180E | | | 100 |
| TH1 | K147E | TL2 | T180K | 100 | | |
| TH1 | K147E | TL1_TL2 | T180E_T180K | 28.5 | 46.7 | 24.8 |
| TH2 | Q175K | TL3 | Q160E | | | 100 |
| TH2 | Q175K | TL4 | Q160K | 100 | | |
| TH2 | Q175K | TL3_TL4 | Q160E_Q160K | 13 | 44 | 43 |
| TH3 | Q175E | TL3 | Q160E | | | 100 |
| TH3 | Q175E | TL4 | Q160K | 100 | | |
| TH3 | Q175E | TL3_TL4 | Q160E_Q160K | 25 | 49.9 | 24.8 |
| G1d | K213K | k0 | E123E | | | 100 |
| G1d | K213K | TL5 | E123K | 100 | | |
| G1d | K213K | k0_TL5 | E123E_E123K | 15.1 | 39.3 | 45.6 |
| TH4 | K213E | k0 | E123E | | | 100 |
| TH4 | K213E | TL5 | E123K | 100 | | |
| TH4 | K213E | k0_TL5 | E123E_E123K | 17.5 | 41.3 | 41.2 |
| G1d | K133K | TL6 | N138K | 100 | | |
| G1d | K133K | TL7 | N138E | | | 100 |
| G1d | K133K | TL6_TL7 | N138K_N138E | 27.3 | 44 | 28.7 |
| TH9 | K133E | TL6 | N138K | 100 | | |
| TH9 | K133E | TL7 | N138E | | | 100 |
| TH9 | K133E | TL6_TL7 | N138K_N138E | 29.1 | 44 | 26.9 |
| G1d | K213K | TL8 | S131K | 100 | | |
| G1d | K213K | TL9 | S131E | | | 100 |
| G1d | K213K | TL8_TL9 | S131K_S131E | 17.8 | 45.7 | 36.7 |
| TH1 | K147E | TL8 | S131K | 100 | | |
| TH1 | K147E | TL9 | S131E | | | 100 |
| TH1 | K147E | TL8_TL9 | S131K_S131E | 36.9 | 44.1 | 19 |
| G1d | H168H | TL10 | T164D | | | 100 |
| G1d | H168H | TL11 | T164H | 100 | | |

TABLE 4-continued

| Hch | | Lch | | peak 1 | peak 2 | peak 3 |
|---|---|---|---|---|---|---|
| name | mutation | name | mutation | % | % | % |
| G1d | H168H | TL10_TL11 | T164D_T164H | 27 | 43.3 | 29.7 |
| TH10 | H168D | TL10 | T164D | | | 100 |
| TH10 | H168D | TL11 | T164H | 100 | | |
| TH10 | H168D | TL10_TL11 | T164D_T164H | 27 | 44.4 | 28.6 |
| TH11 | F170K | TL12 | L135K | 100 | | |
| TH11 | F170K | TL13 | L135E | | | 100 |
| TH11 | F170K | TL12_TL13 | L135K_L135E | not expressed | | |
| TH12 | F170E | TL12 | L135K | 100 | | |
| TH12 | F170E | TL13 | L135E | | | 100 |
| TH12 | F170E | TL12_TL13 | L135K_L135E | 38.1 | 41.6 | 20.3 |

As a result of examining various sites of modification in this manner, positions 147, 175, and 213 of the H chain, and positions 123, 131, 160, and 180 of the L chain were thought to be effective for regulating the CH1/CL interface. In addition, it was found that modifications of only position 147 of the H chain and position 123 of the L chain reported in WO 2006/106905 and WO 2007/147901 were inadequate for causing specific association of the H chain and L chain, and the specific association is possible only by combining modifications found in the present example.

Example 3

Preparation and Analysis of Antibodies with Combined Sites of Modification

It was thought that the CH1/CL interface is regulated more effectively by combining the sites of K147, Q175, and K213 in CH1 and the sites of E123, S131, Q160, and T180 in CL as found in Example 2, which were thought to have considerable effects in regulating the CH1/CL interface. The combinations of modifications in the prepared antibodies, and the expressed antibodies are summarized in Table 5 (Summary of Modification Sites).

TABLE 5

| Hch | | | Lch | | |
|---|---|---|---|---|---|
| name | mutation | SEQ ID NO | name | mutation | SEQ ID NO |
| G1d | K147K | SEQ ID NO: 001 | TL14_TL15 | T180K, S131K_T180E, S131E | SEQ ID NO: 027, SEQ ID NO: 028 |
| TH1 | K147E | SEQ ID NO: 002 | TL14_TL15 | T180K, S131K_T180E, S131E | SEQ ID NO: 027, SEQ ID NO: 028 |
| TH2 | Q175K | SEQ ID NO: 003 | TL16_TL17 | T180K, S131K, Q160K_T180E, S131E, Q160E | SEQ ID NO: 029, SEQ ID NO: 030 |
| TH13 | K147E, Q175E | SEQ ID NO: 010 | TL16_TL17 | T180K, S131K, Q160K_T180E, S131E, Q160E | SEQ ID NO: 029, SEQ ID NO: 030 |
| G1d | K147K | SEQ ID NO: 001 | TL18_TL15 | T180K, S131K, E123K_T180E, S131E, E123E | SEQ ID NO: 031, SEQ ID NO: 028 |
| TH14 | K147E, K213E | SEQ ID NO: 011 | TL18_TL15 | T180K, S131K, E123K_T180E, S131E, E123E | SEQ ID NO: 031, SEQ ID NO: 028 |
| TH2 | Q175K | SEQ ID NO: 003 | TL19_TL17 | T180K, S131K, Q160K, E123K_T180E, S131E, Q160E | SEQ ID NO: 032, SEQ ID NO: 030 |
| TH15 | K147E, Q175E, K213E | SEQ ID NO: 012 | TL19_TL17 | T180K, S131K, Q160K, E123K_T180E, S131E, Q160E, E123E | SEQ ID NO: 032, SEQ ID NO: 030 |

Preparation of expression vectors of the H chain or L chain introduced with mutations, and antibody expression were carried out in accordance with Reference Example 1, and analyses of the prepared antibodies were carried out in accordance with Reference Example 3 or Reference Example 4. The results are summarized in Table 6.

TABLE 6

| Hch | | Lch | | peak 1 | peak 2 | peak 3 |
|---|---|---|---|---|---|---|
| name | mutation | name | mutation | % | % | % |
| G1d | K147K | TL14 | T180K, S131K | 100 | | |
| G1d | K147K | TL15 | T180E, S131E | | | 100.0 |
| G1d | K147K | TL14_TL15 | T180K, S131K, T180E, S131E | 11.5 | 43.6 | 44.9 |
| TH1 | K147E | TL14 | T180K, S131K | 100.0 | | |
| TH1 | K147E | TL15 | T180E, S131E | | | 100.0 |
| TH1 | K147E | TL14_TL15 | T180K, S131K_T180E, S131E | 46.1 | 43.4 | 10.4 |
| TH2 | Q175K | TL16 | T180K, S131K, Q160K | not expressed | | |
| TH2 | Q175K | TL17 | T180E, S131E, Q160E | | | 100.0 |
| TH2 | Q175K | TL16_TL17 | T180K, S131K, Q160K_T180E, S131E, Q160E | 1.4 | 16.5 | 82.0 |
| TH13 | K147E, Q175E | TL16 | T180K, S131K, Q160K | 100.0 | | |
| TH13 | K147E, Q175E | TL17 | T180E, S131E, Q160E | | | not expressed |
| TH13 | K147E, Q175E | TL16_TL17 | T180K, S131K, Q160K_T180E, S131E, Q160E | 70.2 | 26.4 | 3.4 |
| G1d | K147K | TL18 | T180K, S131K, E123K | not expressed | | |
| G1d | K147K | TL15 | T180E.S131E | | | 100.0 |
| G1d | K147K | TL18_TL15 | T180K, S131K, E123K_T180E, S131E, E123E | 5.1 | 35.3 | 59.6 |
| TH14 | K147E, K213E | TL18 | T180K, S131K, E123K | 100.0 | | |
| TH14 | K147E, K213E | TL15 | T180E, S131E | | | 100.0 |
| TH14 | K147E, K213E | TL18_TL15 | T180K, S131K, E123K_T180E, S131E, E123E | 44.5 | 44.4 | 11.1 |
| TH2 | Q175K | TL19 | T180K, S131K, Q160K, E123K | not expressed | | |
| TH2 | Q175K | TL17 | T180E, S131E, Q160E | | | 100.0 |
| TH2 | Q175K | TL19_TL17 | T180K, S131K, Q160K, E123K_T180E, S131E, Q160E, | | | 93.1 |
| TH15 | K147E, Q175E, K213E | TL19 | T180K, S131K, Q160K, E123K | 100.0 | | |
| TH15 | K147E, Q175E, K213E | TL17 | T180E, S131E, Q160E | | | not expressed |
| TH15 | K147E, Q175E, K213E | TL19_TL17 | T180K, S131K, Q160K, E123K_T180E, S131E, Q160E | 78.1 | 19.9 | 2.0 |

When Table 4 and Table 6 are compared, it is understood that the ratio of targeted combinations of the H chain and L chain is increased by combining modifications, as compared with the introduction of a single modification. Consequently, it is thought that an antibody in which only the H chain and L chain of interest have associated can be efficiently prepared by combining modifications.

Example 4

Expression and Analysis of Bispecific Antibodies

In Example 3, preparation of bispecific antibodies (bispecific Abs) for TH2, TH13, and TH15 of H chains, and TL16, TL17, TL19, and TL20 of L chains that showed considerable effects for regulating the CH1/CL interface was taken thought. In this example, bispecific antibodies were prepared using an anti-IL6R antibody and an anti-GPC3 antibody.

The constant regions of H chain (SEQ ID NO: 59) and L chain (SEQ ID NO: 60) recognizing anti-IL6R, and the constant regions of H chain (SEQ ID NO: 61) and L chain (SEQ ID NO: 62) recognizing anti-GPC3 were substituted with TH2, TH13, and TH15 for the constant regions of the H chain, and with TL16, TL17, TL19, and TL20 for CL of the L chain. Moreover, an H chain introduced with a Knob into Hole (KiH) modification (WO 96/27011) was prepared to avoid association between homogeneous H chains. The mutation sites in these prepared antibodies and the expressed antibodies are summarized in Table 7 (Combinations of H Chain and L Chain of Each Bispecific Antibody).

TABLE 7

| | Ach | | | | Bch | | | | |
|---|---|---|---|---|---|---|---|---|---|
| NAME | VH | CH | VL | CL | VH | CH | VL | CL | comment |
| 4ch_001 | MH0 | G1d | ML0 | k0 | GpH7 | G1d | GpL16 | k0 | |
| 4ch_002 | MH0 | G1dk | ML0 | k0 | GpH7 | G1dh | GpL16 | k0 | KiH |
| 4ch_003 | MH0 | TH2 | ML0 | TL17 | GpH7 | TH13 | GpL16 | TL16 | CH1/CL_1 |
| 4ch_004 | MH0 | TH2k | ML0 | TL17 | GpH7 | TH13h | GpL16 | TL16 | KiH + CH1/CL_1 |
| 4ch_011 | MH0 | TH2k | ML0 | TL17 | GpH7 | TH13h | ML0 | TL17 | |
| 4ch_012 | MH0 | TH2k | GpL16 | TL16 | GpH7 | TH13h | GpL16 | TL16 | |
| 4ch_005 | MH0 | TH2 | ML0 | TL17 | GpH7 | TH15 | GpL16 | TL19 | CH1/CL_2 |
| 4ch_006 | MH0 | TH2k | ML0 | TL17 | GpH7 | TH15h | GpL16 | TL19 | KiH + CH1/CL_2 |
| 4ch_015 | MH0 | TH2k | ML0 | TL17 | GpH7 | TH15h | ML0 | TL17 | |
| 4ch_016 | MH0 | TH2k | GpL16 | TL19 | GpH7 | TH15h | GpL16 | TL19 | |
| 4ch_001 | MH0 | G1d | ML0 | k0 | GpH7 | G1d | GpL16 | k0 | |
| 4ch_002 | MH0 | G1dk | ML0 | k0 | GpH7 | G1dh | GpL16 | k0 | KiH |
| 4ch_007 | MH0 | TH13 | ML0 | TL16 | GpH7 | TH2 | GpL16 | TL17 | CH1/CL_1 |
| 4ch_008 | MH0 | TH13k | ML0 | TL16 | GpH7 | TH2h | GpL16 | TL17 | KiH + CH1/CL_1 |

TABLE 7-continued

| NAME | Ach | | | | Bch | | | | comment |
| --- | --- | --- | --- | --- | --- | --- | --- | --- | --- |
| | VH | CH | VL | CL | VH | CH | VL | CL | |
| 4ch_013 | MH0 | TH13k | ML0 | TL16 | GpH7 | TH2h | ML0 | TL16 | |
| 4ch_014 | MH0 | TH13k | GpL16 | TL17 | GpH7 | TH2h | GpL16 | TL17 | |
| 4ch_009 | MH0 | TH15 | ML0 | TL19 | GpH7 | TH2 | GpL16 | TL17 | CH1/CL_2 |
| 4ch_010 | MH0 | TH15k | ML0 | TL19 | GpH7 | TH2h | GpL16 | TL17 | KiH + CH1/CL_2 |
| 4ch_017 | MH0 | TH15k | ML0 | TL19 | GpH7 | TH2h | ML0 | TL19 | |
| 4ch_018 | MH0 | TH15k | GpL16 | TL17 | GpH7 | TH2h | GpL16 | TL17 | |

In Table 7 above, "k" is added after the variant name for those constant regions in which a "knob" modification was introduced into the H chain, and "h" is added after the variant name for those constant regions in which a "hole" modification was introduced. For example, "TH1k" indicates that a "knob" modification was introduced in addition to the TH1 mutation, and "TH1h" indicates that a "hole" modification was introduced in addition to the TH1 mutation. Preparation of expression vectors of the H chain or L chain into which a mutation has been introduced as well as expression of antibodies were carried out in accordance with Reference Example 1, and analyses of the prepared antibodies were carried out in accordance with the CIEX analysis method shown in Reference Example 4.

The combinations of H chains and L chains of the anti-IL6R antibody and anti-GPC3 antibody used in the bispecific antibodies are summarized in Table 8.

TABLE 8

| NAME | chain | VH name | VH mutation | VH SEQ ID NO | CH name | CH mutation | CH SEQ ID NO | VL name | VL mutation | VL SEQ ID NO | CL name | CL mutation | CL SEQ ID NO |
|---|---|---|---|---|---|---|---|---|---|---|---|---|---|
| 4ch_001 | Ach | MH0 | — | SEQ ID NO: 036 | G1d | K147K | SEQ ID NO: 001 | ML0 | — | SEQ ID NO: 037 | k0 | — | SEQ ID NO: 013 |
| 4ch_002 | Ach | MH0 | — | SEQ ID NO: 036 | G1dk | — | SEQ ID NO: 001 | ML0 | — | SEQ ID NO: 037 | k0 | — | SEQ ID NO: 013 |
| 4ch_003 | Ach | MH0 | — | SEQ ID NO: 036 | TH2 | Q175K | SEQ ID NO: 003 | ML0 | — | SEQ ID NO: 037 | TL17 | T180E, S131E, Q160E | SEQ ID NO: 030 |
| 4ch_004 | Ach | MH0 | — | SEQ ID NO: 036 | TH2k | Q175K | SEQ ID NO: 039 | ML0 | — | SEQ ID NO: 037 | TL17 | T180E, S131E, Q160E | SEQ ID NO: 030 |
| 4ch_011 | Ach | MH0 | — | SEQ ID NO: 036 | TH2k | Q175K | SEQ ID NO: 039 | GpL16 | — | SEQ ID NO: 035 | TL17 | T180E, S131E, Q160E | SEQ ID NO: 030 |
| 4ch_005 | Ach | MH0 | — | SEQ ID NO: 036 | TH2 | Q175K | SEQ ID NO: 003 | ML0 | — | SEQ ID NO: 037 | TL16 | T180K, S131K, Q160K | SEQ ID NO: 029 |
| 4ch_006 | Ach | MH0 | — | SEQ ID NO: 036 | TH2k | Q175K | SEQ ID NO: 039 | ML0 | — | SEQ ID NO: 037 | TL16 | T180K, S131K, Q160K | SEQ ID NO: 029 |
| 4ch_015 | Ach | MH0 | — | SEQ ID NO: 036 | TH2k | Q175K | SEQ ID NO: 039 | ML0 | — | SEQ ID NO: 037 | TL19 | T180E, S131E, Q160E | SEQ ID NO: 030 |
| 4ch_016 | Ach | MH0 | — | SEQ ID NO: 036 | TH2k | Q175K | SEQ ID NO: 039 | ML0 | — | SEQ ID NO: 037 | TL19 | T180K, S131K, Q160K, E123K | SEQ ID NO: 032 |
| 4ch_001 | Ach | MH0 | — | SEQ ID NO: 036 | G1d | K147K | SEQ ID NO: 001 | ML0 | — | SEQ ID NO: 037 | k0 | — | SEQ ID NO: 013 |
| 4ch_002 | Ach | MH0 | — | SEQ ID NO: 036 | G1dk | — | SEQ ID NO: 038 | ML0 | — | SEQ ID NO: 037 | k0 | — | SEQ ID NO: 013 |
| 4ch_007 | Ach | MH0 | — | SEQ ID NO: 036 | TH13 | K147E, Q175E | SEQ ID NO: 010 | ML0 | — | SEQ ID NO: 037 | TL16 | T180K, S131K, Q160K | SEQ ID NO: 029 |
| 4ch_008 | Ach | MH0 | — | SEQ ID NO: 036 | TH13k | K147E, Q175E | SEQ ID NO: 040 | ML0 | — | SEQ ID NO: 037 | TL16 | T180K, S131K, Q160K | SEQ ID NO: 029 |
| 4ch_013 | Ach | MH0 | — | SEQ ID NO: 036 | TH13k | K147E, Q175E | SEQ ID NO: 040 | GpL16 | — | SEQ ID NO: 035 | TL16 | T180K, S131K, Q160K | SEQ ID NO: 029 |
| 4ch_014 | Ach | MH0 | — | SEQ ID NO: 036 | TH13k | K147E, Q175E | SEQ ID NO: 040 | GpL16 | — | SEQ ID NO: 035 | TL17 | T180E, S131E, Q160E | SEQ ID NO: 030 |
| 4ch_009 | Ach | MH0 | — | SEQ ID NO: 036 | TH15 | K147E, Q175E, K213E | SEQ ID NO: 012 | ML0 | — | SEQ ID NO: 037 | TL19 | T180K, S131K, Q160K, E123K | SEQ ID NO: 032 |
| 4ch_010 | Ach | MH0 | — | SEQ ID NO: 036 | TH15k | K147E, Q175E, K213E | SEQ ID NO: 041 | ML0 | — | SEQ ID NO: 037 | TL19 | T180K, S131K, Q160K, E123K | SEQ ID NO: 032 |
| 4ch_017 | Ach | MH0 | — | SEQ ID NO: 036 | TH15k | K147E, Q175E, K213E | SEQ ID NO: 041 | ML0 | — | SEQ ID NO: 037 | TL19 | T180E, S131E, Q160E | SEQ ID NO: 030 |
| 4ch_018 | Ach | MH0 | — | SEQ ID NO: 036 | TH15k | K147E, Q175E, K213E | SEQ ID NO: 041 | GpL16 | — | SEQ ID NO: 035 | TL17 | T180E, S131E, Q160E | SEQ ID NO: 030 |
| 4ch_001 | Bch | GpH7 | — | SEQ ID NO: 034 | G1d | K147K | SEQ ID NO: 001 | GpL16 | — | SEQ ID NO: 035 | k0 | — | SEQ ID NO: 013 |
| 4ch_002 | Bch | GpH7 | — | SEQ ID NO: 034 | G1dh | — | SEQ ID NO: 042 | GpL16 | — | SEQ ID NO: 035 | k0 | — | SEQ ID NO: 013 |
| 4ch_003 | Bch | GpH7 | — | SEQ ID NO: 034 | TH13 | K147E, Q175E | SEQ ID NO: 010 | GpL16 | — | SEQ ID NO: 035 | TL16 | T180K, S131K, Q160K | SEQ ID NO: 029 |
| 4ch_004 | Bch | GpH7 | — | SEQ ID NO: 034 | TH13h | K147E, Q175E | SEQ ID NO: 044 | GpL16 | — | SEQ ID NO: 035 | TL16 | T180K, S131K, Q160K | SEQ ID NO: 029 |
| 4ch_011 | Bch | GpH7 | — | SEQ ID NO: 034 | TH13h | K147E, Q175E | SEQ ID NO: 044 | ML0 | — | SEQ ID NO: 037 | TL17 | T180E, S131E, Q160E | SEQ ID NO: 030 |
| 4ch_005 | Bch | GpH7 | — | SEQ ID NO: 034 | TH15 | K147E, Q175E, K213E | SEQ ID NO: 012 | GpL16 | — | SEQ ID NO: 035 | TL16 | T180K, S131K, Q160K | SEQ ID NO: 029 |
| 4ch_006 | Bch | GpH7 | — | SEQ ID NO: 034 | TH15h | K147E, Q175E, K213E | SEQ ID NO: 045 | GpL16 | — | SEQ ID NO: 035 | TL16 | T180K, S131K, Q160K, E123K | SEQ ID NO: 032 |
| 4ch_015 | Bch | GpH7 | — | SEQ ID NO: 034 | TH15h | K147E, Q175E, K213E | SEQ ID NO: 045 | ML0 | — | SEQ ID NO: 037 | TL17 | T180E, S131E, Q160E | SEQ ID NO: 030 |
| 4ch_016 | Bch | GpH7 | — | SEQ ID NO: 034 | TH15h | K147E, Q175E, K213E | SEQ ID NO: 045 | ML0 | — | SEQ ID NO: 037 | TL19 | T180K, S131K, Q160K, E123K | SEQ ID NO: 032 |
| 4ch_001 | Bch | GpH7 | — | SEQ ID NO: 034 | G1d | K147K | SEQ ID NO: 001 | GpL16 | — | SEQ ID NO: 035 | k0 | — | SEQ ID NO: 013 |
| 4ch_002 | Bch | GpH7 | — | SEQ ID NO: 034 | G1dh | — | SEQ ID NO: 042 | GpL16 | — | SEQ ID NO: 035 | k0 | — | SEQ ID NO: 013 |
| 4ch_007 | Bch | GpH7 | — | SEQ ID NO: 034 | TH2 | Q175K | SEQ ID NO: 003 | GpL16 | — | SEQ ID NO: 035 | TL17 | T180E, S131E, Q160E | SEQ ID NO: 030 |
| 4ch_008 | Bch | GpH7 | — | SEQ ID NO: 034 | TH2h | Q175K | SEQ ID NO: 043 | GpL16 | — | SEQ ID NO: 035 | TL17 | T180E, S131E, Q160E | SEQ ID NO: 030 |
| 4ch_014 | Bch | GpH7 | — | SEQ ID NO: 034 | TH2h | Q175K | SEQ ID NO: 043 | ML0 | — | SEQ ID NO: 037 | TL16 | T180K, S131K, Q160K | SEQ ID NO: 029 |
| 4ch_009 | Bch | GpH7 | — | SEQ ID NO: 034 | TH2 | Q175K | SEQ ID NO: 003 | GpL16 | — | SEQ ID NO: 035 | TL17 | T180E, S131E, Q160E | SEQ ID NO: 030 |
| 4ch_010 | Bch | GpH7 | — | SEQ ID NO: 034 | TH2h | Q175K | SEQ ID NO: 043 | GpL16 | — | SEQ ID NO: 035 | TL17 | T180E, S131E, Q160E | SEQ ID NO: 030 |
| 4ch_017 | Bch | GpH7 | — | SEQ ID NO: 034 | TH2h | Q175K | SEQ ID NO: 043 | ML0 | — | SEQ ID NO: 037 | TL19 | T180E, S131E, Q160E, E123K | SEQ ID NO: 030 |
| 4ch_018 | Bch | GpH7 | — | SEQ ID NO: 034 | TH2h | Q175K | SEQ ID NO: 043 | GpL16 | — | SEQ ID NO: 035 | TL17 | T180E, S131E, Q160E | SEQ ID NO: 030 |

Each combination is explained herein using 4ch_001, 4ch_002, 4ch_003, 4ch_004, 4ch_011, and 4ch_012 as examples. Modifications that regulate the CH1/CL interface are summarized in Table 8.

Figures 1, 9:
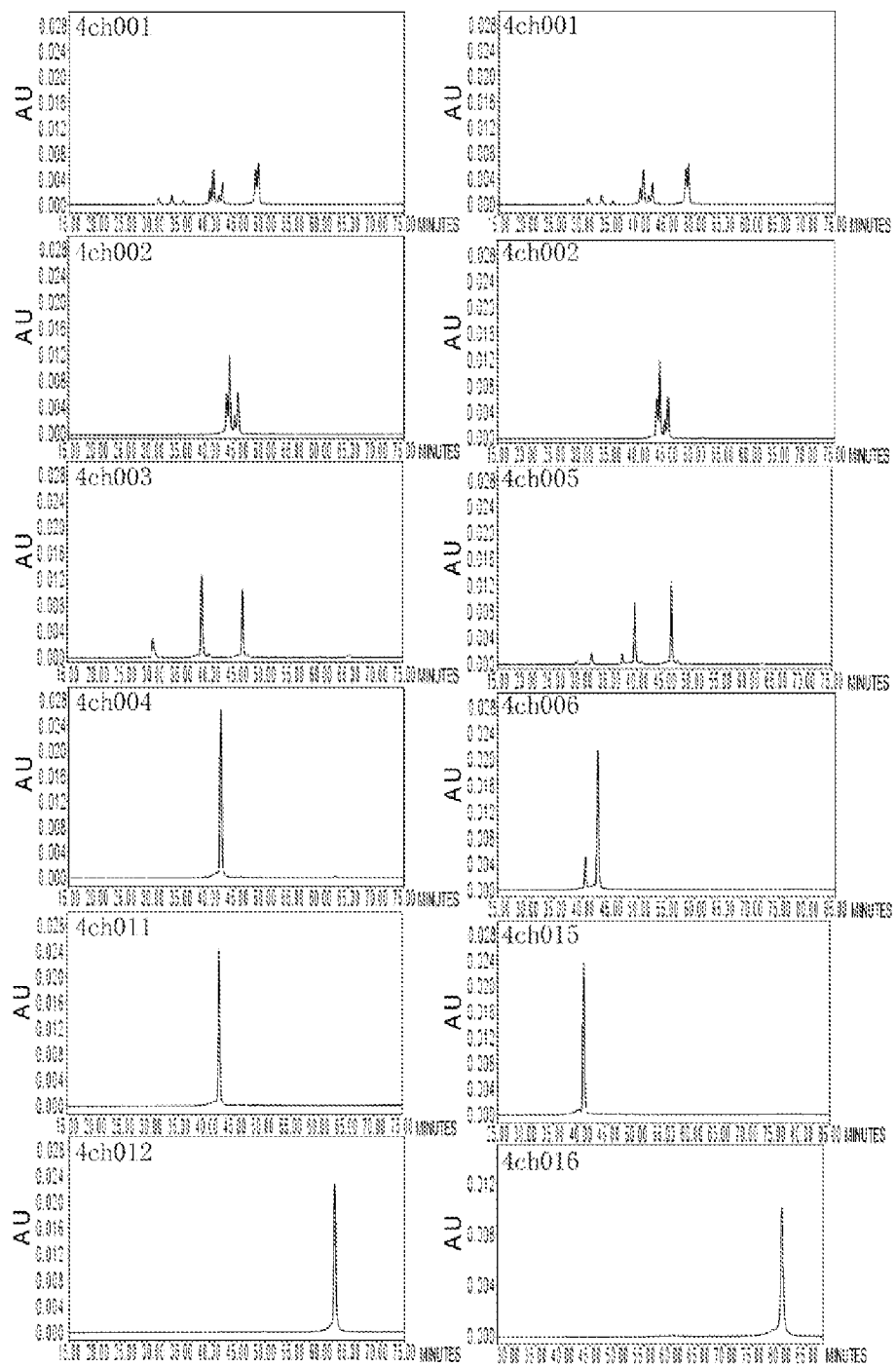
Figures 2, 9:
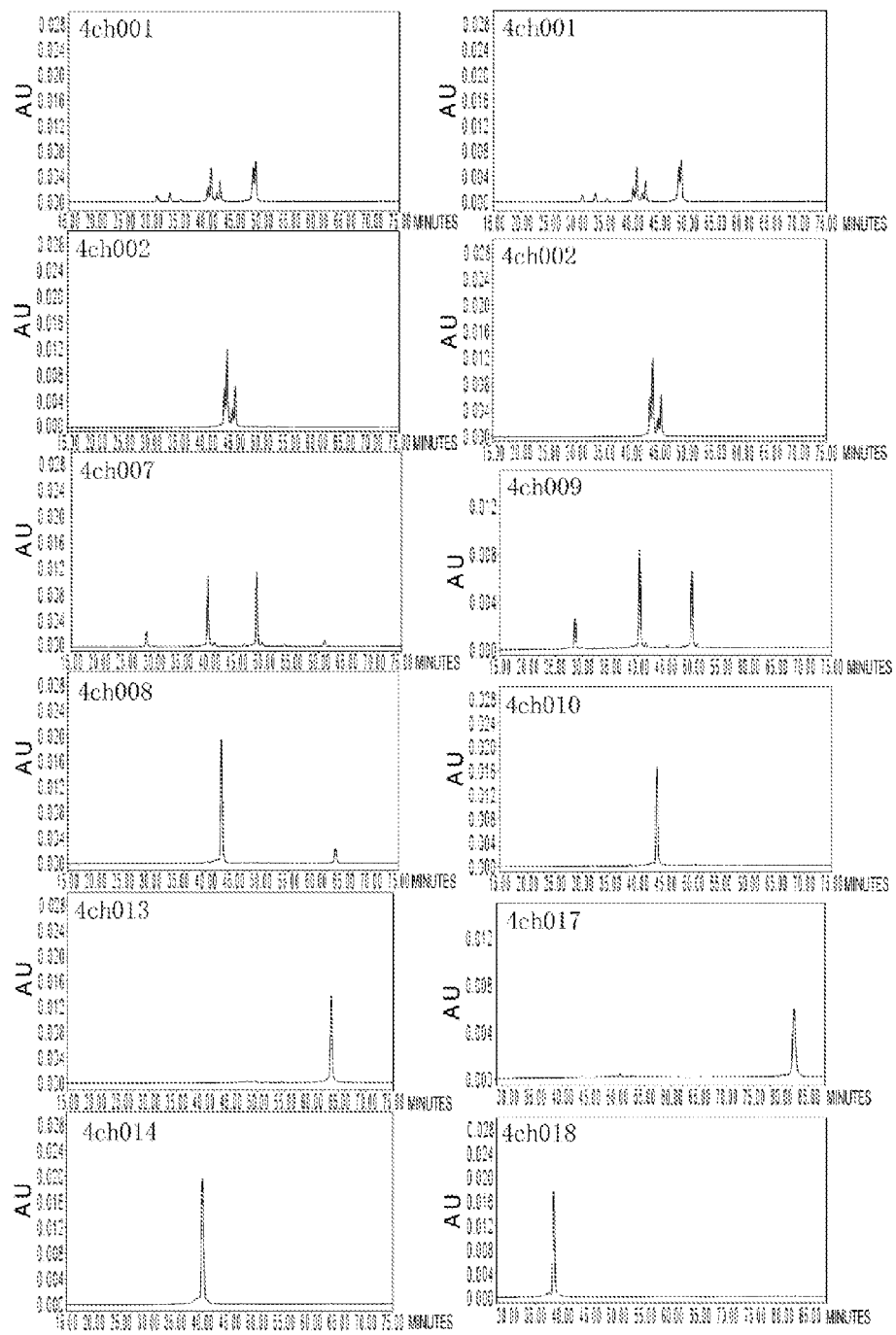

4ch_001 was expressed using H chains and L chains that do not have the introduction of modifications for regulating the CH1/CL interface and the KiH modification. 4ch_002 was expressed using H chains and L chain into which the KiH modification was introduced. 4ch_003 was expressed using H chains and L chains into which modifications for regulating the CH1/CL interface were introduced. 4ch_004 was expressed using H chains and an L chains into which the KiH modification and modifications for regulating the CH1/CL interface were introduced. In addition, 4ch_011 was expressed using the H chains of an anti-IL6R antibody and the H chains of an anti-GPC3 antibody into which the KiH modification and modifications for regulating the CH1/CL interface were introduced, and the L chains of an anti-IL6R antibody into which modifications for regulating the CH1/CL interface were introduced. 4ch_012 was expressed using the H chains of an anti-IL6R antibody and the H chains of an anti-GPC3 antibody into which the KiH modification and modifications for regulating the CH1/CL interface were introduced, and the L chains of an anti-GPC3 antibody into which modifications for regulating the CH1/CL interface were introduced. Each antibody was expressed in accordance with Reference Example 1, and analyzed by CIEX in accordance with Reference Example 4; and the results are summarized in FIGS. 9-1 and 9-2. The case of using the H-chain variable region of an anti-IL6R antibody is indicated with MH0, and the case of using the H chain variable region of an anti-GPC3 antibody is indicated with GpH7. The case of using the L chain variable region of an anti-IL6R antibody is indicated with ML0, and the case of using the L chain variable region of an anti-GPC3 antibody is indicated with GpL16. Multiple heterogeneous components which are thought to be various combinations of H chain and L chain were detected by chromatography for 4ch_001 which is not introduced with the mutations for CH1/CL interface control and KiH. In contrast, since the association of homogeneous H chains was suppressed in 4ch_002 with KiH mutation, the number of chromatographic peaks which are thought to be impurities are reduced. In addition, since the association of H chains and L chains was suppressed in 4ch_003 which uses TH2 and TH13 in H chains and TL16 and TL17 in L chains, into which modifications for regulating the CH1/CL interface were introduced, the number of chromatography peaks which are thought to represent impurities decreased. Moreover, it was revealed that 4ch_004 combining the mutations of KiH and modifications for regulating the CH1/CL interface is mostly the main peak. The reason that the chromatography peaks of 4ch_004 nearly coincide with the chromatography peaks of 4ch_011 is thought to be that their peaks are unable to be separated by chromatography due to their similar isoelectric points (pI). Studies were also conducted on 4ch_005, 4ch_006, 4ch_015, and 4ch_016, to which a different regulation of the CH1/CL interface from that for 4ch_004 had been applied; 4ch_007, 4ch_008, 4ch_013, and 4ch_014, in which modifications for regulating the CH1/CL interface introduced into 4ch_004 were interchanged between the anti-GPC3 antibody and the anti-IL6R antibody; and 4ch_009, 4ch_010, 4ch_017, and 4ch_018, in which modifications for regulating the CH1/CL interface introduced into 4ch_006 were interchanged between the anti-GPC3 antibody and the anti-IL6R antibody, using the same methods as 4ch_003, 4ch_004, 4ch_011, and 4ch_012. As a result, heterogeneous components presented in chromatogram were reduced significantly in comparison with 4ch_001.

From the above, it became apparent that bispecific antibodies can be efficiently prepared by combining modifications for regulating the CH1/CL interface and the KiH modification.

Example 5

Effects of Modifying Regulation of the CH1/CL Interface Using Different Antibodies It became apparent from Example 4 that the interface regulation using CH1/CL is useful for preparing bispecific antibodies. Therefore, the effect of regulating the CH1/CL interface was confirmed using an anti-CD3 antibody, M12 (H chain: SEQ ID NO: 54, L chain: SEQ ID NO: 57) and an anti-GPC3 antibody, GC33(2) (H chain: SEQ ID NO: 55, L chain: SEQ ID NO: 58). As with Example 4, bispecific antibodies were prepared using TH2, TH13, and TH15 in H chains and TL16, TL17, and TL19 in L chains which demonstrated considerable effects for regulating the CH1/CL interface.

The constant regions of the H chain (SEQ ID NO: 54) and the L chain (SEQ ID NO: 57) of CD3 recognizing antibody M12, and the constant regions of the H chain (SEQ ID NO: 55) and the L chain (SEQ ID NO: 58) of GPC3 recognizing antibody GC33(2), were substituted with TH2, TH13, and TH15 for CH1 of the H chain, and with TL16, TL17, and TL19 for CL of the L chain. Moreover, an H chain with Knob into Hole (KiH) modifications (Patent Document 1) was prepared to avoid association between homogeneous H chains. The mutation sites of these prepared antibodies and the expressed antibodies are summarized in Table 9 (Summary of Modification Sites).

TABLE 9

| NAME | Ach | | | | Bch | | | |
|---|---|---|---|---|---|---|---|---|
| | VH | CH | VL | CL | VH | CH | VL | CL |
| 4ch_001 | M12VH | G1d | M12VL | k0 | GC33(2)VH | G1d | GC33(2)VL | k0 |
| 4ch_004 | M12VH | TH2k | M12VL | TL17 | GC33(2)VH | TH13h | GC33(2)VL | TL16 |
| 4ch_006 | M12VH | TH2k | M12VL | TL17 | GC33(2)VH | TH15h | GC33(2)VL | TL19 |
| 4ch_001 | MH0 | G1d | ML0 | k0 | GpH7 | G1d | GpL16 | k0 |
| 4ch_008 | MH0 | TH13k | ML0 | TL16 | GpH7 | TH2h | GpL16 | TL17 |
| 4ch_010 | MH0 | TH15k | ML0 | TL19 | GpH7 | TH2h | GpL16 | TL17 |

TABLE 9-continued

| NAME | chain | VH name | mutation | SEQ ID NO | CH name | mutation | SEQ ID NO |
|---|---|---|---|---|---|---|---|
| 4ch_001 | Ach | M12VH | — | SEQ ID NO: 054 | E9CH | L234A, L235A, N297A | SEQ ID NO: 056 |
| 4ch_004 | Ach | M12VH | — | SEQ ID NO: 054 | TH2k | Q175K | SEQ ID NO: 039 |
| 4ch_006 | Ach | M12VH | — | SEQ ID NO: 054 | TH2k | Q175K | SEQ ID NO: 039 |
| 4ch_001 | Ach | MH0 | — | SEQ ID NO: 036 | E9CH | L234A, L235A, N297A | SEQ ID NO: 056 |
| 4ch_008 | Ach | MH0 | — | SEQ ID NO: 036 | TH13k | K147E, Q175E | SEQ ID NO: 040 |
| 4ch_010 | Ach | MH0 | — | SEQ ID NO: 036 | TH15k | K147E, Q175E, K213E | SEQ ID NO: 041 |
| 4ch_001 | Bch | GC33(2)VH | — | SEQ ID NO: 055 | E9CH | L234A, L235A, N297A | SEQ ID NO: 056 |
| 4ch_004 | Bch | GC33(2)VH | — | SEQ ID NO: 055 | TH13h | K147E, Q175E | SEQ ID NO: 044 |
| 4ch_006 | Bch | GC33(2)VH | — | SEQ ID NO: 055 | TH15h | K147E, Q175E, K213E | SEQ ID NO: 045 |
| 4ch_001 | Bch | GpH7 | — | SEQ ID NO: 034 | E9CH | L234A, L235A, N297A | SEQ ID NO: 056 |
| 4ch_008 | Bch | GpH7 | — | SEQ ID NO: 034 | TH2h | Q175K | SEQ ID NO: 043 |
| 4ch_010 | Bch | GpH7 | — | SEQ ID NO: 034 | TH2h | Q175K | SEQ ID NO: 043 |

| NAME | chain | VL name | mutation | SEQ ID NO | CL name | mutation | SEQ ID NO |
|---|---|---|---|---|---|---|---|
| 4ch_001 | Ach | M12VL | — | SEQ ID NO: 057 | k0 | — | SEQ ID NO: 013 |
| 4ch_004 | Ach | M12VL | — | SEQ ID NO: 057 | TL17 | T180E, S131E, Q160E | SEQ ID NO: 030 |
| 4ch_006 | Ach | M12VL | — | SEQ ID NO: 057 | TL17 | T180E, S131E, Q160E | SEQ ID NO: 030 |
| 4ch_001 | Ach | ML0 | — | SEQ ID NO: 037 | k0 | — | SEQ ID NO: 013 |
| 4ch_008 | Ach | ML0 | — | SEQ ID NO: 037 | TL16 | T180K, S131K, Q160K | SEQ ID NO: 029 |
| 4ch_010 | Ach | ML0 | — | SEQ ID NO: 037 | TL19 | T180K, S131K, Q160K, E123K | SEQ ID NO: 032 |
| 4ch_001 | Bch | GC33(2)VL | — | SEQ ID NO: 058 | k0 | — | SEQ ID NO. 013 |
| 4ch_004 | Bch | GC33(2)VL | — | SEQ ID NO: 058 | TL16 | T180K, S131K, Q160K | SEQ ID NO: 029 |
| 4ch_006 | Bch | GC33(2)VL | — | SEQ ID NO: 058 | TL19 | T180K, S131K, Q160K, E123K | SEQ ID NO: 032 |
| 4ch_001 | Bch | GpL16 | — | SEQ ID NO: 035 | k0 | — | SEQ ID NO: 013 |
| 4ch_008 | Bch | GpL16 | — | SEQ ID NO: 035 | TL17 | T180E, S131E, Q160E | SEQ ID NO: 030 |
| 4ch_010 | Bch | GpL18 | — | SEQ ID NO: 035 | TL17 | T180E, S131E, Q160E | SEQ ID NO: 030 |

Preparation of expression vectors of H chains and L chains with mutations and expression of antibodies were carried out in accordance with Reference Example 1, and analyses of the prepared antibodies were carried out in accordance with the CIEX analysis method shown in Reference Example 4.

It is apparent that regulation of the CH1/CL interface is also useful for preparing bispecific antibodies with an anti-CD3 antibody and an anti-GPC3 antibody.

Example 6

Combination of Regulation of the CH1/CL Interface and Regulation of the Variable Region Interface When preparing bispecific antibodies, introducing electrical repulsion into the variable regions VH and VL is known as a technique for allowing specific association of target H chains and L chains (Patent Document WO 2006/106905). Therefore, in order to efficiently express only target components, one is to cause repulsion between variable regions of the H chain and L chain, in addition to regulation of the CH1/CL interface. This is referred to as VH/VL interface regulation. MH01 (SEQ ID NO: 46), in which Gln at position 39 as indicated by Kabat numbering of the H chain of anti-IL6R was substituted with Lys; MH02 (SEQ ID NO: 47), in which the Gln was substituted with Glu; ML01 (SEQ ID NO: 50), in which Gln at position 38 as indicated by Kabat numbering of the L chain was substituted with Glu; and ML02 (SEQ ID NO: 51), in which the Glu was substituted with Lys, were prepared. Moreover, GpH71 (SEQ ID NO: 48), in which Gln at position 39 as indicated by Kabat numbering of the H chain of anti-GPC3 was substituted with Lys; GpH72 (SEQ ID NO: 49), in which the Gln was substituted with Glu; GpL161 (SEQ ID NO: 52), in which Gln at position 38 as indicated by Kabat numbering of the L chain was substituted with Glu; and GpL162 (SEQ ID NO: 53), in which the Gln was substituted with Lys, were respectively prepared. Preparation of antibody expression vectors was carried out in accordance with the method of Reference Example 1. Bispecific antibodies were expressed using the prepared antibodies. The combinations of modifications in the prepared antibodies and the expressed antibodies are summarized in Table 10.

TABLE 10

| NAME | chain | VH name | mutation | SEQ ID NO | CH name | mutation | SEQ ID NO |
|---|---|---|---|---|---|---|---|
| 4ch_1,2_004 | Ach | MH01 | Q39K | 46 | TH2k | Q175K | 39 |
| 4ch_1,2_006 | Ach | MH01 | Q39K | 46 | TH2k | Q175K | 39 |
| 4ch_2,1_008 | Ach | MH02 | Q39E | 47 | TH13k | K147E, Q175E | 40 |
| 4ch_2,1_010 | Ach | MH02 | Q39E | 47 | TH15k | K147E, Q175E, K213E | 41 |
| 4ch_1,2_004 | Bch | GpH72 | Q39E | 49 | TH13h | K147E, Q175E | 44 |

TABLE 10-continued

| NAME | chain | name | mutation | SEQ ID NO | name | mutation | SEQ ID NO |
|---|---|---|---|---|---|---|---|
| 4ch11_1,2_006 | Bch | GpH72 | Q39E | 49 | TH15h | K147E, Q175E, K213E | 45 |
| 4ch_2,1_008 | Bch | GpH71 | Q39K | 48 | TH2h | Q175K | 43 |
| 4ch_2,1_010 | Bch | GpH71 | Q39K | 48 | TH2h | Q175K | 43 |

| | | VL | | | CL | | |
|---|---|---|---|---|---|---|---|
| NAME | chain | name | mutation | SEQ ID NO | name | mutation | SEQ ID NO |
| 4ch_1,2_004 | Ach | ML01 | Q38E | 50 | TL17 | T180E, S131E, Q160E | 30 |
| 4ch_1,2_006 | Ach | ML01 | Q38E | 50 | TL17 | T180E, S131E, Q160E | 30 |
| 4ch_2,1_008 | Ach | ML02 | Q38K | 51 | TL16 | T180K, S131K, Q160K | 29 |
| 4ch_2,1_010 | Ach | ML02 | Q38K | 51 | TL19 | T180K, S131K, Q160K, E123K | 32 |
| 4ch_1,2_004 | Bch | GpL162 | Q38K | 53 | TL16 | T180K, S131K, Q160K | 29 |
| 4ch11_1,2_006 | Bch | GpL162 | Q38K | 53 | TL19 | T180K, S131K, Q160K, E123K | 32 |
| 4ch_2,1_008 | Bch | GpL161 | Q38E | 52 | TL17 | T180E, S131E, Q160E | 30 |
| 4ch_2,1_010 | Bch | GpL161 | Q38E | 52 | TL17 | T180E, S131E, Q160E | 30 |

Antibody expression was carried out in accordance with Reference Example 1, and analyses of the prepared antibodies were carried out in accordance with Reference Example 4.

Figure 10:
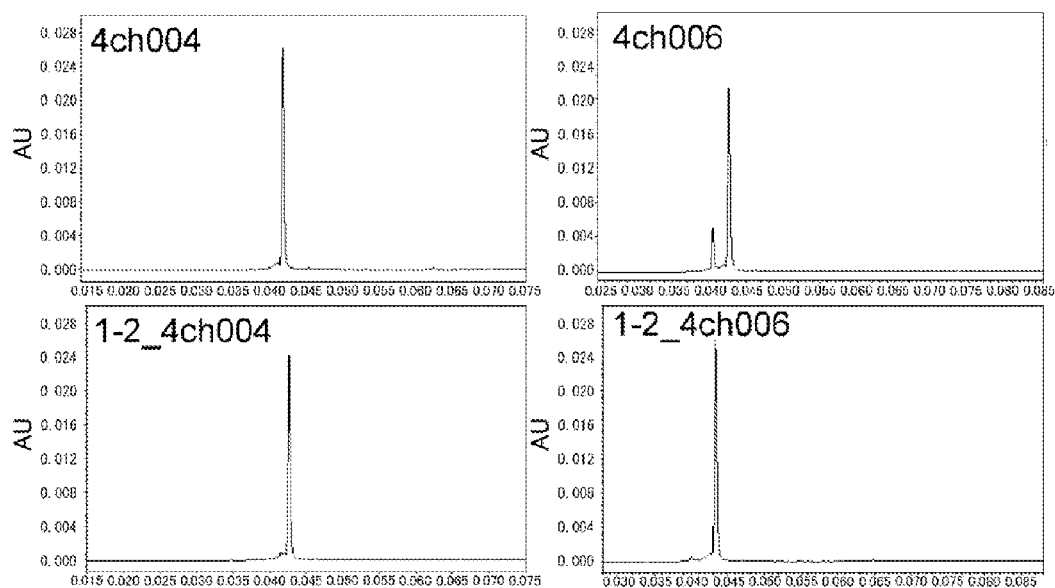
FIG. 10 depicts graphs showing results of the CIEX analysis of each of the antibodies.
Figure 11:
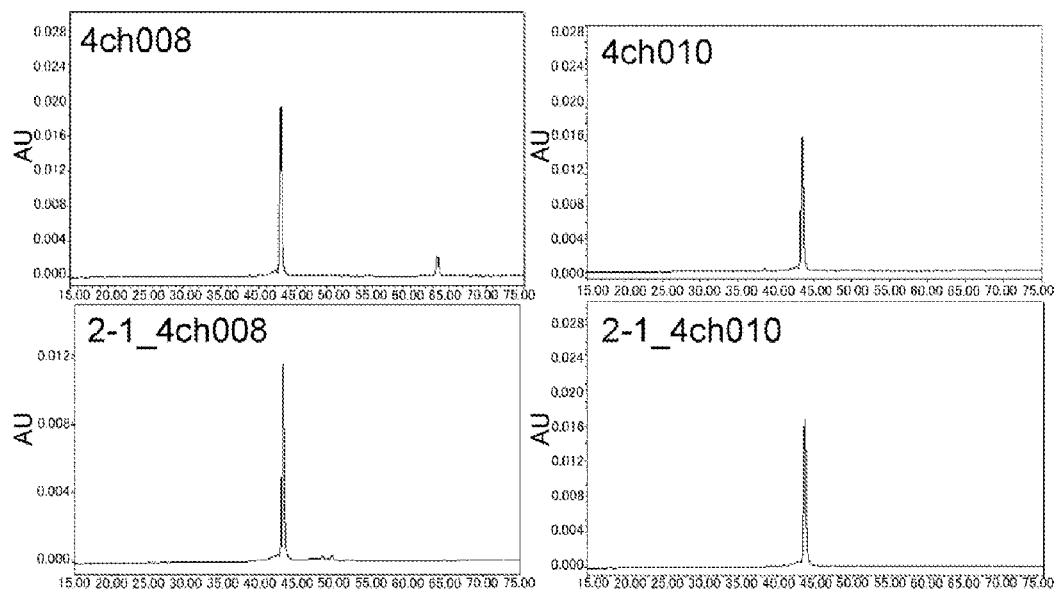
FIG. 11 depicts graphs showing results of the CIEX analysis of each of the antibodies.

Since the peaks observed in the chromatograms of 4ch_006 and 4ch_008, into which mutations for regulating the CH1/CL interface had been introduced, which are thought to represent heterogeneous components, had disappeared in 4ch_1,2 006 and 4ch_2,1 008 into which mutations for regulating the VH/VL interface had been introduced, it became apparent that only target components can be efficiently prepared by applying regulation of the VH/VL interface in addition to regulation of the CH1/CL interface (FIGS. 10 and 11). In addition, the peaks which are thought to represent new heterogeneous components were not detected even if one further made mutations for regulating the VH/VL interface in 4ch_004 and 4ch_010, which had mutations introduced into CH1/CL only, and in which only components that were considered to be target components were thought to be purified (FIGS. 10 and 11).

From the above, it became apparent that the addition of regulation of the VH/VL interface to regulation of the CH1/CL interface further facilitates purification of target components, while it does not have a detrimental effect on the purification when only the target components are thought to be purified already.

Example 7

Measurement of the Tm of Antibodies with Combined Modification Sites

Modifications for regulating the CH1/CL interface may have an effect on Fab stability. Therefore, Fab stability or Tm was measured in accordance with the method of Reference Example 2, for the combinations of TH2/TL17, TH13/TL16, and TH15/TL19. Antibodies in which the H chain/L chain consisted of TH2/TL17, TH13/TL16, and TH15/TL19 were prepared using an anti-IL6R antibody. The combinations of antibody modifications and the expressed antibodies are summarized in Table 11.

TABLE 11

| Hch | | | Lch | | | |
|---|---|---|---|---|---|---|
| name | mutation | SEQ ID NO | name | mutation | SEQ ID NO | Tm |
| G1d | — | 1 | k0 | — | 13 | 95.0 |
| TH2 | Q175K | 3 | TL17 | T180E, S131E, Q160E | 30 | 93.1 |
| TH13 | K147E, Q175E | 10 | TL16 | T180K, S131K, Q160K | 29 | 95.1 |
| TH15 | K147E, Q175E, K213E | 12 | TL19 | T180K, S131K, Q160K, E123K | 32 | 94.8 |

Expression of antibodies was measured in accordance with Reference Example 1, and Tm (° C.) of each of the prepared antibodies was measured in accordance with Reference Example 2. The result shows that the values of Tm for the Fab of G1d/k0 which had no introduction of mutations, and for the Fab of TH2/TL17, TH13/TL16, and TH15/TL19, into which mutations were introduced into CH1/CL, were 95.0° C., 93.1° C., 95.1° C., and 94.8° C., respectively. It revealed that mutations for regulating the CH1/CL interface do not have an effect on Fab stability.

Example 8

Effect of Introducing Mutations for Regulating the CH1/CL Interface on Binding Activity The possibility of modifications for regulating the CH1/CL interface having an effect on antigen binding cannot be completely ruled out. Therefore, in order to measure the affinity for IL-6R and GPC3, binding activities of TH2/TL17, TH13/TL16, and TH15/TL19 were measured in accordance with the method of Reference Example 5 (Table 12).

Since the IL-6R-binding activity and GPC3-binding activity of TH2/TL17, TH13/TL16, and TH15/TL19, into which mutations for regulating the CH1/CL interface have been introduced, were not different from the binding activities of native G1d/k0 to IL-6R and GPC3, it became apparent that modifications for regulating the CH1/CL interface do not affect the affinities. Moreover, when the affinities for the two antigens, IL-6R and GPC3, were measured in accordance with Reference Example 5 using 4ch_004, 4ch_006, 4ch_008, and 4ch_010 prepared in Example 4, it was found that their affinities are equal to that of native G1d/k0 shown in Table 12 (Tables 13 and 14).

According to the studies conducted in Examples 1 to 8, it became apparent that only target components could be efficiently purified by introducing a mutation into CH1/CL, without lowering Fab stability and without lowering binding activity.

TABLE 12

| Affinity to GPC3 | | | | | | | | |
|---|---|---|---|---|---|---|---|---|
| Hch | | | Lch | | | | | |
| name | mutation | SEQ ID NO | name | mutation | SEQ ID NO | ka | kd | KD (nM) |
| G1d | — | SEQ ID NO: 001 | k0 | — | SEQ ID NO: 013 | 2.7E+05 | 3.6E−04 | 1.3E−09 |
| TH2 | Q175K | SEQ ID NO: 003 | TL17 | T180E, S131E, Q160E | SEQ ID NO: 030 | 2.8E+05 | 3.9E−04 | 1.4E−09 |
| TH13 | K147E, Q175E | SEQ ID NO: 010 | TL16 | T180K, S131K, Q160K | SEQ ID NO: 029 | 2.7E+05 | 4.0E−04 | 1.5E−09 |
| TH15 | K147E, Q175E, K213E | SEQ ID NO: 012 | TL19 | T180K, S131K, Q160K, E123K | SEQ ID NO: 032 | 3.9E+05 | 3.8E−04 | 9.9E−10 |

| Affinity to IL6R | | | | | | | | |
|---|---|---|---|---|---|---|---|---|
| Hch | | | Lch | | | | | |
| name | mutation | SEQ ID NO | name | mutation | SEQ ID NO | Kon | Koff | KD (nM) |
| G1d | — | SEQ ID NO: 001 | k0 | — | SEQ ID NO: 013 | 1.5E+05 | 4.1E−04 | 2.8E−09 |
| TH2 | Q175K | SEQ ID NO: 003 | TL17 | T180E, S131E, Q160E | SEQ ID NO: 030 | 1.3E+05 | 5.0E−04 | 3.8E−09 |
| TH13 | K147E, Q175E | SEQ ID NO: 010 | TL16 | T180K, S131K, Q160K | SEQ ID NO: 029 | 1.6E+05 | 4.4E−04 | 2.9E−09 |
| TH15 | K147E, Q175E, K213E | SEQ ID NO: 012 | TL19 | T180K, S131K, Q160K, E123K | SEQ ID NO: 032 | 2.1E+05 | 4.8E−04 | 2.3E−09 |

TABLE 13

| | Ach | | | | Bch | | | | Affinity to GPC3 | | | Affinity to IL6R | | |
|---|---|---|---|---|---|---|---|---|---|---|---|---|---|---|
| NAME | VH | CH | VL | CL | VH | CH | VL | CL | ka | kd | KD (nM) | ka | kd | KD (nM) |
| 4ch_001 | MH0 | G1d | ML0 | k0 | GpH7 | G1d | GpL16 | k0 | 2.7E+05 | 3.6E−04 | 1.3E−09 | 1.5E+05 | 4.1E−04 | 2.8E−09 |
| 4ch_004 | MH0 | TH2k | ML0 | TL17 | GpH7 | TH13h | GpL16 | TL16 | 2.7E+05 | 3.8E−04 | 1.4E−09 | 1.7E+05 | 4.7E−04 | 2.8E−09 |
| 4ch_006 | MH0 | TH2k | ML0 | TL17 | GpH7 | TH15h | GpL16 | TL19 | 3.4E+05 | 4.2E−04 | 1.2E−09 | 2.0E+05 | 4.3E−04 | 2.2E−09 |
| 4ch_001 | MH0 | G1d | ML0 | k0 | GpH7 | G1d | GpL16 | k0 | 2.7E+05 | 3.6E−04 | 1.3E−09 | 1.5E+05 | 4.1E−04 | 2.8E−09 |
| 4ch_008 | MH0 | TH13k | ML0 | TL16 | GpH7 | TH2h | GpL16 | TL17 | 2.6E+05 | 3.9E−04 | 1.5E−09 | 1.6E+05 | 4.6E−04 | 2.8E−09 |
| 4ch_010 | MH0 | TH15k | ML0 | TL19 | GpH7 | TH2h | GpL16 | TL17 | 2.9E+05 | 4.1E−04 | 1.4E−09 | 2.4E+05 | 5.9E−04 | 2.4E−09 |

TABLE 14

| | | VH | | | CH | | |
|---|---|---|---|---|---|---|---|
| NAME | chain | name | mutation | SEQ ID NO | name | mutation | SEQ ID NO |
| 4ch_001 | Ach | MH0 | — | SEQ ID NO: 036 | G1d | K147K | SEQ ID NO: 001 |
| 4ch_004 | Ach | MH0 | — | SEQ ID NO: 036 | TH2k | Q175K | SEQ ID NO: 039 |
| 4ch_006 | Ach | MH0 | — | SEQ ID NO: 036 | TH2k | Q175K | SEQ ID NO: 030 |
| 4ch_001 | Ach | MH0 | — | SEQ ID NO: 036 | G1d | K147K | SEQ ID NO: 001 |
| 4ch_008 | Ach | MH0 | — | SEQ ID NO: 036 | TH13k | K147E, Q175E | SEQ ID NO: 040 |

TABLE 14-continued

| | | | | | | | |
|---|---|---|---|---|---|---|---|
| 4ch_010 | Ach | MH0 | — | SEQ ID NO: 036 | TH15k | K147E, Q175E, K213E | SEQ ID NO: 041 |
| 4ch_001 | Bch | GpH7 | — | SEQ ID NO: 034 | G1d | K147K | SEQ ID NO: 001 |
| 4ch_004 | Bch | GpH7 | — | SEQ ID NO: 034 | TH13h | K147E, Q175E | SEQ ID NO: 044 |
| 4ch_006 | Bch | GpH7 | — | SEQ ID NO: 034 | TH15h | K147E, Q175E, K213E | SEQ ID NO: 045 |
| 4ch_001 | Bch | GpH7 | — | SEQ ID NO: 034 | G1d | K147K | SEQ ID NO: 001 |
| 4ch_008 | Bch | GpH7 | — | SEQ ID NO: 034 | TH2h | Q175K | SEQ ID NO: 043 |
| 4ch_010 | Bch | GpH7 | — | SEQ ID NO: 034 | TH2h | Q175K | SEQ ID NO: 043 |

| | | VL | | | CL | | |
|---|---|---|---|---|---|---|---|
| NAME | chain | name | mutation | SEQ ID NO | name | mutation | SEQ ID NO |
| 4ch_001 | Ach | ML0 | — | SEQ ID NO: 037 | k0 | — | SEQ ID NO: 013 |
| 4ch_004 | Ach | ML0 | — | SEQ ID NO: 037 | TL17 | T180E, S131E, Q160E | SEQ ID NO: 030 |
| 4ch_006 | Ach | ML0 | — | SEQ ID NO: 037 | TL17 | T180E, S131E, Q160E | SEQ ID NO: 030 |
| 4ch_001 | Ach | ML0 | — | SEQ ID NO: 037 | k0 | — | SEQ ID NO: 013 |
| 4ch_008 | Ach | ML0 | — | SEQ ID NO: 037 | TL16 | T180K, S131K, Q160K | SEQ ID NO: 029 |
| 4ch_010 | Ach | ML0 | — | SEQ ID NO: 037 | TL19 | T180K, S131K, Q160K, E123K | SEQ ID NO: 032 |
| 4ch_001 | Bch | GpL16 | — | SEQ ID NO: 035 | k0 | — | SEQ ID NO: 013 |
| 4ch_004 | Bch | GpL16 | — | SEQ ID NO: 035 | TL16 | T180K, S131K, Q160K | SEQ ID NO: 029 |
| 4ch_006 | Bch | GpL16 | — | SEQ ID NO: 035 | TL19 | T180K, S131K, Q160K, E123K | SEQ ID NO: 032 |
| 4ch_001 | Bch | GpL16 | — | SEQ ID NO: 035 | k0 | — | SEQ ID NO: 013 |
| 4ch_008 | Bch | GpL16 | — | SEQ ID NO: 035 | TL17 | T180E, S131E, Q160E | SEQ ID NO: 030 |
| 4ch_010 | Bch | GpL16 | — | SEQ ID NO: 035 | TL17 | T180E, S131E, Q160E | SEQ ID NO: 030 |

Example 9

Amino acid sequences of human IgA1 (SEQ ID NO: 63), IgA2 (SEQ ID NO: 64), IgD (SEQ ID NO: 65), IgE (SEQ ID NO: 66), IgG1 (SEQ ID NO: 67), IgG2 (SEQ ID NO: 68), IgG3 (SEQ ID NO: 69), IgG4 (SEQ ID NO: 70), and IgM (SEQ ID NO: 71) were aligned with respect to CH1 of the H chain; and amino acid sequences of human IgK (Kappa) (SEQ ID NO: 72), IgL1 (SEQ ID NO: 73), IgL2 (SEQ ID NO: 74), IgL3 (SEQ ID NO: 75), IgL6 (SEQ ID NO: 76), and IgL7 (SEQ ID NO: 77) (Lambda) were aligned with respect to CL of the L chain, followed by their respective comparisons. The results are shown in FIG. 12. Modifications discovered in the present example are indicated with arrows. As a result of introducing amino acids having different charges into the H chain and L chain so that the amino acids indicated with the arrows repel between CH1 of the H chain and CL of the L chain as indicated in the present example, it is thought that the target H chain and L chain can be specifically associated.

Reference Example 1

Preparation of Antibody Expression Vectors, and Expression and Purification of Antibodies Amino acid substitutions were introduced according to a method known among those skilled in the art using the QuikChange Site-Directed Mutagenesis Kit (Stratagene), PCR or the In-fusion Advantage PCR Cloning Kit (Takara), etc., followed by construction of expression vectors. The base sequences of the obtained expression vectors were determined according to a method known among those skilled in the art. Antibodies were expressed by transiently transfecting the prepared plasmids into human embryonic kidney cancer cell-derived HEK293H cell lines (Invitrogen) or FreeStyle 293 cells (Invitrogen). Antibodies were purified from the obtained culture supernatant according to a method known among those skilled in the art using rProtein A Sepharose™ Fast Flow (GE Healthcare). The concentration of purified antibodies was determined by measuring absorbance at 280 nm using a spectrophotometer, and the antibody concentration was calculated from the obtained value using an absorption coefficient calculated according to the PACE method (Protein Science 1995; 4: 2411-2423).

Reference Example 2

Evaluation of the Melting Temperature (Tm) of Modified Antibodies by Differential Scanning Calorimetry In this study, thermal stability was evaluated by measuring the melting temperature (Tm) of antibodies using a differential scanning calorimeter; MicroCal Capillary DSC (DKSH).

500 µL aliquot of each antibody solution was placed in a measuring plate and the temperature was increased from 20° C. to 115° C. The rate of temperature increase 120° C./hour and the change in heat capacity was monitored.

The data was analyzed using Origin7 (Light Stone), and the temperature at which a change in heat capacity was observed was calculated and defined as the value of Tm.

Reference Example 3

Anion Exchange Chromatography (AIEX) Analysis

Prepared antibodies were analyzed by the AIEX method using the Alliance System (Waters). Analyses were carried out according to the two-liquid gradient method using TSK-gel DEAE-NPR (Tosoh) for the analytical column, 10 mmol/L Tris-HCl (pH 7.5) for mobile phase A, and 10 mmol/L Tris-HCl and 500 mmol/L NaCl (pH 7.5) for mobile phase B. Measurements were carried out at a wavelength of 280 nm.

Data was analyzed using Empower2 (Waters), followed by calculation of the ratio of each detected peak.

Reference Example 4

Cation Exchange Chromatography (CIEX) Analysis

Prepared antibodies were analyzed by the CIEX method using the Alliance System (Waters). Analyses were carried out according to the two-liquid gradient method using WCX-10 (Dionex) for the analytical column, 25 mmol/L MES (pH 6.1) for mobile phase A, and 25 mmol/L MES and 500 mmol/L NaCl (pH 6.1) for mobile phase B. Measurements were carried out at a wavelength of 280 nm.

Data was analyzed using Empower2 (Waters), followed by calculation of the ratio of each detected peak.

Reference Example 5

Measurement of Affinity for IL6R and GPC3

Interactions between a target antibody and hIL6R or GPC3 were analyzed using Biacore T100 (GE Healthcare). HBS-EP+ (GE Healthcare) was used for the running buffer, and the measurement temperature was 25° C. Protein A/G (Thermo Scientific) was immobilized on the Series S Sensor Chip CM5 (GE Healthcare) by amine coupling, and was used as a chip. A target antibody was captured onto the chip, and interacted with each antigen diluted with running buffer. Antibodies captured on the chip were washed off by reacting with 10 mM glycine-HCl (pH 1.5) to regenerate the chip to be used repeatedly.

The dissociation constant (KD) of each antibody for antigen was calculated by carrying out kinetic analysis on the results of Biacore measurement. More specifically, the association rate constant ka (L/mol/s) and dissociation rate constant kd (1/s) were calculated by global fitting sensorgrams obtained by measuring with the Biacore Evaluation Software in a 1:1 Langmuir binding model, followed by calculation of dissociation constant KD (mol/L) from those values.

INDUSTRIAL APPLICABILITY

The method provided by the present invention enables one to regulate association without altering the structure, function, activity and the like of the original polypeptide (antibody), and is extremely useful since it requires only a small number of amino acid substitutions. In addition, the method also has little influence on antigenicity.

Use of the present invention enables efficient acquisition of bispecific antibodies that actually retain activity.

The invention claimed is:

1. A bispecific antibody comprising:
a first human IgG heavy chain comprising a first heavy chain constant 1 (CH1) domain and a first heavy chain variable region,
a second human IgG heavy chain that is different from the first heavy chain and that comprises a second CH1 domain and a second heavy chain variable region,
a first human kappa light chain comprising a first light chain constant region (CL) and a first light chain variable region, and
a second human kappa light chain that is different from the first light chain and that comprises a second CL and a second light chain variable region,
wherein the first heavy chain and the first light chain associate to bind to a first epitope;
wherein the second heavy chain and second light chain associate to bind to a second epitope;
wherein the first CH1 domain and the second CL include a pair of charged and mutually repelling amino acids at one or more of the following pairs of positions (all positions by EU numbering):
(i) position 147 of the first CH1 domain and position 180 of the second CL,
(ii) position 147 of the first CH1 domain and position 131 of the second CL, and
(iii) position 175 of the first CH1 domain and position 160 of the second CL; and
wherein the pair of charged and mutually repelling amino acids at each of the one or more pairs of positions (i)-(iii) inhibits association between the first CH1 domain and the second CL;
wherein none of the following pairs of positions is occupied by a pair of charged and mutually repelling amino acids:
(iv) position 147 of the first CH1 domain and position 180 of the first CL,
(v) position 147 of the first CH1 domain and position 131 of the first CL,
(vi) position 175 of the first CH1 domain and position 160 of the first CL;
(vii) position 147 of the second CH1 domain and position 180 of the second CL,
(viii) position 147 of the second CH1 domain and position 131 of the second CL, and
(ix) position 175 of the second CH1 domain and position 160 of the second CL,
wherein each of the mutually repelling amino acids of at least one of the pairs is independently selected from either (a) or (b) below:
(a) glutamic acid and aspartic acid; or
(b) lysine, arginine, and histidine.

2. The bispecific antibody of claim 1, wherein the second CH1 domain and the first CL include a pair of charged and mutually repelling amino acids at one or more of the following pairs of positions (all positions by EU numbering):

(x) position 147 of the second CH1 domain and position 180 of the first CL,
(xi) position 147 of the second CH1 domain and position 131 of the first CL, and
(xii) position 175 of the second CH1 domain and position 160 of the first CL,
wherein the pair of charged and mutually repelling amino acids at each of the one or more pairs of positions (x)-(xii) inhibits association between the second CH1 domain and the first CL.

3. The bispecific antibody of claim 1, wherein there is a pair of charged and mutually repelling amino acids at one or both of (A) and (B):
(A) position 213 of the first CH1 domain and position 123 of the second CL; and
(B) position 213 of the second CH1 domain and position 123 of the first CL, wherein all positions are by EU numbering.

4. The bispecific antibody of claim 1, wherein the amino acid at each of positions 147 and 175 of the first CH1 domain is lysine, and the amino acid at each of positions 180, 131, and 160 of the first CL is glutamic acid,
wherein all positions are by EU numbering.

5. The bispecific antibody of claim 1, wherein the amino acid at each of positions 147 and 175 of the second CH1 domain is lysine, and the amino acid at each of positions 180, 131, and 160 of the second CL is glutamic acid,
wherein all positions are by EU numbering.

6. The bispecific antibody of claim 1, wherein the amino acid at each of positions 147 and 175 of the first CH1 domain is glutamic acid, and the amino acid at each of positions 180, 131, and 160 of the first CL is lysine,
wherein all positions are by EU numbering.

7. The bispecific antibody of claim 1, wherein the amino acid at each of positions 147 and 175 of the second CH1 domain is glutamic acid, and the amino acid at each of positions 180, 131, and 160 of the second CL is lysine,
wherein all positions are by EU numbering.

8. The bispecific antibody of claim 4, wherein the amino acid at each of positions 147 and 175 of the second CH1 domain is glutamic acid, and the amino acid at each of positions 180, 131, and 160 of the second CL is lysine,
wherein all positions are by EU numbering.

9. The bispecific antibody of claim 5, wherein the amino acid at each of positions 147 and 175 of the first CH1 domain is glutamic acid, and the amino acid at each of positions 180, 131, and 160 of the first CL is lysine,
wherein all positions are by EU numbering.

10. A composition comprising the bispecific antibody of claim 1 and a pharmaceutically acceptable carrier.

11. The bispecific antibody of claim 1, wherein the first heavy chain and the second heavy chain are IgG1 heavy chains.

12. The bispecific antibody of claim 1, wherein the first heavy chain and the second heavy chain are IgG2 heavy chains.

13. The bispecific antibody of claim 1, wherein the first heavy chain and the second heavy chain are IgG3 heavy chains.

14. The bispecific antibody of claim 1, wherein the first heavy chain and the second heavy chain are IgG4 heavy chains.

15. The bispecific antibody of claim 1, wherein the first CH1 domain and the second CL include a pair of charged and mutually repelling amino acids at each of two or more of the pairs of positions in (i)-(iii).

16. The bispecific antibody of claim 15, wherein the second CH1 domain and the first CL include a pair of charged and mutually repelling amino acids at each of two or more of the pairs of positions in (i)-(iii).

17. A method of producing a bispecific antibody, the method comprising:
(a) identifying four nucleotide sequences respectively encoding the following four starting polypeptides:
a first human IgG heavy chain comprising a first heavy chain constant 1 (CH1) domain and a first heavy chain variable region,
a second human IgG heavy chain that is different from the first heavy chain and that comprises a second CH1 domain that may be the same or different from the first CH1 domain and a second heavy chain variable region,
a first human kappa light chain comprising a first light chain constant region (CL) and a first light chain variable region, and
a second human kappa light chain that is different from the first light chain and that comprises a second CL that may be the same or different from the first CL and a second light chain variable region, wherein the first heavy chain and the first light chain associate to bind to a first epitope and wherein the second heavy chain and second light chain associate to bind to a second epitope;
(b) producing nucleic acid encoding a modified set of four polypeptides identical to the four starting polypeptides except for one or more amino acid substitutions in at least one of the polypeptides, including at least one substitution that alters the charge at one or more of the following EU numbering positions: position 147 or 175 of the first CH1 domain or position 131, 160, or 180 of the second CL;
wherein the at least one charge-altering substitution results in at least one pair of charged and mutually repelling amino acids located at one or more of the following pairs of positions:
(i) position 147 of the first CH1 domain and position 180 of the second CL,
(ii) position 147 of the first CH1 domain and position 131 of the second CL, and
(iii) position 175 of the first CH1 domain and position 160 of the second CL;
wherein a heavy chain and light chain that together comprise the at least one charge-altering substitution have a decreased tendency to associate together, compared to an otherwise-identical heavy chain and light chain that do not comprise the at least one charge-altering substitution;
wherein none of the following pairs of positions in the modified set of four polypeptides is occupied by a pair of charged and mutually repelling amino acids:
(iv) position 147 of the first CH1 domain and position 180 of the first CL,
(v) position 147 of the first CH1 domain and position 131 of the first CL,
(vi) position 175 of the first CH1 domain and position 160 of the first CL;
(vii) position 147 of the second CH1 domain and position 180 of the second CL,
(viii) position 147 of the second CH1 domain and position 131 of the second CL, and
(ix) position 175 of the second CH1 domain and position 160 of the second CL;
(c) providing a host cell comprising the nucleic acid;
(d) culturing the host cell so that it expresses the nucleic acid; and
(e) collecting a bispecific antibody comprising the modified set of four polypeptides from a culture of the host cell,
wherein each of the mutually repelling amino acids of at least one of the pairs numbered (i)-(iii) above is independently selected from either (1) or (2) below:
(1) glutamic acid and aspartic acid; or
(2) lysine, arginine, and histidine.

18. The method of claim 17, wherein the one or more amino acid substitutions further result in at least one pair of charged and mutually repelling amino acids located at one or more of the following pairs of EU numbering positions:
(x) position 147 of the second CH1 domain and position 180 of the first CL,
(xi) position 147 of the second CH1 domain and position 131 of the first CL, and
(xii) position 175 of the second CH1 domain and position 160 of the first CL.

19. The method of claim 17, wherein the one or more amino acid substitutions further result in a pair of charged and mutually repelling amino acids at one or both of (A) and (B):
(A) position 213 of the first CH1 domain and position 123 of the second CL; and
(B) position 213 of the second CH1 domain and position 123 of the first CL,
wherein all positions are by EU numbering.

20. The method of claim 17, wherein, in the modified set of four polypeptides, the amino acid at each of positions 147 and 175 of the first CH1 domain is lysine, and the amino acid at each of positions 180, 131, and 160 of the first CL is glutamic acid,
wherein all positions are by EU numbering.

21. The method of claim 17, wherein, in the modified set of four polypeptides, the amino acid at each of positions 147 and 175 of the second CH1 domain is lysine, and the amino acid at each of positions 180, 131, and 160 of the second CL is glutamic acid,
wherein all positions are by EU numbering.

22. The method of claim 17, wherein, in the modified set of four polypeptides, the amino acid at each of positions 147 and 175 of the first CH1 domain is glutamic acid, and the amino acid at each of positions 180, 131, and 160 of the first CL is lysine,
wherein all positions are by EU numbering.

23. The method of claim 17, wherein, in the modified set of four polypeptides, the amino acid at each of positions 147 and 175 of the second CH1 domain is glutamic acid, and the amino acid at each of positions 180, 131, and 160 of the second CL is lysine,
wherein all positions are by EU numbering.

24. The method of claim 20, wherein the amino acid at each of positions 147 and 175 of the second CH1 domain is glutamic acid, and the amino acid at each of positions 180, 131, and 160 of the second CL is lysine, wherein all positions are by EU numbering.

25. The method of claim 21, wherein the amino acid at each of positions 147 and 175 of the first CH1 domain is glutamic acid, and the amino acid at each of positions 180, 131, and 160 of the first CL is lysine, wherein all positions are by EU numbering.

26. The method of claim 17, wherein the at least one charge-altering substitution in the first CH1 domain and the second CL results in a pair of charged and mutually repelling amino acids at each of two or more of the pairs of positions in (i)-(iii).

27. The method of claim 26, wherein the second CH1 domain and the first CL include a pair of charged and mutually repelling amino acids at each of two or more of the pairs of positions in (i)-(iii).

* * * * *